(12) United States Patent
Panayotova et al.

(10) Patent No.: US 10,881,555 B2
(45) Date of Patent: Jan. 5, 2021

(54) FLUID-ABSORBENT ARTICLE

(71) Applicant: BASF SE, Ludwigshafen am Rhein (DE)

(72) Inventors: Rumyana Panayotova, Mint Hill, NC (US); Ming Vang, Charlotte, NC (US); Kathleen Goebel, Charlotte, NC (US); Xiaomin Zhang, Charlotte, NC (US); Michael Mitchell, Fort Mill, SC (US)

(73) Assignee: BASF SE, Ludwigshafen (DE)

( * ) Notice: Subject to any disclaimer, the term of this patent is extended or adjusted under 35 U.S.C. 154(b) by 922 days.

(21) Appl. No.: 15/471,754

(22) Filed: Mar. 28, 2017

(65) Prior Publication Data

US 2017/0281423 A1    Oct. 5, 2017

(30) Foreign Application Priority Data

Mar. 30, 2016 (EP) .................................. 16162755

(51) Int. Cl.
*A61F 13/53* (2006.01)
*A61L 15/22* (2006.01)
(Continued)

(52) U.S. Cl.
CPC ............ *A61F 13/53* (2013.01); *A61L 15/225* (2013.01); *A61L 15/58* (2013.01); *A61L 15/60* (2013.01);
(Continued)

(58) Field of Classification Search
CPC .......... A61F 13/53; A61F 2013/530481; A61F 2013/5307; A61F 2013/530379;
(Continued)

(56) References Cited

U.S. PATENT DOCUMENTS

| 5,269,980 A | 12/1993 | Levendis et al. |
| 2003/0109840 A1* | 6/2003 | Dodge, II .............. A61L 15/60 |
| | | 604/364 |

(Continued)

FOREIGN PATENT DOCUMENTS

| CA | 2042183 A1 | 11/1991 |
| EP | 348 180 A2 | 12/1989 |

(Continued)

OTHER PUBLICATIONS

Buchholz, Fredric L., et al. *Modern Superabsorbent Polymer Technology*, "Commercial Processes for the Manufacture of Superabsorbent Polymers." New York: John Wiley & Sons, Inc., 1998, pp. 71-103, 252-258.

*Primary Examiner* — Nicholas J. Weiss
*Assistant Examiner* — Jessica R Arble
(74) *Attorney, Agent, or Firm* — Marshall, Gerstein & Borun LLP

(57) ABSTRACT

A fluid-absorbent article having an upper liquid-pervious layer, a lower liquid-impervious layer, a fluid-absorbent core between the layer and the layer, containing from 0 to 20% by weight fibrous material and from 80 to 100% by weight of a water-absorbent polymer material, based on the sum of water-absorbent polymer material and fibrous material. The fluid absorbent article has a first intake time of 15 seconds or less by the hanging U-shape test (HUS).

14 Claims, 25 Drawing Sheets

(51) Int. Cl.
*A61L 15/58* (2006.01)
*A61L 15/60* (2006.01)
*B32B 5/02* (2006.01)
*B32B 7/14* (2006.01)
*B32B 37/12* (2006.01)
*B29C 65/02* (2006.01)

(52) U.S. Cl.
CPC ............ *B32B 5/022* (2013.01); *B32B 7/14* (2013.01); *B32B 37/1284* (2013.01); *A61F 2013/5307* (2013.01); *A61F 2013/53016* (2013.01); *A61F 2013/53051* (2013.01); *A61F 2013/530226* (2013.01); *A61F 2013/530233* (2013.01); *A61F 2013/530379* (2013.01); *A61F 2013/530481* (2013.01); *B29C 65/02* (2013.01); *B32B 2262/0253* (2013.01); *B32B 2305/20* (2013.01); *B32B 2307/726* (2013.01); *B32B 2555/02* (2013.01)

(58) Field of Classification Search
CPC .......... A61F 2013/530715; A61F 2013/15463; A61F 2013/15414; A61F 13/15; A61L 15/60; A61L 15/225; A61L 15/425
See application file for complete search history.

(56) References Cited

U.S. PATENT DOCUMENTS

| | | | |
|---|---|---|---|
| 2007/0219521 A1* | 9/2007 | Hird | A61F 13/84 604/370 |
| 2009/0258994 A1 | 10/2009 | Stueven et al. | |
| 2009/0315204 A1 | 12/2009 | Losch et al. | |
| 2010/0010176 A1 | 1/2010 | Losch et al. | |
| 2010/0029866 A1 | 2/2010 | Losch et al. | |
| 2011/0130275 A1* | 6/2011 | Weismantel | B01J 20/261 502/402 |
| 2014/0045683 A1* | 2/2014 | Loick | A61L 15/22 502/402 |

FOREIGN PATENT DOCUMENTS

| | | |
|---|---|---|
| EP | 0 457 660 A1 | 11/1991 |
| EP | 2565031 A1 | 3/2013 |
| EP | 2668936 A1 | 12/2013 |
| WO | WO-96/40427 A2 | 12/1996 |
| WO | WO-2008/009580 A1 | 1/2008 |
| WO | WO-2008/040715 A2 | 4/2008 |
| WO | WO-2008/052971 A1 | 5/2008 |
| WO | WO-2008/069639 A1 | 6/2008 |
| WO | WO-2008/086976 A1 | 7/2008 |
| WO | WO-2011/026876 A1 | 3/2011 |
| WO | WO-2011/086842 A1 | 7/2011 |
| WO | WO-2011/117263 A1 | 9/2011 |
| WO | WO-2014/079694 A1 | 5/2014 |
| WO | WO-2015/028158 A1 | 3/2015 |
| WO | WO-2015/028327 A1 | 3/2015 |
| WO | WO-2016/135016 A1 | 9/2016 |

* cited by examiner

FLUID-ABSORBENT ARTICLE

CROSS-REFERENCE TO RELATED APPLICATIONS

This application claims the benefit of European Application No. 16162755.9 filed Mar. 30, 2016, incorporated herein by reference in its entirety.

The present invention relates to a fluid-absorbent article comprising an upper liquid-pervious layer (89), a lower liquid-impervious layer (83), a fluid-absorbent core (80) between the layer (89) and the layer (83), comprising from 0 to 20% by weight fibrous material and from 80 to 100% by weight of a water-absorbent polymer material, based on the sum of water-absorbent polymer material and fibrous material; wherein the fluid absorbent article has a first intake time of 15 seconds or less by the hanging U-shape test (HUS).

The production of fluid-absorbent articles is described in the monograph "Modern Superabsorbent Polymer Technology", F. L. Buchholz and A. T. Graham, Wiley-VCH, 1998, pages 252 to 258.

The currently commercially available disposable diapers consist typically of a liquid-pervious topsheet (89), a liquid-impervious backsheet (83), a water-absorbing storage layer (absorbent core) (80) between layers (89) and (83), and an acquisition distribution layer (D) between layers (89) and (80), which usually comprises masses of fibers, i.e. chemically stiffened, twisted, curled cellulosic fibers, non-woven fibrous webs.

Usually the several layers of fluid-absorbent articles fulfill definite functions such as dryness for the upper liquid-pervious layer, vapor permeability without wetting through for the lower liquid-impervious layer, a flexible, vapor permeable and fluid-absorbent core, showing fast absorption rates and being able to retain quantities of body fluids and an acquisition-distribution layer between the upper layer and the core, acting as transport and distribution layer of the discharged body fluids.

The preparation of water-absorbing polymer particles is likewise described in the monograph "Modern Superabsorbent Polymer Technology", F. L. Buchholz and A. T. Graham, Wiley-VCH, 1998, pages 71 to 103. The water-absorbing polymer particles are also referred to as "fluid-absorbing polymer particles", "superabsorbent polymers" or "superabsorbents".

The preparation of water-absorbent polymer particles by polymerizing droplets of a monomer solution is described, for example, in EP 0 348 180 A1, WO 96/40427 A1, U.S. Pat. No. 5,269,980, WO 2008/009580 A1, WO 2008/052971 A1, WO2011/026876 A1, WO 2011/117263 A1 and WO 2014/079694.

Various types and grades of superabsorbents are available. The so called "fast superabsorbents" are typically found among those superabsorbents that also exhibit a specific surface area (i.e. the surface area per mass, as can be easily determined for example by routine BET isotherm measurements), e.g. among those superabsorbents are that:
a) have been produced by an emulsion polymerization process and in particular those that have then been agglomerated (emulsion polymerization is also called suspension polymerization, or most precisely, inverse suspension polymerization);
b) have been produced using blowing agents or any other known means of increasing porosity of superabsorbents, including superabsorbents that are comminuted superabsorbent foam;
c) have been produced by a polymerisation process e.g. electrospinning, resulting in superabsorbent fibers;
d) have been produced by a polymerisation process resulting in freeze dried superabsorbent;
e) have been produced by a polymerisation process in particular those that have a particle size of less than 150 µm and then have been agglomerated.

In the last years, there has been a trend toward very thin disposable diapers. To produce thin disposable diapers, the proportion of cellulose fibers in the water-absorbing storage layer has been lowered or is almost missing.

A core-structure for thin fluid-absorbent products can be formed from absorbent paper. Such structures are for example described in WO2011/086842, EP 2 565 031 A1, EP 2 668 936 A1.

But the known thin fluid-absorbent products comprising laminated fluffless core or absorbent paper structures have deficiencies in respect to fluid acquisition, leakage and rewet properties. To prevent leakage and wet feeling it is preferred to have thicker acquisition-distribution layer's so that the time to absorb the body fluid is preferably short. But this contravenes the trend to thinner absorbent articles, as the thickness is also a great issue in respect to absorbent articles especially in respect to noticeability for adult articles and also hindrance, especially for baby diapers and pants.

BRIEF DESCRIPTION OF THE DRAWINGS

FIG. 1 is an illustration of the process scheme.

FIG. 2 is an illustration of the process scheme using dry air.

FIG. 3 is an illustration of an arrangement of the T_outlet measurement.

FIG. 4 is an illustration of an arrangement of dropletizer units with 3 droplet plates.

FIG. 5 is an illustration of an arrangement of dropletizer units with 9 droplet plates.

FIG. 6 is an illustration of an arrangement of dropletizer units with 9 droplet plates.

FIG. 7 is a schematic view of a longitudinal cut of a dropletizer unit.

FIG. 8 is a cross sectional view of a dropletizer unit.

FIG. 9 is a top-view of a bottom of the internal fluidized bed.

FIG. 10 is a schematic view of openings in the bottom of the internal fluidized bed.

FIG. 11 is a top view of a rake stirrer for the intern fluidized bed.

FIG. 12 is a cross sectional view of a rake stirrer for the intern fluidized bed.

FIG. 13 is an illustration of a process scheme for surface-postcrosslinking.

FIG. 14 is an illustration of a process scheme for surface-postcrosslinking and coating.

FIG. 15 is an illustration of a contact dryer for surface-postcrosslinking.

FIGS. 19A to M are schematic views of the Hanging U-shape Test (HUS-Test) equipment:

FIG. 19 B is a schematic view of the hole unit of FIG. 19A with diaper

FIG. 19 C is a front view of the whole unit of FIG. 19 A.

FIG. 19 D is a top view of the unit of FIG. 19 A.

FIG. 19 E is a schematic side view of the unit of FIG. 19 A—both uprights, outside FIG. 19 F is an inside view of the unit of FIG. 19 A, right upright FIG. 19 G is an inside view of the unit of FIG. 19 A, left upright FIG. 19 H is a front view of the unit of FIG. 19 A, right upright FIG. 19 I is a front view of the unit of FIG. 19 A, left upright FIG. 19 J is a side view of the unit of FIG. 19 A, both legs FIG. 19 K is a front view of the self-centering dosing plate of the unit of FIG. 19A FIG. 19 L is a side view of the self-centering dosing plate of the unit of FIG. 19A.

FIG. 19 M is a top view of the self-centering dosing plate of the unit of FIG. 19A.

Figure 1:
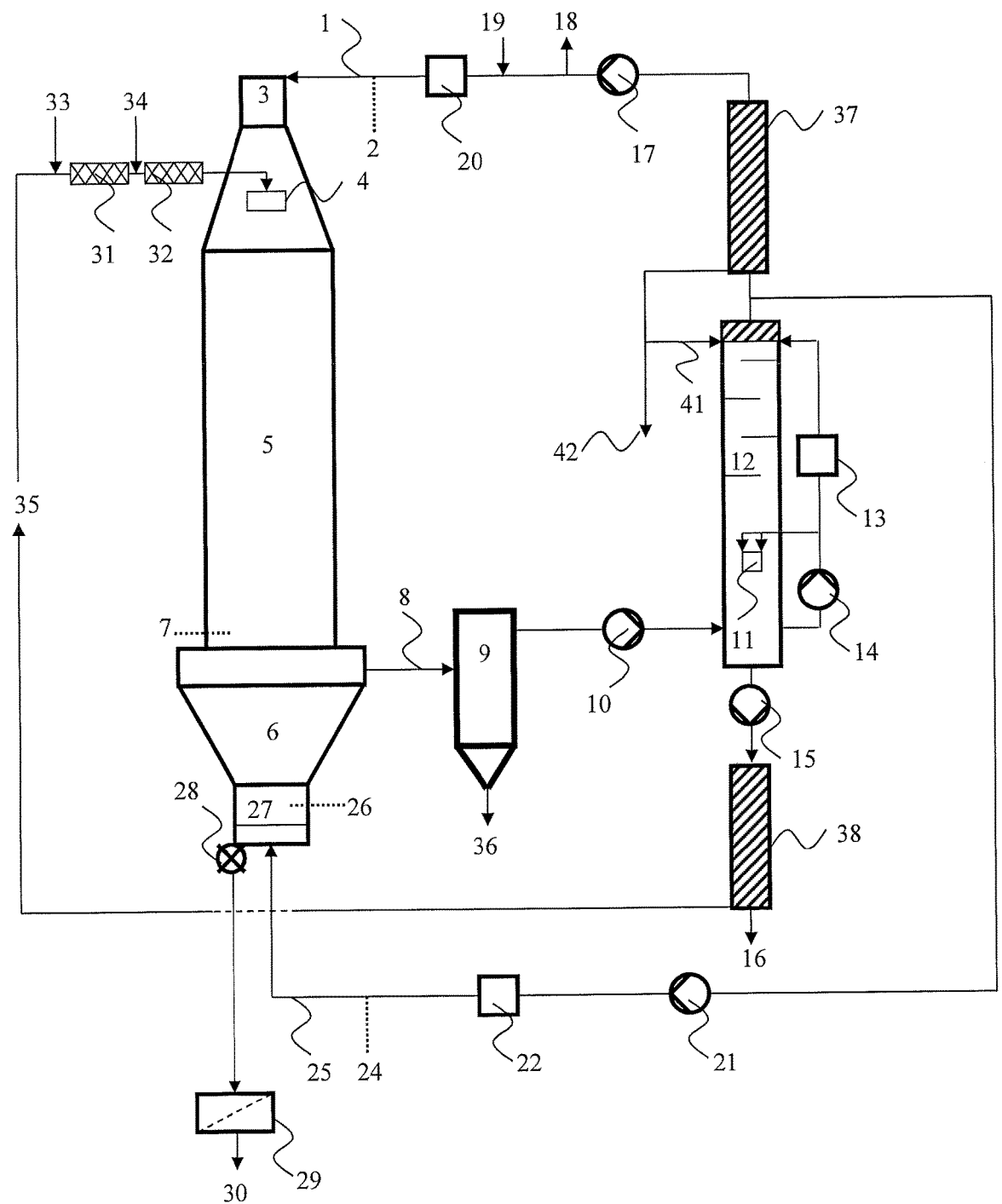
FIGS. 1 to 15 illustrate preferred embodiments for the dropletization process.

It is therefore an object of the present invention to provide ultrathin fluid-absorbent articles with improved liquid acquisition and retention behavior.

It is also an object of the present invention to provide fluid-absorbent articles with improved fluid storage capacity to avoid leakage.

It is furthermore an object of the present invention to provide fluid-absorbent articles with improved rewet performance.

It is also an object of the present invention to provide fluid absorbent mixtures with improved fluid acquisition and storage.

The object is achieved by a fluid-absorbent article, comprising
(A) an upper liquid-pervious layer (89),
(B) a lower liquid-impervious layer (83),
(C) a fluid-absorbent core (80) between the layer (89) and the layer (83), comprising at least one layer (91), comprising from 0 to 20% by weight fibrous material and from 80 to 100% by weight a water-absorbent polymer material, based on the sum of water-absorbent polymer material and fibrous material;
wherein the fluid absorbent article has a first intake time of 15 seconds or less by the hanging U-shape test (HUS).

According to the invention it is preferred that the water-absorbent polymer material in the at least one layer (91) is a fast superabsorbent, preferably having a $t_{corr}$ value (2 g flooded VAUL, 0.3 psi) below 16 s/g and/or a surface area of at least 1000 cm$^2$/g measured by BET as described herein (hereinafter called "fast superabsorbent").

The object is also achieved by a fluid absorbent mixture comprising a blend of at least 20 to 100 wt.-% of a fast superabsorbent and 0 to 80 wt.-% of a second water-absorbent polymer material, preferably the blend comprising at least 30 to 100 wt.-% of a fast superabsorbent and 0 to 70 wt.-% of a second water-absorbent polymer material.

The object is furthermore achieved by a fluid-absorbent article comprising
(A) an upper liquid-pervious layer (89),
(B) a lower liquid-impervious layer (83),
(C) a fluid-absorbent core (80) between the layer (89) and the layer (83), comprising at least one layer (91), comprising from 0 to 20% by weight fibrous material and from 80 to 100% by weight of a blend of at least two water-absorbent polymer materials, based on the sum of water-absorbent polymer material and fibrous material.

According to the invention it is preferred that the blend of at least two water absorbent polymer materials comprises 20 to 100 wt.-% of a first water-absorbent polymer material a fast superabsorbent, preferably having a $t_{corr}$ value (2 g flooded VAUL, 0.3 psi) below 16 s/g and/or a surface area of at least 1000 cm$^2$/g measured by BET as described herein (hereinafter called "fast superabsorbent") and 80 to 0 wt.-% of a second water-absorbent polymer (hereinafter also called "second superabsorbent").

According to one embodiment of the invention the fluid-absorbent article contains no acquisition distribution layer (ADL) between the upper liquid-pervious layer (89) and the fluid-absorbent core (80).

Preferably, especially in case the fluid-absorbent article contains no acquisition distribution layer (ADL) between the upper liquid-pervious layer (89) and the fluid-absorbent core (80) the blend comprises 25 to 100 wt.-% of the fast superabsorbent and 75 to 0 wt.-% of the second superabsorbent. More preferably the blend comprises 30 to 100 wt.-% of the fast superabsorbent and 70 to 0 wt.-% of the second superabsorbent. Even without ADL the inventive fluid absorbent article has a first intake time of 15 seconds or less by the hanging U-shape test (HUS).

To ensure also low rewet even without an ADL present, it is preferred that the blend comprises 30 to 75 wt.-% of the second superabsorbent and 70 to 25 wt.-% of the fast superabsorbent. It is also preferred that the blend comprises 30 to 70 wt.-% of the second superabsorbent and 70 to 30 wt.-% of the fast superabsorbent. According to another embodiment of the present invention it is preferred that the blend comprises 35 to 65 wt.-% of the second superabsorbent and 65 to 35 wt.-% of the fast superabsorbent.

According to the invention it is preferred that the second superabsorbent having a spericity of at least 0.89.

The second superabsorbent is preferably produced by polymerizing droplets of the monomer in a surrounding heated gas phase.

According to the invention it is also preferred that the fast superabsorbent having a $t_{corr}$ value of 12 sec/g or less, preferably 7.5 sec/g or less, most preferably 6 sec/g or less. The $t_{corr}$ is defined by the following equation:

$$t_{corr} = \frac{\frac{t_{12g}}{g}}{(SA/100)m_{sap}}$$

It is furthermore preferred that the fast superabsorbent having a surface area of at least 1000 cm$^2$/g.

The second superabsorbent having preferably a CRC of at least 30 g/g.

It is preferred that the second water-absorbent polymer particles have an absorbency under load AUL (0.3 psi, 21.0 g/cm$^2$, WSP 242.3 (11)) of at least 30 g/g.

It is also preferred that the second superabsorbent itself is a blend of at least two of at least two water-absorbent polymer materials.

According to the invention it is preferred that the fast superabsorbent and/or the second superabsorbent are surface-postcrosslinked.

In one embodiment of the present invention the fluid-absorbent articles are comprising water-absorbent polymer particles and less than 10% by weight fibrous material and/or 5% or less by weight of adhesives in the absorbent core.

Furthermore according to another embodiment of the invention the at least one layer of the absorbent core contains at least 100 gsm water absorbent polymer particles.

Suitable water-absorbent polymers are produced by a process, comprising the steps forming water-absorbent polymer particles by polymerizing a monomer solution, comprising
a) at least one ethylenically unsaturated monomer which bears acid groups and may be at least partly neutralized,
b) optionally one or more crosslinker,
c) at least one initiator,
d) optionally one or more ethylenically unsaturated monomers copolymerizable with the monomers mentioned under a),
e) optionally one or more water-soluble polymers, and
f) water,
optionally coating of water-absorbent polymer particles with at least one surface-postcrosslinker and thermal surface-postcrosslinking of the coated water-absorbent polymer particles.

Suitable methods of making are described in the literature. Superabsorbents are obtained for example by
gel polymerisation in the batch process or tubular reactor and subsequent comminution in meat grinder, extruder or kneader, as described for example in EP 445 619 A2 and DE 19 846 413 A1;
polymerisation in kneader with continuous comminution by contrarotatory stirring shafts for example, as described for example in WO 01/38 402 A1;
polymerisation on belt and subsequent comminution in meat grinder, extruder or kneader, as described for example in EP 955 086 A2, DE 38 25 366 A1 or U.S. Pat. No. 6,241,928;
emulsion polymerisation, which produces bead polymers having a relatively narrow gel size distribution, as described for example in EP 457 660 A1;
polymerizing droplets of the monomer in a surrounding heated gas phase, for example using a system described in WO 2008/040715 A2, WO 2008/052971 A1, WO 2008/069639 A1 and WO 2008/086976 A1, WO 2014/079694, WO 2015/028327, WO 2015/028158

It is preferred to produce fast superabsorbents e.g. with a $t_{corr}$ value (2 g flooded VAUL, 0.3 psi) below 16 s/g and/or a surface area of at least 1000 cm$^2$/g by suspension polymerization or agglomerated fine superabsorbent particle technology.

Whereas agglomerated fine superabsorbent particle technology comprises the agglomeration of particles with a particle size of less than 150 µm removed from the superabsorbent production.

It is preferred to produce the second superabsorbent by polymerizing droplets of the monomer in a surrounding heated gas phase, for example using a system described in WO 2008/040715 A2, WO 2008/052971 A1, WO 2008/069639 A1 and WO 2008/086976 A1, WO 2014/079694, WO 2015/028327, WO 2015/028158.

DETAILED DESCRIPTION OF THE INVENTION

A. Definitions

As used herein, the term "fluid-absorbent article" refers to any three-dimensional solid material being able to acquire and store fluids discharged from the body. Preferred fluid-absorbent articles are disposable fluid-absorbent articles that are designed to be worn in contact with the body of a user such as disposable fluid-absorbent pantyliners, sanitary napkins, catamenials, incontinence inserts/pads, diapers, training pant diapers, breast pads, interlabial inserts/pads or other articles useful for absorbing body fluids.

As used herein, the term "fluid-absorbent composition" refers to a component of the fluid-absorbent article which is primarily responsible for the fluid handling of the fluid-absorbent article including acquisition, transport, distribution and storage of body fluids.

As used herein, the term "fluid-absorbent core", "absorbent core" or "absorbent paper" refers to a fluid-absorbent composition comprising at least one layer of water-absorbent polymer particles and optionally fibrous material, nonwoven material and tissue material. The fluid-absorbent core is primarily responsible for the fluid handling of the fluid-absorbent article including acquisition, transport, distribution and storage of body fluids.

As used herein, the term "layer" refers to a fluid-absorbent composition whose primary dimension is along its length and width. It should be known that the term "layer" is not necessarily limited to single layers or sheets of the fluid-absorbent composition. Thus a layer can comprise laminates, composites, combinations of several sheets or webs of different materials.

As used herein the term "x-dimension" refers to the length, and the term "y-dimension" refers to the width of the fluid-absorbent composition, layer, core or article. Generally, the term "x-y-dimension" refers to the plane, orthogonal to the height or thickness of the fluid-absorbent composition, layer, core or article.

As used herein the term "z-dimension" refers to the dimension orthogonal to the length and width of the fluid absorbent composition, layer, core or article. Generally, the term "z-dimension" refers to the height of the fluid-absorbent composition, layer, core or article.

As used herein, the term "basis weight" indicates the weight of the fluid-absorbent core per square meter and it includes the chassis of the fluid-absorbent article. The basis weight is determined at discrete regions of the fluid-absorbent core: the front overall average is the basis weight of the fluid-absorbent core 5.5 cm forward of the center of the core to the front distal edge of the core; the insult zone is the basis weight of the fluid-absorbent core 5.5 cm forward and 0.5 cm backwards of the center of the core; the back overall average is the basis weight of the fluid-absorbent core 0.5 cm backward of the center of the core to the rear distal edge of the core.

Further, it should be understood, that the term "upper" refers to fluid-absorbent composition which are nearer to the wearer of the fluid-absorbent article. Generally, the topsheet is the nearest composition to the wearer of the fluid-absorbent article, hereinafter described as "upper liquid-pervious layer". Contrarily, the term "lower" refers to fluid-absorbent compositions which are away from the wearer of the fluid-absorbent article. Generally, the backsheet is the component which is furthermost away from the wearer of the fluid-absorbent article, hereinafter described as "lower liquid-impervious layer".

As used herein, the term "liquid-pervious" refers to a substrate, layer or a laminate thus permitting liquids, i.e. body fluids such as urine, menses and/or vaginal fluids to readily penetrate through its thickness.

As used herein, the term "liquid-impervious" refers to a substrate, layer or a laminate that does not allow body fluids to pass through in a direction generally perpendicular to the plane of the layer at the point of liquid contact under ordinary use conditions.

As used herein, the term "chassis" refers to fluid-absorbent material comprising the upper liquid-pervious layer and the lower liquid-impervious layer, elastication and closure systems for the absorbent article.

As used herein, the term "hydrophilic" refers to the wettability of fibers by water deposited on these fibers. The term "hydrophilic" is defined by the contact angle and surface tension of the body fluids. According to the definition of Robert F. Gould in the 1964 American Chemical Society publication "Contact angle, wettability and adhesion", a fiber is referred to as hydrophilic, when the contact angle between the liquid and the fiber, especially the fiber surface, is less than 90° or when the liquid tends to spread spontaneously on the same surface.

Contrarily, term "hydrophobic" refers to fibers showing a contact angle of greater than 90° or no spontaneously spreading of the liquid across the surface of the fiber.

As used herein, the term "body fluids" refers to any fluid produced and discharged by human or animal body, such as urine, menstrual fluids, faeces, vaginal secretions and the like.

As used herein, the term "breathable" refers to a substrate, layer, film or a laminate that allows vapour to escape from the fluid-absorbent article, while still preventing fluids from leakage. Breathable substrates, layers, films or laminates may be porous polymeric films, nonwoven laminates from spunbond and melt-blown layers, laminates from porous polymeric films and nonwovens.

As used herein, the term "longitudinal" refers to a direction running perpendicular from a waist edge to an opposing waist edge of the fluid-absorbent article.

B. Water-Absorbent Polymer Particles

The water-absorbent polymer particles are generally prepared by a process, comprising the steps forming water-absorbent polymer particles by polymerizing a monomer solution, comprising
g) at least one ethylenically unsaturated monomer which bears acid groups and may be at least partly neutralized,
h) optionally one or more crosslinker,
i) at least one initiator,
j) optionally one or more ethylenically unsaturated monomers copolymerizable with the monomers mentioned under a),
k) optionally one or more water-soluble polymers, and
l) water,
optionally coating of water-absorbent polymer particles with at least one surface-postcrosslinker and thermal surface-postcrosslinking of the coated water-absorbent polymer particles.

Preferably the content of residual monomers in the water-absorbent polymer particles prior to the coating with the surface-postcrosslinker is in the range from 0.03 to 15% by weight, a preferred surface-postcrosslinker is an alkylene carbonate, and the temperature during the thermal surface-postcrosslinking is in the range from 100 to 180° C.

The water-absorbent polymer particles are typically insoluble but swellable in water.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids such as acrylic acid, methacrylic acid, maleic acid, and itaconic acid. Particularly preferred monomers are acrylic acid and methacrylic acid. Very particular preference is given to acrylic acid.

Further suitable monomers a) are, for example, ethylenically unsaturated sulfonic acids such as vinylsulfonic acid, styrenesulfonic acid and 2-acrylamido-2-methylpropanesulfonic acid (AMPS).

Impurities may have a strong impact on the polymerization. Preference is given to especially purified monomers a). Useful purification methods are disclosed in WO 2002/055469 A1, WO 2003/078378 A1 and WO 2004/035514 A1. A suitable monomer a) is according to WO 2004/035514 A1 purified acrylic acid having 99.8460% by weight of acrylic acid, 0.0950% by weight of acetic acid, 0.0332% by weight of water, 0.0203 by weight of propionic acid, 0.0001% by weight of furfurals, 0.0001% by weight of maleic anhydride, 0.0003% by weight of diacrylic acid and 0.0050% by weight of hydroquinone monomethyl ether.

Polymerized diacrylic acid is a source for residual monomers due to thermal decomposition. If the temperatures during the process are low, the concentration of diacrylic acid is no more critical and acrylic acids having higher concentrations of diacrylic acid, i.e. 500 to 10,000 ppm, can be used for the inventive process.

The content of acrylic acid and/or salts thereof in the total amount of monomers a) is preferably at least 50 mol %, more preferably at least 90 mol %, most preferably at least 95 mol %.

The acid groups of the monomers a) are typically partly neutralized in the range of 0 to 100 mol %, preferably to an extent of from 25 to 85 mol %, preferentially to an extent of from 50 to 80 mol %, more preferably from 60 to 75 mol %, for which the customary neutralizing agents can be used, preferably alkali metal hydroxides, alkali metal oxides, alkali metal carbonates or alkali metal hydrogen carbonates, and mixtures thereof. Instead of alkali metal salts, it is also possible to use ammonia or organic amines, for example, triethanolamine. It is also possible to use oxides, carbonates, hydrogencarbonates and hydroxides of magnesium, calcium, strontium, zinc or aluminum as powders, slurries or solutions and mixtures of any of the above neutralization agents. Example for a mixture is a solution of sodiumaluminate. Sodium and potassium are particularly preferred as alkali metals, but very particular preference is given to sodium hydroxide, sodium carbonate or sodium hydrogen carbonate, and mixtures thereof. Typically, the neutralization is achieved by mixing in the neutralizing agent as an aqueous solution, as a melt or preferably also as a solid. For example, sodium hydroxide with water content significantly below 50% by weight may be present as a waxy material having a melting point above 23° C. In this case, metered addition as piece material or melt at elevated temperature is possible.

Optionally, it is possible to add to the monomer solution, or to starting materials thereof, one or more chelating agents for masking metal ions, for example iron, for the purpose of stabilization. Suitable chelating agents are, for example, alkali metal citrates, citric acid, alkali metal tartrates, alkali metal lactates and glycolates, pentasodium triphosphate, ethylenediamine tetraacetate, nitrilotriacetic acid, and all chelating agents known under the Trilon® name, for example Trilon® C (pentasodium diethylenetriaminepentaacetate), Trilon® D (trisodium (hydroxyethyl)-ethylenediaminetriacetate), and Trilon® M (methylglycinediacetic acid) and Cublen®.

The monomers a) comprise typically polymerization inhibitors, preferably hydroquinone monoethers, as inhibitor for storage.

The monomer solution comprises preferably up to 250 ppm by weight, more preferably not more than 130 ppm by weight, most preferably not more than 70 ppm by weight, preferably not less than 10 ppm by weight, more preferably not less than 30 ppm by weight and especially about 50 ppm by weight of hydroquinone monoether, based in each case on acrylic acid, with acrylic acid salts being counted as acrylic acid. For example, the monomer solution can be prepared using acrylic acid having appropriate hydroquinone monoether content. The hydroquinone monoethers may, however, also be removed from the monomer solution by absorption, for example on activated carbon.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized by a free-radical mechanism into the polymer chain and functional groups which can form covalent bonds with the acid groups of monomer a). In addition, polyvalent metal ions which can form coordinate bond with at least two acid groups of monomer a) are also suitable crosslinkers b).

The crosslinkers b) are preferably compounds having at least two free-radically polymerizable groups which can be polymerized by a free-radical mechanism into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and in DE 103 31 450 A1, mixed acrylates which, as well as acrylate groups, comprise further ethylenically unsaturated groups, as described in DE 103 314 56 A1 and DE 103 55 401 A1, or crosslinker mixtures, as described, for example, in DE 195 43 368 A1, DE 196 46 484 A1, WO 90/15830 A1 and WO 2002/32962 A2.

Suitable crosslinkers b) are in particular pentaerythritol triallyl ether, tetraallyloxyethane, polyethyleneglycole diallylethers (based on polyethylene glycole having a molecular weight between 400 and 20000 g/mol), N,N'-methylenebisacrylamide, 15-tuply ethoxylated trimethylolpropane, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example in WO 2003/104301 A1. Di- and/or triacrylates of 3- to 18-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol and especially the triacrylate of 3-tuply ethoxylated glycerol.

The amount of crosslinker b) is preferably from 0.0001 to 0.6% by weight, more preferably from 0.001 to 0.2% by weight, most preferably from 0.01 to 0.06% by weight, based in each case on monomer a). On increasing the amount of crosslinker b) the centrifuge retention capacity (CRC) decreases and the absorption under a pressure of 21.0 g/cm$^2$ (AUL) passes through a maximum.

The surface-postcrosslinked polymer particles of the present invention surprisingly require very little or even no cross-linker during the polymerization step. So, in one particularly preferred embodiment of the present invention no crosslinker b) is used.

The initiators c) used may be all compounds which disintegrate into free radicals under the polymerization conditions, for example peroxides, hydroperoxides, hydrogen peroxide, persulfates, azo compounds and redox initiators. Preference is given to the use of water-soluble initiators. In some cases, it is advantageous to use mixtures of various initiators, for example mixtures of hydrogen peroxide and sodium or potassium peroxodisulfate. Mixtures of hydrogen peroxide and sodium peroxodisulfate can be used in any proportion.

Particularly preferred initiators c) are azo initiators such as 2,2'-azobis[2-(2-imidazolin-2-yl)propane] dihydrochloride and 2,2'-azobis[2-(5-methyl-2-imidazolin-2-yl)propane] dihydrochloride, 2,2'-azobis(2-amidinopropane) dihydrochloride, 4,4'-azobis(4-cyanopentanoic acid), 4,4'-azobis (4-cyanopentanoic acid) sodium salt, 2,2'-azobis[2-methyl-N-(2-hydroxyethyl)propionamide], and photoinitiators such as 2-hydroxy-2-methylpropiophenone and 1-[4-(2-hydroxyethoxy)phenyl]-2-hydroxy-2-methyl-1-propan-1-one, redox initiators such as sodium persulfate/hydroxymethylsulfinic acid, ammonium peroxodisulfate/hydroxymethylsulfinic acid, hydrogen peroxide/hydroxymethylsulfinic acid, sodium persulfate/ascorbic acid, ammonium peroxodisulfate/ascorbic acid and hydrogen peroxide/ascorbic acid, photoinitiators such as 1-[4-(2-hydroxyethoxy)phenyl]-2-hydroxy-2-methyl-1-propan-1-one, and mixtures thereof. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany). Of course it is also possible within the scope of the present invention to use the purified salts or acids of 2-hydroxy-2-sulfinatoacetic acid and 2-hydroxy-2-sulfonatoacetic acid—the latter being available as sodium salt under the trade name Blancolene® (Brüggemann Chemicals; Heilbronn; Germany).

The initiators are used in customary amounts, for example in amounts of from 0.001 to 5% by weight, preferably from 0.01 to 2% by weight, most preferably from 0.05 to 0.5% by weight, based on the monomers a).

Examples of ethylenically unsaturated monomers d) which are copolymerizable with the monomers a) are acrylamide, methacrylamide, hydroxyethyl acrylate, hydroxyethyl methacrylate, dimethylaminoethyl acrylate, dimethylaminoethyl methacrylate, dimethylaminopropyl acrylate and diethylaminopropyl methacrylate.

Useful water-soluble polymers e) include polyvinyl alcohol, modified polyvinyl alcohol comprising acidic side groups for example Poval® K (Kuraray Europe GmbH; Frankfurt; Germany), polyvinylpyrrolidone, starch, starch derivatives, modified cellulose such as methylcellulose, carboxymethylcellulose or hydroxyethylcellulose, gelatin, polyglycols or polyacrylic acids, polyesters and polyamides, polylactic acid, polyglycolic acid, co-polylactic-polyglycolic acid, polyvinylamine, polyallylamine, water soluble copolymers of acrylic acid and maleic acid available as Sokalan® (BASF SE; Ludwigshafen; Germany), preferably starch, starch derivatives and modified cellulose.

For optimal action, the preferred polymerization inhibitors require dissolved oxygen. Therefore, the monomer solution can be freed of dissolved oxygen before the polymerization by inertization, i.e. flowing through with an inert gas, preferably nitrogen. It is also possible to reduce the concentration of dissolved oxygen by adding a reducing agent. The oxygen content of the monomer solution is preferably lowered before the polymerization to less than 1 ppm by weight, more preferably to less than 0.5 ppm by weight.

The water content of the monomer solution is preferably less than 65% by weight, preferentially less than 62% by weight, more preferably less than 60% by weight, most preferably less than 58% by weight.

The monomer solution has, at 20° C., a dynamic viscosity of preferably from 0.002 to 0.02 Pa·s, more preferably from 0.004 to 0.015 Pa·s, most preferably from 0.005 to 0.01 Pa·s. The mean droplet diameter in the droplet generation rises with rising dynamic viscosity.

The monomer solution has, at 20° C., a density of preferably from 1 to 1.3 g/cm$^3$, more preferably from 1.05 to 1.25 g/cm$^3$, most preferably from 1.1 to 1.2 g/cm$^3$.

The monomer solution has, at 20° C., a surface tension of from 0.02 to 0.06 N/m, more preferably from 0.03 to 0.05 N/m, most preferably from 0.035 to 0.045 N/m. The mean droplet diameter in the droplet generation rises with rising surface tension.

Polymerization

Superabsorbents are typically obtained by polymerisation of an aqueous monomer solution and optionally a subsequent comminution of the hydrogel. Suitable methods of making are described in the literature. Superabsorbents are obtained for example by gel polymerisation in the batch process or tubular reactor and subsequent comminution in meat grinder, extruder or kneader, as described for example in EP 445 619 A2 and DE 19 846 413 A1;

polymerisation in kneader with continuous comminution by contrarotatory stirring shafts for example, as described for example in WO 01/38 402 A1;

polymerisation on belt and subsequent comminution in meat grinder, extruder or kneader, as described for example in EP 955 086 A2, DE 38 25 366 A1 or U.S. Pat. No. 6,241,928;

emulsion polymerisation, which produces bead polymers having a relatively narrow gel size distribution, as described for example in EP 457 660 A1;

polymerizing droplets of the monomer in a surrounding heated gas phase, for example using a system described in WO 2008/040715 A2, WO 2008/052971 A1, WO 2008/069639 A1 and WO 2008/086976 A1, WO 2014/079694, WO 2015/028327, WO 2015/028158.

The cited references are expressly incorporated herein for details of process operation. The reaction is preferably carried out by emulsion polymerisation for the fast superabsorbent or by polymerizing droplets of the monomer solution for the second superabsorbent.

A preferred process for producing fast superabsorbents of this invention is emulsion polymerization. Emulsion polymerization—also referred to a suspension polymerization or inverse suspension polymerization—is a process in which the aqueous monomer solution is finely dispersed in a continuous water-immiscible phase, typically a hydrocarbon solvent and polymerized in this dispersed state. The dispersion is stabilized by adding a stabilizer, generally a surfactant and/or very fine particles of an inorganic, usually hydrophobic solid such as hydrophobized silica. This process yields gel beads of rather uniform particle size that can easily be controlled by adjusting the agitation of the polymerization suspension. The most simple, but not the only means therefor is adjusting stirring speed during polymerization. Grinding or sizing steps are rarely necessary with emulsion polymerization. The initially produced particles, however, are gel particles since they contain all the water that had been part of the monomer solution and need to be dried just as the initial gel products from solution polymerization processes. Producing rather small particles and agglomerating these to agglomerates as it is e.g. disclosed in PCT/EP2016/053317, or producing porous beads by oil-in-water-in-oil polymerization, where the dispersed aqueous phase monomer droplets contain organic phase microdroplets that evaporate during polymerization or drying and leave pores in the beads, or any known means to increase specific surface all lead to rather "fast" superabsorbents. Emulsion polymerization processes for producing superabsorbents and superabsorbents produced by this process are known.

The dry superabsorbing polymers thus produced are typically known as "base polymers" and are then preferably surface postcrosslinked. Surface postcrosslinking can be accomplished in a conventional manner using dried, ground and classified polymeric particles. For surface postcrosslinking, compounds capable of reacting with the functional groups of the base polymer by crosslinking are applied, usually in the form of a solution, to the surface of the base polymer particles as described below.

Water-absorbent polymer particles prepared by suspension polymerisation have a centrifuge retention capacity (CRC) 15 to 35 g/g, preferably 20 to 34 g/g, more preferably 22 to 33 g/g, auf.

The water-absorbent polymer particles have an absorption under high load of 49.2 g/cm$^2$ (AUHL) of 18 to 30 g/g, preferably 19 to 28 g/g, more preferably 20 to 26 g/g.

The apparent bulk density (ABD) of the water-absorbent particles is less than 0.7, preferably less than 0.6, more preferably less than 0.5.

A furthermore suited process for producing fast superabsorbents of this invention is the agglomeration of superabsorbent fine particles, a fraction of absorbent particles with a particle size of less than 150 µm removed from the superabsorbent production and agglomerating these to agglomerates. The agglomerates may also be surface postcrosslinked.

Water-absorbent polymer particles prepared by agglomeration of superabsorbent fine particles have a centrifuge retention capacity (CRC) 15 to 30 g/g, preferably 16 to 23 g/g.

The water-absorbent polymer particles have an absorption under high load of 49.2 g/cm$^2$ (AUHL) of 15 to 25 g/g, preferably 16 bis 22 g/g.

The apparent bulk density (ABD) of the water-absorbent particles e.g. prepared by agglomeration is less than 0.6, preferably less than 0.5.

It is preferred to produce the second superabsorbent by polymerizing droplets of the monomer in a surrounding heated gas phase, for example using a system described in WO 2008/040715 A2, WO 2008/052971 A1, WO 2008/069639 A1 and WO 2008/086976 A1, WO 2014/079694, WO 2015/028327, WO 2015/028158.

The droplets are preferably generated by means of a droplet plate. A droplet plate is a plate having a multitude of bores, the liquid entering the bores from the top. The droplet plate or the liquid can be oscillated, which generates a chain of ideally monodisperse droplets at each bore on the underside of the droplet plate. In a preferred embodiment, the droplet plate is not agitated.

It is also possible to use two or more droplet plates with different bore diameters so that a range of desired particle sizes can be produced. It is preferable that each droplet plate carries only one bore diameter, however mixed bore diameters in one plate are also possible.

The number and size of the bores are selected according to the desired capacity and droplet size. The droplet diameter is typically 1.9 times the diameter of the bore. What is important here is that the liquid to be dropletized does not pass through the bore too rapidly and the pressure drop over the bore is not too great. Otherwise, the liquid is not dropletized, but rather the liquid jet is broken up (sprayed) owing to the high kinetic energy. In a preferred embodiment of the present invention the pressure drop is from 4 to 5 bar. The Reynolds number based on the throughput per bore and the bore diameter is preferably less than 2000, preferentially less than 1600, more preferably less than 1400 and most preferably less than 1200.

The underside of the droplet plate has at least in part a contact angle preferably of at least 60°, more preferably at least 75° and most preferably at least 90° with regard to water.

The contact angle is a measure of the wetting behavior of a liquid, in particular water, with regard to a surface, and can be determined using conventional methods, for example in accordance with ASTM D 5725. A low contact angle denotes good wetting, and a high contact angle denotes poor wetting.

It is also possible for the droplet plate to consist of a material having a lower contact angle with regard to water, for example a steel having the German construction material code number of 1.4571, and be coated with a material having a larger contact angle with regard to water.

Useful coatings include for example fluorous polymers, such as perfluoroalkoxyethylene, polytetrafluoroethylene, ethylene-chlorotrifluoroethylene copolymers, ethylene-tetrafluoroethylene copolymers and fluorinated polyethylene.

The coatings can be applied to the substrate as a dispersion, in which case the solvent is subsequently evaporated off and the coating is heat treated. For polytetrafluoroethylene this is described for example in U.S. Pat. No. 3,243,321.

Further coating processes are to be found under the headword "Thin Films" in the electronic version of "Ullmann's Encyclopedia of Industrial Chemistry" (Updated Sixth Edition, 2000 Electronic Release).

The coatings can further be incorporated in a nickel layer in the course of a chemical nickelization.

It is the poor wettability of the droplet plate that leads to the production of monodisperse droplets of narrow droplet size distribution.

The droplet plate has preferably at least 5, more preferably at least 25, most preferably at least 50 and preferably up to 2000, more preferably up to 1500 bores, most preferably up to 1000.

The diameter of the bores is adjusted to the desired droplet size.

The spacing of the bores is usually from 2 to 50 mm, preferably from 3 to 40 mm, more preferably from 4 to 30 mm, most preferably from 5 to 25 mm. Smaller spacings of the bores may cause agglomeration of the polymerizing droplets.

The diameter of the bores size area is 1900 to 22300 $\mu m^2$, more preferably from 7800 to 20100 $\mu m^2$, most preferably from 11300 to 17700 $\mu m^2$. Circular bores are preferred with a bore size from 50 to 170 $\mu m$, more preferably from 100 to 160 $\mu m$, most preferably from 120 to 150 $\mu m$.

For optimizing the average particle diameter, droplet plates with different bore diameters can be used. The variation can be done by different bores on one plate or by using different plates, where each plate has a different bore diameter. The average particle size distribution can be monomodal, bimodal or multimodal. Most preferably it is monomodal or bimodal.

The temperature of the monomer solution as it passes through the bore is preferably from 5 to 80° C., more preferably from 10 to 70° C., most preferably from 30 to 60° C.

A carrier gas flows through the reaction zone. The carrier gas may be conducted through the reaction zone in cocurrent to the free-falling droplets of the monomer solution, i.e. from the top downward. After one pass, the gas is preferably recycled at least partly, preferably to an extent of at least 50%, more preferably to an extent of at least 75%, into the reaction zone as cycle gas. Typically, a portion of the carrier gas is discharged after each pass, preferably up to 10%, more preferably up to 3% and most preferably up to 1%.

The oxygen content of the carrier gas is preferably from 0.1 to 25% by volume, more preferably from 1 to 10% by volume, most preferably from 2 to 7% by weight. In the scope of the present invention it is also possible to use a carrier gas which is free of oxygen. As well as oxygen, the carrier gas preferably comprises nitrogen. The nitrogen content of the gas is preferably at least 80% by volume, more preferably at least 90% by volume, most preferably at least 95% by volume. Other possible carrier gases may be selected from carbon dioxide, argon, xenon, krypton, neon, helium, sulfurhexafluoride. Any mixture of carrier gases may be used. The carrier gas may also become loaded with water and/or acrylic acid vapors.

The gas velocity is preferably adjusted such that the flow in the reaction zone is directed, for example no convection currents opposed to the general flow direction are present, and is preferably from 0.1 to 2.5 m/s, more preferably from 0.3 to 1.5 m/s, even more preferably from 0.5 to 1.2 m/s, most preferably from 0.7 to 0.9 m/s.

The gas entrance temperature, i.e. the temperature with which the gas enters the reaction zone, is preferably from 160 to 200° C., more preferably from 165 to 195° C., even more preferably from 170 to 190° C., most preferably from 175 to 185° C.

The steam content of the gas that enters the reaction zone is preferably from 0.01 to 0.15 kg per kg dry gas, more preferably from 0.02 to 0.12 kg per kg dry gas, most preferably from 0.03 to 0.10 kg per kg dry gas.

The gas entrance temperature is controlled in such a way that the gas exit temperature, i.e. the temperature with which the gas leaves the reaction zone, is less than 150° C., preferably from 90 to 140° C., more preferably from 100 to 130° C., even more preferably from 105 to 125° C., most preferably from 110 to 120° C.

The steam content of the gas that leaves the reaction zone is preferably from 0.02 to 0.30 kg per kg dry gas, more from 0.04 to 0.28 kg per kg dry gas, most from 0.05 to 0.25 kg per kg dry gas.

The water-absorbent polymer particles can be divided into three categories: water-absorbent polymer particles of Type 1 are particles with one cavity, water-absorbent polymer particles of Type 2 are particles with more than one cavity, and water-absorbent polymer particles of Type 3 are solid particles with no visible cavity. Type 1 particles are represented by hollow-spheres, Type 2 particles are represented by spherical closed cell sponges, and Type 3 particles are represented by solid spheres. Type 2 or Type 3 particles or mixtures thereof with little or no Type 1 particles are preferred.

The morphology of the water-absorbent polymer particles can be controlled by the reaction conditions during polymerization. Water-absorbent polymer particles having a high amount of particles with one cavity (Type 1) can be prepared by using low gas velocities and high gas exit temperatures. Water-absorbent polymer particles having a high amount of particles with more than one cavity (Type 2) can be prepared by using high gas velocities and low gas exit temperatures.

Water-absorbent polymer particles having no cavity (Type 3) and water-absorbent polymer particles having more than one cavity (Type 2) show an improved mechanical stability compared with water-absorbent polymer particles having only one cavity (Type 1).

As a particular advantage round shaped particles have no edges that can easily be broken by processing stress in diaper production and during swelling in aqueous liquid there are no breakpoints on the surface that could lead to loss of mechanical strength.

The reaction can be carried out under elevated pressure or under reduced pressure, preferably from 1 to 100 mbar below ambient pressure, more preferably from 1.5 to 50 mbar below ambient pressure, most preferably from 2 to 10 mbar below ambient pressure. The reaction off-gas, i.e. the gas leaving the reaction zone, may be cooled in a heat exchanger. This condenses water and unconverted monomer a). The reaction off-gas can then be reheated at least partly and recycled into the reaction zone as cycle gas. A portion of the reaction off-gas can be discharged and replaced by fresh gas, in which case water and unconverted monomers a) present in the reaction off-gas can be removed and recycled.

Particularly preference is given to a thermally integrated system, i.e. a portion of the waste heat in the cooling of the off-gas is used to heat the cycle gas.

The reactors can be trace-heated. In this case, the trace heating is adjusted such that the wall temperature is at least 5° C. above the internal surface temperature and condensation on the surfaces is reliably prevented.

Thermal Posttreatment

The water-absorbent polymer particles may be thermal posttreated for adjusting the content of residual monomers to the desired value.

Generally the level of residual monomers can be influenced by process parameter settings, for example; the temperature of posttreatment of the water-absorbent particles. The residual monomers can be removed better at relatively high temperatures and relatively long residence times. What is important here is that the water-absorbent polymer particles are not too dry. In the case of excessively dry particles, the residual monomers decrease only insignificantly. Too high a water content increases the caking tendency of the water-absorbent polymer particles.

The thermal posttreatment can be done in a fluidized bed. In a preferred embodiment of the present invention an internal fluidized bed is used. An internal fluidized bed means that the product of the dropletization polymerization is accumulated in a fluidized bed below the reaction zone.

In the fluidized state, the kinetic energy of the polymer particles is greater than the cohesion or adhesion potential between the polymer particles.

The fluidized state can be achieved by a fluidized bed. In this bed, there is upward flow toward the water-absorbing polymer particles, so that the particles form a fluidized bed. The height of the fluidized bed is adjusted by gas rate and gas velocity, i.e. via the pressure drop of the fluidized bed (kinetic energy of the gas).

The velocity of the gas stream in the fluidized bed is preferably from 0.3 to 2.5 m/s, more preferably from 0.4 to 2.0 m/s, most preferably from 0.5 to 1.5 m/s.

The pressure drop over the bottom of the internal fluidized bed is preferably from 1 to 100 mbar, more preferably from 3 to 50 mbar, most preferably from 5 to 25 mbar.

The moisture content of the water-absorbent polymer particles at the end of the thermal posttreatment is preferably from 1 to 20% by weight, more preferably from 2 to 15% by weight, even more preferably from 3 to 12% by weight, most preferably 5 to 8% by weight. The temperature of the water-absorbent polymer particles during the thermal posttreatment is from 20 to 140° C., preferably from 40 to 110° C., more preferably from 50 to 105° C., most preferably from 60 to 100° C.

The average residence time in the internal fluidized bed is from 10 to 300 minutes, preferably from 60 to 270 minutes, more preferably from 40 to 250 minutes, most preferably from 120 to 240 minutes.

The condition of the fluidized bed can be adjusted for reducing the amount of residual monomers of the water-absorbent polymers leaving the fluidized bed. The amount of residual monomers can be reduced to levels below 0.1% by weight by a thermal posttreatment using additional steam.

The steam content of the gas is preferably from 0.005 to 0.25 kg per kg of dry gas, more preferably from 0.01 to 0.2 kg per kg of dry gas, most preferably from 0.02 to 0.15 kg per kg of dry gas.

By using additional steam the condition of the fluidized bed can be adjusted that the amount of residual monomers of the water-absorbent polymers leaving the fluidized bed is from 0.03 to 15% by weight, preferably from 0.05 to 12% by weight, more preferably from 0.1 to 10% by weight, even more preferably from 0.15 to 7.5% by weight most preferably from 0.2 to 5% by weight, even most preferably from 0.25 to 2.5% by weight.

The level of residual monomers in the water-absorbent polymer has in important impact on the properties of the later formed surface-postcrosslinked water-absorbent polymer particles. That means that very low levels of residual monomers must be avoided.

It is preferred that the thermal posttreatment is completely or at least partially done in an external fluidized bed. The operating conditions of the external fluidized bed are within the scope for the internal fluidized bed as described above.

It is alternatively preferred that the thermal posttreatment is done in an external mixer with moving mixing tools as e.g. described in WO 2011/117215 A1, preferably horizontal mixers, such as screw mixers, disk mixers, screw belt mixers and paddle mixers. Suitable mixers are, for example, Becker shovel mixers (Gebr. Lödige Maschinenbau GmbH; Paderborn; Germany), Nara paddle mixers (NARA Machinery Europe; Frechen; Germany), Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; U.S.A.) and Ruberg continuous flow mixers (Gebrüder Ruberg GmbH & Co KG, Nieheim, Germany). Ruberg continuous flow mixers, Becker shovel mixers and Pflugschar® plowshare mixers are preferred.

The thermal posttreatment can be done in a discontinuous external mixer or a continuous external mixer.

The amount of gas to be used in the discontinuous external mixer is preferably from 0.01 to 5 Nm$^3$/h, more preferably from 0.05 to 2 Nm$^3$/h, most preferably from 0.1 to 0.5 Nm$^3$/h, based in each case on kg water-absorbent polymer particles.

The amount of gas to be used in the continuous external mixer is preferably from 0.01 to 5 Nm$^3$/h, more preferably from 0.05 to 2 Nm$^3$/h, most preferably from 0.1 to 0.5 Nm$^3$/h, based in each case on kg/h throughput of water-absorbent polymer particles.

The other constituents of the gas are preferably nitrogen, carbon dioxide, argon, xenon, krypton, neon, helium, air or air/nitrogen mixtures, more preferably nitrogen or air/nitrogen mixtures comprising less than 10% by volume of oxygen. Oxygen may cause discoloration.

The morphology of the water-absorbent polymer particles can also be controlled by the reaction conditions during thermal posttreatment. Water-absorbent polymer particles having a high amount of particles with one cavity (Type 1) can be prepared by using high product temperatures and short residence times. Water-absorbent polymer particles having a high amount of particles with more than one cavity (Type 2) can be prepared by using low product temperatures and long residence times.

Surface-Postcrosslinking

Polymer particles can be surface-postcrosslinked for further improvement of the properties.

Surface-postcrosslinkers are compounds which comprise groups which can form at least two covalent bonds with the carboxylate groups of the polymer particles. Suitable compounds are, for example, polyfunctional amines, polyfunctional amidoamines, polyfunctional epoxides, as described in EP 0 083 022 A2, EP 0 543 303 A1 and EP 0 937 736 A2, di- or polyfunctional alcohols as described in DE 33 14 019 A1, DE 35 23 617 A1 and EP 0 450 922 A2, or β-hydroxyalkylamides, as described in DE 102 04 938 A1 and U.S. Pat. No. 6,239,230. Also ethyleneoxide, aziridine, glycidol, oxetane and its derivatives may be used.

Polyvinylamine, polyamidoamines and polyvinylalcohols are examples of multifunctional polymeric surface-postcrosslinkers.

In addition, DE 40 20 780 C1 describes alkylene carbonates, DE 198 07 502 A1 describes 1,3-oxazolidin-2-one and its derivatives such as 2-hydroxyethyl-1,3-oxazolidin-2-one, DE 198 07 992 C1 describes bis- and poly-1,3-oxazolidin-2-ones, EP 0 999 238 A1 describes bis- and poly-1,3-oxazolidines, DE 198 54 573 A1 describes 2-oxotetrahydro-1,3-oxazine and its derivatives, DE 198 54 574 A1 describes N-acyl-1,3-oxazolidin-2-ones, DE 102 04 937 A1 describes cyclic ureas, DE 103 34 584 A1 describes bicyclic amide acetals, EP 1 199 327 A2 describes oxetanes and cyclic ureas, and WO 2003/31482 A1 describes morpholine-2,3-dione and its derivatives, as suitable surface-postcrosslinkers.

In addition, it is also possible to use surface-postcrosslinkers which comprise additional polymerizable ethylenically unsaturated groups e.g. 1,3,2-dioxathiolane, as e.g. described in DE 37 13 601 A1.

The at least one surface-postcrosslinker is selected from alkylene carbonates, 1,3-oxazolidin-2-ones, bis- and poly-1,3-oxazolidin-2-ones, bis- and poly-1,3-oxazolidines, 2-oxotetrahydro-1,3-oxazines, N-acyl-1,3-oxazolidin-2-ones, cyclic ureas, bicyclic amide acetals, oxetanes and morpholine-2,3-diones. Suitable surface-postcrosslinkers are ethylene carbonate, 3-methyl-1,3-oxazolidin-2-one, 3-methyl-3-oxethanmethanol, 1,3-oxazolidin-2-one, 3-(2-hydroxyethyl)-1,3-oxazolidin-2-one, 1,3-dioxan-2-one or a mixture thereof.

It is also possible to use any suitable mixture of surface-postcrosslinkers. It is particularly favorable to use mixtures of 1,3-dioxolan-2-on (ethylene carbonate) and 1,3-oxazolidin-2-ones. Such mixtures are obtainable by mixing and partly reacting of 1,3-dioxolan-2-on (ethylene carbonate) with the corresponding 2-amino-alcohol (e.g. 2-aminoethanol) and may comprise ethylene glycol from the reaction.

It is preferred that at least one alkylene carbonate is used as surface-postcrosslinker. Suitable alkylene carbonates are 1,3-dioxolan-2-on (ethylene carbonate), 4-methyl-1,3-dioxolan-2-on (propylene carbonate), 4,5-dimethyl-1,3-dioxolan-2-on, 4,4-dimethyl-1,3-dioxolan-2-on, 4-ethyl-1,3-dioxolan-2-on, 4-hydroxymethyl-1,3-dioxolan-2-on (glycerine carbonate), 1,3-dioxane-2-on (trimethylene carbonate), 4-methyl-1,3-dioxane-2-on, 4,6-dimethyl-1,3-dioxane-2-on and 1,3-dioxepan-2-on, preferably 1,3-dioxolan-2-on (ethylene carbonate) and 1,3-dioxane-2-on (trimethylene carbonate), most preferably 1,3-dioxolan-2-on (ethylene carbonate).

The amount of surface-postcrosslinker is preferably from 0.1 to 10% by weight, more preferably from 0.5 to 7.5% by weight, most preferably from 1 to 5% by weight, based in each case on the polymer.

The content of residual monomers in the water-absorbent polymer particles prior to the coating with the surface-postcrosslinker is in the range from 0.03 to 15% by weight, preferably from 0.05 to 12% by weight, more preferably from 0.1 to 10% by weight, even more preferably from 0.15 to 7.5% by weight, most preferably from 0.2 to 5% by weight, even most preferably from 0.25 to 2.5% by weight.

The moisture content of the water-absorbent polymer particles prior to the thermal surface-postcrosslinking is preferably from 1 to 20% by weight, more preferably from 2 to 15% by weight, most preferably from 3 to 10% by weight.

Polyvalent cations can be applied to the particle surface in addition to the surface-postcrosslinkers before, during or after the thermal surface-postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium, and mixtures thereof. Possible counterions are chloride, bromide, sulfate, hydrogensulfate, methanesulfate, carbonate, hydrogencarbonate, nitrate, hydroxide, phosphate, hydrogenphosphate, dihydrogenphosphate, glycophosphate and carboxylate, such as acetate, glycolate, tartrate, formiate, propionate, 3-hydroxypropionate, lactamide and lactate, and mixtures thereof. Aluminum sulfate, aluminum acetate, and aluminum lactate are preferred. Aluminum lactate is more preferred. Using the inventive process in combination with the use of aluminum lactate, water-absorbent polymer particles having an extremely high total liquid uptake at lower centrifuge retention capacities (CRC) can be prepared.

Apart from metal salts, it is also possible to use polyamines and/or polymeric amines as polyvalent cations. A single metal salt can be used as well as any mixture of the metal salts and/or the polyamines above.

Preferred polyvalent cations and corresponding anions are disclosed in WO 2012/045705 A1 and are expressly incorporated herein by reference. Preferred polyvinylamines are disclosed in WO 2004/024816 A1 and are expressly incorporated herein by reference.

The amount of polyvalent cation used is, for example, from 0.001 to 1.5% by weight, preferably from 0.005 to 1% by weight, more preferably from 0.02 to 0.8% by weight, based in each case on the polymer.

The addition of the polyvalent metal cation can take place prior, after, or cocurrently with the surface-postcrosslinking. Depending on the formulation and operating conditions employed it is possible to obtain a homogeneous surface coating and distribution of the polyvalent cation or an inhomogeneous typically spotty coating. Both types of coatings and any mixes between them are useful within the scope of the present invention.

The surface-postcrosslinking is typically performed in such a way that a solution of the surface-postcrosslinker is sprayed onto the hydrogel or the dry polymer particles. After the spraying, the polymer particles coated with the surface-postcrosslinker are dried thermally and cooled.

The spraying of a solution of the surface-postcrosslinker is preferably performed in mixers with moving mixing tools, such as screw mixers, disk mixers and paddle mixers. Suitable mixers are, for example, vertical Schugi Flexomix® mixers (Hosokawa Micron BV; Doetinchem; the Netherlands), Turbolizers® mixers (Hosokawa Micron BV; Doetinchem; the Netherlands), horizontal Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; US) and Ruberg continuous flow mixers (Gebrüder Ruberg GmbH & Co KG, Nieheim, Germany). Ruberg continuous flow mixers and horizontal Pflugschar® plowshare mixers are preferred. The surface-postcrosslinker solution can also be sprayed into a fluidized bed.

The solution of the surface-postcrosslinker can also be sprayed on the water-absorbent polymer particles during the thermal posttreatment. In such case the surface-postcrosslinker can be added as one portion or in several portions along the axis of thermal posttreatment mixer. In one embodiment it is preferred to add the surface-postcrosslinker at the end of the thermal posttreatment step. As a particular advantage of adding the solution of the surface-postcrosslinker during the thermal posttreatment step it may be possible to eliminate or reduce the technical effort for a separate surface-postcrosslinker addition mixer.

The surface-postcrosslinkers are typically used as an aqueous solution. The addition of nonaqueous solvent can be used to improve surface wetting and to adjust the penetration depth of the surface-postcrosslinker into the polymer particles.

The thermal surface-postcrosslinking is preferably carried out in contact dryers, more preferably paddle dryers, most preferably disk dryers. Suitable driers are, for example, Hosokawa Bepex® horizontal paddle driers (Hosokawa Micron GmbH; Leingarten; Germany), Hosokawa Bepex® disk driers (Hosokawa Micron GmbH; Leingarten; Germany), Holo-Flite® dryers (Metso Minerals Industries Inc.; Danville; U.S.A.) and Nara paddle driers (NARA Machinery Europe; Frechen; Germany). Moreover, it is also possible to use fluidized bed dryers. In the latter case the reaction times may be shorter compared to other embodiments.

When a horizontal dryer is used then it is often advantageous to set the dryer up with an inclined angle of a few degrees vs. the earth surface in order to impart proper product flow through the dryer. The angle can be fixed or may be adjustable and is typically between 0 to 10 degrees, preferably 1 to 6 degrees, most preferably 2 to 4 degrees.

A contact dryer can be used that has two different heating zones in one apparatus. For example Nara paddle driers are available with just one heated zone or alternatively with two heated zones. The advantage of using a two or more heated zone dryer is that different phases of the thermal post-treatment and/or of the post-surface-crosslinking can be combined.

It is possible to use a contact dryer with a hot first heating zone which is followed by a temperature holding zone in the same dryer. This set up allows a quick rise of the product temperature and evaporation of surplus liquid in the first heating zone, whereas the rest of the dryer is just holding the product temperature stable to complete the reaction.

It is also possible to use a contact dryer with a warm first heating zone which is then followed by a hot heating zone. In the first warm zone the thermal post-treatment is affected or completed whereas the surface-postcrosslinking takes place in the subsequential hot zone.

Typically a paddle heater with just one temperature zone is employed.

A person skilled in the art will depending on the desired finished product properties and the available base polymer qualities from the polymerization step choose any one of these set ups.

The thermal surface-postcrosslinking can be effected in the mixer itself, by heating the jacket, blowing in warm air or steam. Equally suitable is a downstream dryer, for example a shelf dryer, a rotary tube oven or a heatable screw. It is particularly advantageous to mix and dry in a fluidized bed dryer.

Preferred thermal surface-postcrosslinking temperatures are usually in the range of 100-195° C., mostly in the range of 100 to 180° C., preferably from 120 to 170° C., more preferably from 130 to 165° C., most preferably from 140 to 160° C. The preferred residence time at this temperature in the reaction mixer or dryer is preferably at least 5 minutes, more preferably at least 20 minutes, most preferably at least 40 minutes, and typically at most 120 minutes.

It is preferable to cool the polymer particles after thermal surface-postcrosslinking. The cooling is preferably carried out in contact coolers, more preferably paddle coolers, most preferably disk coolers. Suitable coolers are, for example, Hosokawa Bepex® horizontal paddle coolers (Hosokawa Micron GmbH; Leingarten; Germany), Hosokawa Bepex® disk coolers (Hosokawa Micron GmbH; Leingarten; Germany), Holo-Flite® coolers (Metso Minerals Industries Inc.; Danville; U.S.A.) and Nara paddle coolers (NARA Machinery Europe; Frechen; Germany). Moreover, it is also possible to use fluidized bed coolers.

In the cooler the polymer particles are cooled to temperatures in the range from 20 to 150° C., preferably from 40 to 120° C., more preferably from 60 to 100° C., most preferably from 70 to 90° C. Cooling using warm water is preferred, especially when contact coolers are used.

Coating

To improve the properties, the water-absorbent polymer particles can be coated and/or optionally moistened. The internal fluidized bed, the external fluidized bed and/or the external mixer used for the thermal posttreatment and/or a separate coater (mixer) can be used for coating of the water-absorbent polymer particles. Further, the cooler and/or a separate coater (mixer) can be used for coating/moistening of the surface-postcrosslinked water-absorbent polymer particles. Suitable coatings for controlling the acquisition behavior and improving the permeability (SFC or GBP) are, for example, inorganic inert substances, such as water-insoluble metal salts, organic polymers, cationic polymers, anionic polymers and polyvalent metal cations. Suitable coatings for improving the color stability are, for example reducing agents, chelating agents and anti-oxidants. Suitable coatings for dust binding are, for example, polyols. Suitable coatings against the undesired caking tendency of the polymer particles are, for example, fumed silica, such as Aerosil® 200, and surfactants, such as Span® 20 and Plantacare® 818 UP. Preferred coatings are aluminium dihydroxy monoacetate, aluminium sulfate, aluminium lactate, aluminium 3-hydroxypropionate, zirconium acetate, citric acid or its water soluble salts, di- and monophosphoric acid or their water soluble salts, Blancolen®, Brüggolite® FF7, Cublen®, Span® 20 and Plantacare® 818 UP.

If salts of the above acids are used instead of the free acids then the preferred salts are alkali-metal, earth alkali metal, aluminum, zirconium, titanium, zinc and ammonium salts.

Under the trade name Cublen® (Zschimmer & Schwarz Mohsdorf GmbH & Co KG; Burgstädt; Germany) the following acids and/or their alkali metal salts (preferably Na and K-salts) are available and may be used within the scope of the present invention for example to impart color-stability to the finished product:

1-Hydroxyethane-1,1-diphosphonic acid, Amino-tris (methylene phosphonic acid), Ethylenediamine-tetra(methylene phosphonic acid), Diethylenetriamine-penta(methylene phosphonic acid), Hexamethylene diamine-tetra(methylenephosphonic acid), Hydroxyethyl-amino-di(methylene phosphonic acid), 2-Phosphonobutane-1,2,4-tricarboxylic acid, Bis(hexamethylenetriamine penta (methylene phosphonic acid).

Most preferably 1-Hydroxyethane-1,1-diphosphonic acid or its salts with sodium, potassium, or ammonium are employed. Any mixture of the above Cublenes® can be used.

Alternatively, any of the chelating agents described before for use in the polymerization can be coated onto the finished product.

Suitable inorganic inert substances are silicates such as montmorillonite, kaolinite and talc, zeolites, activated carbons, polysilicic acids, magnesium carbonate, calcium carbonate, calcium phosphate, aluminum phosphate, barium sulfate, aluminum oxide, titanium dioxide and iron (II) oxide. Preference is given to using polysilicic acids, which are divided between precipitated silicas and fumed silicas according to their mode of preparation. The two variants are commercially available under the names Silica FK, Sipernat®, Wessalon® (precipitated silicas) and Aerosil® (fumed silicas) respectively. The inorganic inert substances may be used as dispersion in an aqueous or water-miscible dispersant or in substance.

When the water-absorbent polymer particles are coated with inorganic inert substances, the amount of inorganic inert substances used, based on the water-absorbent polymer particles, is preferably from 0.05 to 5% by weight, more preferably from 0.1 to 1.5% by weight, most preferably from 0.3 to 1% by weight.

Suitable organic polymers are polyalkyl methacrylates or thermoplastics such as polyvinyl chloride, waxes based on polyethylene, polypropylene, polyamides or polytetrafluoroethylene. Other examples are styrene-isoprene-styrene block-copolymers or styrenebutadiene-styrene block-copolymers. Another example are silanole-group bearing polyvinylalcoholes available under the trade name Poval® R (Kuraray Europe GmbH; Frankfurt; Germany).

Suitable cationic polymers are polyalkylenepolyamines, cationic derivatives of polyacrylamides, polyethyleneimines and polyquaternary amines.

Polyquaternary amines are, for example, condensation products of hexamethylenediamine, dimethylamine and epichlorohydrin, condensation products of dimethylamine and epichlorohydrin, copolymers of hydroxyethylcellulose and diallyldimethylammonium chloride, copolymers of acrylamide and α-methacryloyloxyethyltrimethylammonium chloride, condensation products of hydroxyethylcellulose, epichlorohydrin and trimethylamine, homopolymers of diallyldimethylammonium chloride and addition products of epichlorohydrin to amidoamines. In addition, polyquaternary amines can be obtained by reacting dimethyl sulfate with polymers such as polyethyleneimines, copolymers of vinylpyrrolidone and dimethylaminoethyl methacrylate or copolymers of ethyl methacrylate and diethylaminoethyl methacrylate. The polyquaternary amines are available within a wide molecular weight range.

However, it is also possible to generate the cationic polymers on the particle surface, either through reagents which can form a network with themselves, such as addition products of epichlorohydrin to polyamidoamines, or through the application of cationic polymers which can react with an added crosslinker, such as polyamines or polyimines in combination with polyepoxides, polyfunctional esters, polyfunctional acids or polyfunctional (meth)acrylates.

It is possible to use all polyfunctional amines having primary or secondary amino groups, such as polyethyleneimine, polyallylamine and polylysine. The liquid sprayed by the process according to the invention preferably comprises at least one polyamine, for example polyvinylamine or a partially hydrolyzed polyvinylformamide.

The cationic polymers may be used as a solution in an aqueous or water-miscible solvent, as dispersion in an aqueous or water-miscible dispersant or in substance.

When the water-absorbent polymer particles are coated with a cationic polymer, the use amount of cationic polymer based on the water-absorbent polymer particles is usually not less than 0.001% by weight, typically not less than 0.01% by weight, preferably from 0.1 to 15% by weight, more preferably from 0.5 to 10% by weight, most preferably from 1 to 5% by weight.

Suitable anionic polymers are polyacrylates (in acidic form or partially neutralized as salt), copolymers of acrylic acid and maleic acid available under the trade name Sokalan® (BASF SE; Ludwigshafen; Germany), and polyvinylalcohols with built in ionic charges available under the trade name Poval® K (Kuraray Europe GmbH; Frankfurt; Germany).

Suitable polyvalent metal cations are $Mg^{2+}$, $Ca^{2+}$, $Al^{3+}$, $Sc^{3+}$, $Ti^{4+}$, $Mn^{2+}$, $Fe^{2+/3+}$, $Co^{2+}$, $Ni^{2+}$, $Ce^{2+}$, $Zn^{2+}$, $Y^{3+}$, $Zr^{4+}$, $Ag^+$, $La^{3+}$, $Ce^{4+}$, $Hf^{4+}$ and $Au^{+/3+}$; preferred metal cations are $Mg^{2+}$, $Ca^{2+}$, $Al^{3+}$, $Ti^{4+}$, $Zr^{4+}$ and $La^{3+}$; particularly preferred metal cations are $Al^{3+}$, $Ti^{4+}$ and $Zr^{4+}$. The metal cations may be used either alone or in a mixture with one another. Suitable metal salts of the metal cations mentioned are all of those which have a sufficient solubility in the solvent to be used. Particularly suitable metal salts have weakly complexing anions, such as chloride, hydroxide, carbonate, acetate, formiate, propionate, nitrate, sulfate and methanesulfate. The metal salts are preferably used as a solution or as a stable aqueous colloidal dispersion. The solvents used for the metal salts may be water, alcohols, ethylenecarbonate, propylenecarbonate, dimethylformamide, dimethyl sulfoxide and mixtures thereof. Particularly preference is given to water and water/alcohol mixtures, such as water/methanol, water/isopropanol, water/1,3-propanediole, water/1,2-propandiole/1,4-butanediole or water/propylene glycol.

When the water-absorbent polymer particles are coated with a polyvalent metal cation, the amount of polyvalent metal cation used, based on the water-absorbent polymer particles, is preferably from 0.05 to 5% by weight, more preferably from 0.1 to 1.5% by weight, most preferably from 0.3 to 1% by weight.

Suitable reducing agents are, for example, sodium sulfite, sodium hydrogensulfite (sodium bisulfite), sodium dithionite, sulfinic acids and salts thereof, ascorbic acid, sodium hypophosphite, sodium phosphite, and phosphinic acids and salts thereof. Preference is given, however, to salts of hypophosphorous acid, for example sodium hypophosphite, salts of sulfinic acids, for example the disodium salt of 2-hydroxy-2-sulfinatoacetic acid, and addition products of aldehydes, for example the disodium salt of 2-hydroxy-2-sulfonatoacetic acid. The reducing agent used can be, however, a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany). Also useful is the purified 2-hydroxy-2-sulfonatoacetic acid and its sodium salts, available under the trade name Blancolen® from the same company.

The reducing agents are typically used in the form of a solution in a suitable solvent, preferably water. The reducing agent may be used as a pure substance or any mixture of the above reducing agents may be used.

When the water-absorbent polymer particles are coated with a reducing agent, the amount of reducing agent used, based on the water-absorbent polymer particles, is preferably from 0.01 to 5% by weight, more preferably from 0.05 to 2% by weight, most preferably from 0.1 to 1% by weight.

Suitable polyols are polyethylene glycols having a molecular weight of from 400 to 20000 g/mol, polyglycerol, 3- to 100-tuply ethoxylated polyols, such as trimethylolpropane, glycerol, sorbitol, mannitol, inositol, pentaerythritol and neopentyl glycol. Particularly suitable polyols are 7- to 20-tuply ethoxylated glycerol or trimethylolpropane, for example Polyol TP 70® (Perstorp AB, Perstorp, Sweden). The latter have the advantage in particular that they lower the surface tension of an aqueous extract of the water-absorbent polymer particles only insignificantly. The polyols are preferably used as a solution in aqueous or water-miscible solvents.

The polyol can be added before, during, or after surface-crosslinking. Preferably it is added after surface-cross linking. Any mixture of the above listed poyols may be used.

When the water-absorbent polymer particles are coated with a polyol, the use amount of polyol, based on the water-absorbent polymer particles, is preferably from 0.005 to 2% by weight, more preferably from 0.01 to 1% by weight, most preferably from 0.05 to 0.5% by weight.

The coating is preferably performed in mixers with moving mixing tools, such as screw mixers, disk mixers, paddle mixers and drum coater. Suitable mixers are, for example, horizontal Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; US) and Ruberg continuous flow mixers (Gebrüder Ruberg GmbH & Co KG, Nieheim, Germany). Moreover, it is also possible to use a fluidized bed for mixing.

Agglomeration

The water-absorbent polymer particles can further selectivily be agglomerated. The agglomeration can take place after the polymerization, the thermal posttreatment, the thermal surface-postcrosslinking or the coating.

Useful agglomeration assistants include water and water-miscible organic solvents, such as alcohols, tetrahydrofuran and acetone; water-soluble polymers can be used in addition. Examples are water-soluble polymeric binders. Binders may include, but are not limited to: carboxymethyl cellulose, starch, dextran, polyvinylamine, polyethyleneimine, polyvinylalcohol, polyacrylic acid and its salts, polyethylene oxide, polyethyleneglycol and chitosan.

For agglomeration a solution comprising the agglomeration assistant is sprayed onto the water-absorbing polymeric particles. The spraying with the solution can, for example, be carried out in mixers having moving mixing implements, such as screw mixers, paddle mixers, disk mixers, plowshare mixers and shovel mixers. Useful mixers include for example Lödige® mixers, Bepex® mixers, Nauta® mixers, Processall® mixers and Schugi® mixers. Vertical mixers are preferred. Fluidized bed apparatuses are particularly preferred.

Combination of Thermal Posttreatment, Surface-Postcrosslinking and Optionally Coating It is preferred that the steps of thermal posttreatment and thermal surface-postcrosslinking are combined in one process step. Such combination allows the use of low cost equipment and moreover the process can be run at low temperatures, this is cost-efficient and avoids discoloration and loss of performance properties of the finished product by thermal degradation.

The mixer may be selected from any of the equipment options cited in the thermal posttreatment section. Ruberg continuous flow mixers, Becker shovel mixers and Pflugschar® plowshare mixers are preferred.

It is particularly preferred that the surface-postcrosslinking solution is sprayed onto the water-absorbent polymer particles under agitation.

Following the thermal posttreatment/surface-postcrosslinking the water-absorbent polymer particles are dried to the desired moisture level and for this step any dryer cited in the surface-postcrosslinking section may be selected. However, as only drying needs to be accomplished in this particularly preferred embodiment it is possible to use simple and low cost heated contact dryers like a heated screw dryer, for example a Holo-Flite® dryer (Metso Minerals Industries Inc.; Danville; U.S.A.). Alternatively a fluidized bed may be used. In cases where the product needs to be dried with a predetermined and narrow residence time it is possible to use torus disc dryers or paddle dryers, for example a Nara paddle dryer (NARA Machinery Europe; Frechen; Germany).

In a preferred embodiment of the present invention, polyvalent cations cited in the surface-postcrosslinking section are applied to the particle surface before, during or after addition of the surface-postcrosslinker by using different addition points along the axis of a horizontal mixer.

It is very particularly preferred that the steps of thermal post-treatment, surface-postcrosslinking, and coating are combined in one process step. Suitable coatings are cationic polymers, surfactants, and inorganic inert substances that are cited in the coating section. The coating agent can be applied to the particle surface before, during or after addition of the surface-postcrosslinker also by using different addition points along the axis of a horizontal mixer.

The polyvalent cations and/or the cationic polymers can act as additional scavengers for residual surface-postcrosslinkers. It is preferred that the surface-postcrosslinkers are added prior to the polyvalent cations and/or the cationic polymers to allow the surface-postcrosslinker to react first.

The surfactants and/or the inorganic inert substances can be used to avoid sticking or caking during this process step under humid atmospheric conditions. Preferred surfactants are non-ionic and amphoteric surfactants. Preferred inorganic inert substances are precipitated silicas and fumed silcas in form of powder or dispersion.

The amount of total liquid used for preparing the solutions/dispersions is typically from 0.01% to 25% by weight, preferably from 0.5% to 12% by weight, more preferably from 2% to 7% by weight, most preferably from 3% to 6% by weight, in respect to the weight amount of water-absorbent polymer particles to be processed.

Preferred embodiments for the dropletization process are depicted in FIGS. 1 to 15.

FIG. 1: Process scheme
FIG. 2: Process scheme using dry air
FIG. 3: Arrangement of the T_outlet measurement
FIG. 4: Arrangement of the dropletizer units with 3 droplet plates
FIG. 5: Arrangement of the dropletizer units with 9 droplet plates
FIG. 6: Arrangement of the dropletizer units with 9 droplet plates
FIG. 7: Dropletizer unit (longitudinal cut)
FIG. 8: Dropletizer unit (cross sectional view)
FIG. 9: Bottom of the internal fluidized bed (top view)
FIG. 10: openings in the bottom of the internal fluidized bed
FIG. 11: Rake stirrer for the intern fluidized bed (top view)
FIG. 12: Rake stirrer for the intern fluidized bed (cross sectional view)
FIG. 13: Process scheme (surface-postcrosslinking)
FIG. 14: Process scheme (surface-postcrosslinking and coating)
FIG. 15: Contact dryer for surface-postcrosslinking The reference numerals have the following meanings:
1 Drying gas inlet pipe
2 Drying gas amount measurement
3 Gas distributor
4 Dropletizer unit(s)
4a Dropletizer unit
4b Dropletizer unit
4c Dropletizer unit
5 Reaction zone (cylindrical part of the spray dryer)
6 Cone
7 T_outlet measurement
8 Tower offgas pipe
9 Dust separation unit
10 Ventilator
11 Quench nozzles
12 Condenser column, counter current cooling
13 Heat exchanger
14 Pump
15 Pump
16 Water outlet
17 Ventilator
18 Offgas outlet
19 Nitrogen inlet
20 Heat exchanger
21 Ventilator
22 Heat exchanger
24 Water loading measurement
25 Conditioned internal fluidized bed gas
26 Internal fluidized bed product temperature measurement
27 Internal fluidized bed
28 Rotary valve
29 Sieve
30 End product
31 Static mixer
32 Static mixer
33 Initiator feed
34 Initiator feed
35 Monomer feed
36 Fine particle fraction outlet to rework
37 Gas drying unit
38 Monomer separator unit
39 Gas inlet pipe
40 Gas outlet pipe
41 Water outlet from the gas drying unit to condenser column
42 Waste water outlet
43 T_outlet measurement (average temperature out of 3 measurements around tower circumference)
45 Monomer premixed with initiator feed
46 Spray dryer tower wall
47 Dropletizer unit outer pipe
48 Dropletizer unit inner pipe
49 Dropletizer cassette
50 Teflon block
51 Valve
52 Monomer premixed with initiator feed inlet pipe connector
53 Droplet plate
54 Counter plate
55 Flow channels for temperature control water
56 Dead volume free flow channel for monomer solution
57 Dropletizer cassette stainless steel block
58 Bottom of the internal fluidized bed with four segments
59 Split openings of the segments
60 Rake stirrer
61 Prongs of the rake stirrer
62 Mixer
63 Optional coating feed
64 Postcrosslinker feed
65 Thermal dryer (surface-postcrosslinking)
66 Cooler
67 Optional coating/water feed
68 Coater
69 Coating/water feed
70 Base polymer feed
71 Discharge zone
72 Weir opening
73 Weir plate
74 Weir height 100%
75 Weir height 50%
76 Shaft
77 Discharge cone
78 Inclination angle α
79 Temperature sensors ($T_1$ to $T_6$)
80 Paddle (shaft offset 90°)

The drying gas is fed via a gas distributor (3) at the top of the spray dryer as shown in FIG. 1. The drying gas is partly recycled (drying gas loop) via a baghouse filter or cyclone unit (9) and a condenser column (12). The pressure inside the spray dryer is below ambient pressure.

Figure 3:
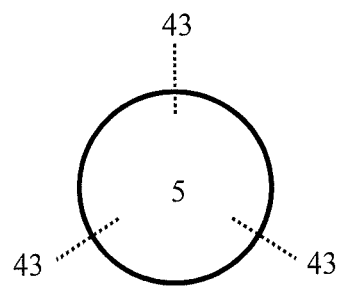

The spray dryer outlet temperature is preferably measured at three points around the circumference at the end of the cylindrical part as shown in FIG. 3. The single measurements (43) are used to calculate the average cylindrical spray dryer outlet temperature.

In one preferred embodiment a monomer separator unit (38) is used for recycling of the monomers from the condenser column (12) into the monomer feed (35). This monomer separator unit is for example especially a combination of micro-, ultra-, nanofiltration and osmose membrane units, to separate the monomer from water and polymer particles. Suitable membrane separator systems are described, for example, in the monograph "Membranen: Grundlagen, Verfahren und Industrielle Anwendungen", K. Ohlrogge and K. Ebert, Wiley-VCH, 2012 (ISBN: 978-3-527-66033-9).

The product accumulated in the internal fluidized bed (27). Conditioned internal fluidized bed gas is fed to the internal fluidized bed (27) via line (25). The relative humidity of the internal fluidized bed gas is preferably controlled by the temperature in the condensor column (12) and using the Mollier diagram.

The spray dryer offgas is filtered in a dust separation unit (9) and sent to a condenser column (12) for quenching/cooling. After dust separation (9) a recuperation heat exchanger system for preheating the gas after the condenser column (12) can be used. The dust separation unit (9) may be heat-traced on a temperature of preferably from 80 to 180° C., more preferably from 90 to 150° C., most preferably from 100 to 140° C.

Example for the dust separation unit are baghouse filter, membranes, cyclones, dust compactors and for examples described, for example, in the monographs "Staubabscheiden", F. Löffler, Georg Thieme Verlag, Stuttgart, 1988 (ISBN 978-3137122012) and "Staubabscheidung mit Schlauchfiltern und Taschenfiltern", F. Löffler, H. Dietrich and W. Flatt, Vieweg, Braunschweig, 1991 (ISBN 978-3540670629).

Most preferable are cyclones, for example, cyclones/centrifugal separators of the types ZSA/ZSB/ZSC from LTG Aktiengesellschaft and cyclone separators from Ventilatorenfabrik Oelde GmbH, Camfil Farr International and MikroPul GmbH.

Excess water is pumped out of the condenser column (12) by controlling the (constant) filling level in the condenser column (12). The water in the condenser column (12) is pumped counter-current to the gas via quench nozzles (11) and cooled by a heat exchanger (13) so that the temperature in the condenser column (12) is preferably from 40 to 71° C., more preferably from 46 to 69° C., most preferably from 49 to 65° C. and more even preferably from 51 to 60° C. The water in the condenser column (12) is set to an alkaline pH by dosing a neutralizing agent to wash out vapors of monomer a). Aqueous solution from the condenser column (12) can be sent back for preparation of the monomer solution.

The condenser column offgas may be split to the gas drying unit (37) and the conditioned internal fluidized bed gas (27).

The principle of a gas drying unit is described in the monograph "Leitfaden für Lüftungsund Klimaanlagen - Grundlagen der Thermodynamik Komponenten einer Vollklimaanlage Normen and Vorschriften", L. Keller, Oldenbourg Industrieverlag, 2009 (ISBN 978-3835631656).

As gas drying unit can be used, for example, an air gas cooling system in combination with a gas mist eliminators or droplet separator (demister), for examples, droplet vane type separator for horizontal flow (e.g. type DH 5000 from Munters AB, Sweden) or vertical flow (e.g. type DV 270 from Munters AB, Sweden). Vane type demisters remove liquid droplets from continuous gas flows by inertial impaction. As the gas carrying entrained liquid droplets moves through the sinusoidal path of a vane, the higher density liquid droplets cannot follow and as a result, at every turn of the vane blades, these liquid droplets impinge on the vane surface. Most of the droplets adhere to the vane wall. When a droplet impinges on the vane blade at the same location, coalescence occurs. The coalesced droplets then drain down due to gravity.

As air gas cooling system, any gas/gas or gas/liquid heat exchanger can be used. Preferred are sealed plate heat exchangers.

Figure 2:
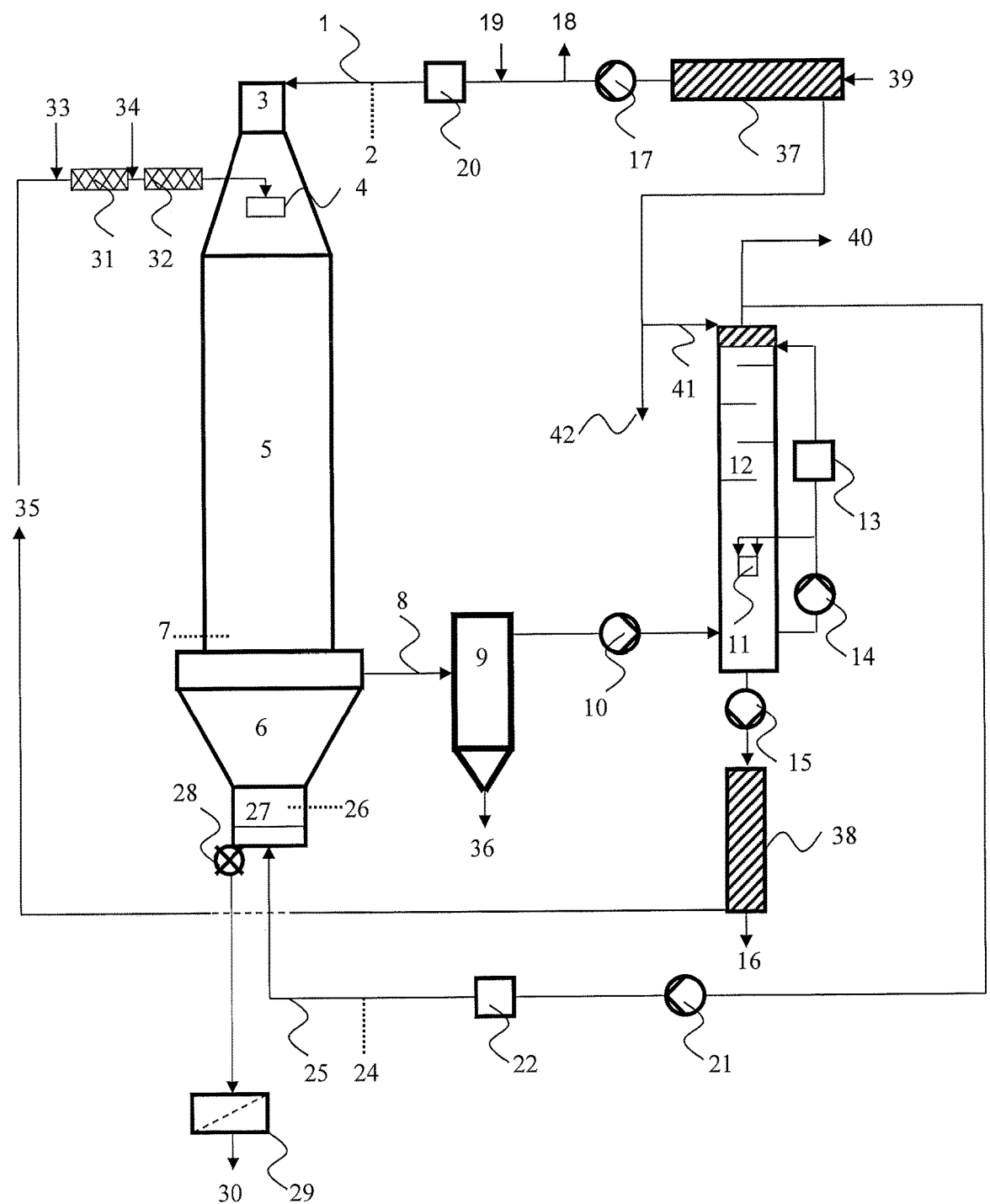

In one embodiment dry air can be used as feed for the gas distributor (3). If air used as gas, then air can be transported via air inlet pipe (39) and can be dried in the gas drying unit (37), as described before. After the condenser column (12), the air, which not used for the internal fluidized bed is transported via the outlet pipe outside (40) of the plant as shown in FIG. 2.

The water, which is condensed in the gas drying unit (37) can be partially used as wash water for the condenser column (12) or disposed.

The gas temperatures are controlled via heat exchangers (20) and (22). The hot drying gas is fed to the cocurrent spray dryer via gas distributor (3). The gas distributor (3) consists preferably of a set of plates providing a pressure drop of preferably 1 to 100 mbar, more preferably 2 to 30 mbar, most preferably 4 to 20 mbar, depending on the drying gas amount. Turbulences and/or a centrifugal velocity can also be introduced into the drying gas if desired by using gas nozzles or baffle plates.

Conditioned internal fluidized bed gas is fed to the internal fluidized bed (27) via line (25). The steam content of the fluidized bed gas can be controlled by the temperature in the condenser column (12). The product holdup in the internal fluidized bed (27) can be controlled via rotational speed of the rotary valve (28).

The amount of gas in the internal fluidized bed (27) is selected so that the particles move free and turbulent in the internal fluidized bed (27). The product height in the internal fluidized bed (27) is with gas preferably at least 10%, more preferably at least 20%, more preferably at least 30%, even more preferably at least 40% higher than without gas.

The product is discharged from the internal fluidized bed (27) via rotary valve (28). The product holdup in the internal fluidized bed (27) can be controlled via rotational speed of the rotary valve (28). The sieve (29) is used for sieving off overs/lumps.

The monomer solution is preferably prepared by mixing first monomer a) with a neutralization agent and secondly with crosslinker b). The temperature during neutralization is controlled to preferably from 5 to 60° C., more preferably from 8 to 40° C., most preferably from 10 to 30° C., by using a heat exchanger and pumping in a loop. A filter unit is preferably used in the loop after the pump. The initiators are metered into the monomer solution upstream of the dropletizer by means of static mixers (31) and (32) via lines (33) and (34) as shown in FIG. 1 and FIG. 2. Preferably a peroxide solution having a temperature of preferably from 5 to 60° C., more preferably from 10 to 50° C., most preferably from 15 to 40° C., is added via line (33) and preferably an azo initiator solution having a temperature of preferably from 2 to 30° C., more preferably from 3 to 15° C., most preferably from 4 to 8° C., is added via line (34). Each initiator is preferably pumped in a loop and dosed via control valves to each dropletizer unit. A second filter unit is preferably used after the static mixer (32). The mean residence time of the monomer solution admixed with the full initiator package in the piping before dropletization is preferably less than 60 s, more preferably less than 30 s, most preferably less than 10 s.

Figure 4:
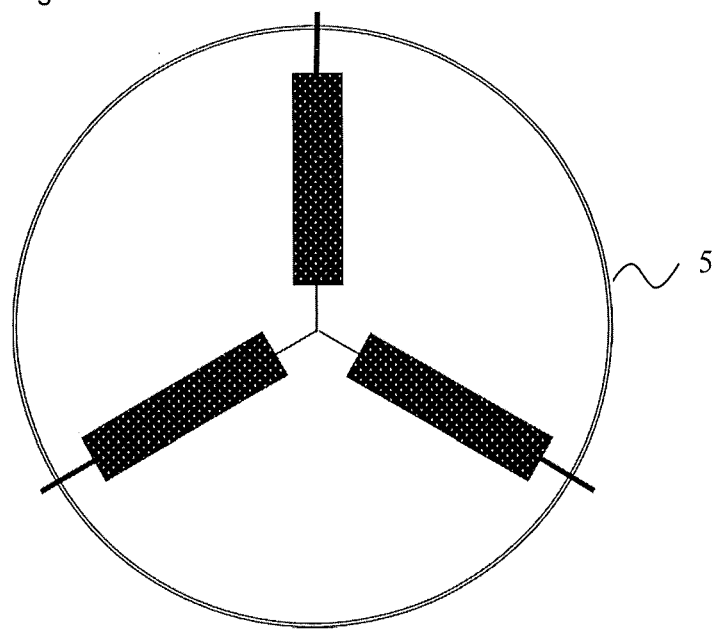

For dosing the monomer solution into the top of the spray dryer preferably three dropletizer units are used as shown in FIG. 4. However, any number of dropletizers can be used that is required to optimize the throughput of the process and the quality of the product. Hence, in the present invention at least one dropletizer is employed, and as many dropletizers as geometrically allowed may be used.

Figure 7:
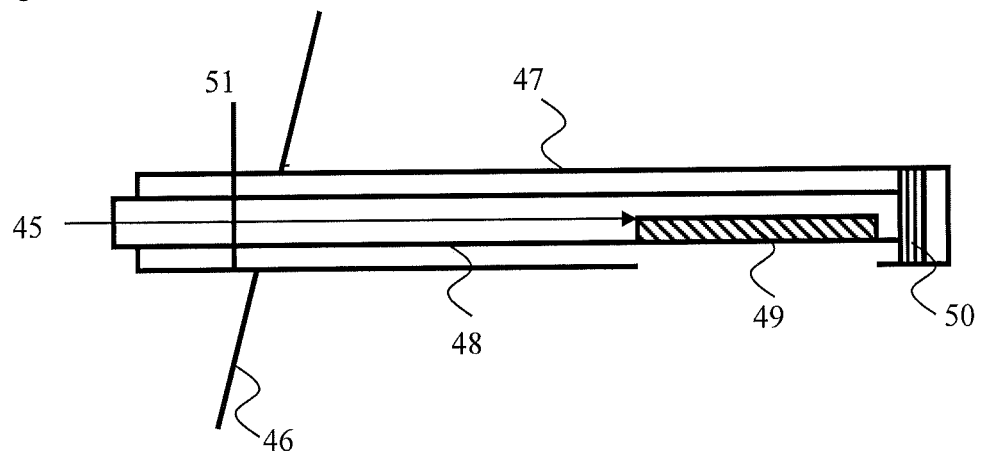

A dropletizer unit consists of an outer pipe (47) having an opening for the dropletizer cassette (49) as shown in FIG. 7. The dropletizer cassette (49) is connected with an inner pipe (48). The inner pipe (48) having a PTFE block (50) at the end as sealing can be pushed in and out of the outer pipe (51) during operation of the process for maintenance purposes.

Figure 8:
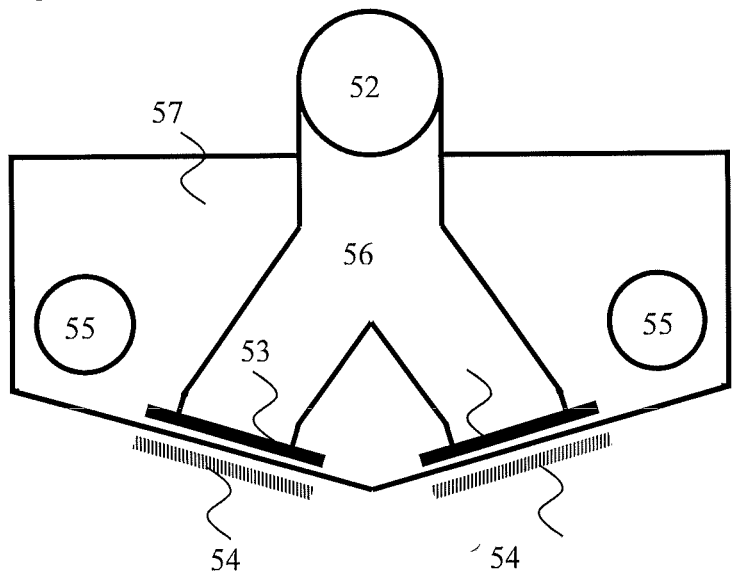

The temperature of the dropletizer cassette (57) is controlled to preferably 5 to 80° C., more preferably 10 to 70° C., most preferably 30 to 60° C., by water in flow channels (55) as shown in FIG. 8.

The dropletizer cassette has preferably from 10 to 2000 bores, more preferably from 50 to 1500 bores, most preferably from 100 to 1000 bores. The diameter of the bores size area is 1900 to 22300 µm², more preferably from 7800 to 20100 µm², most preferably from 11300 to 17700 µm². The bores can be of circular, rectangular, triangular or any other shape. Circular bores are preferred with a bore size from 50 to 170 µm, more preferably from 100 to 160 µm, most preferably from 120 to 150 µm. The ratio of bore length to bore diameter is preferably from 0.5 to 10, more preferably from 0.8 to 5, most preferably from 1 to 3. The droplet plate (53) can have a greater thickness than the bore length when using an inlet bore channel. The droplet plate (53) is preferably long and narrow as disclosed in WO 2008/086976 A1. Multiple rows of bores per droplet plate can be used, preferably from 1 to 20 rows, more preferably from 2 to 5 rows.

The dropletizer cassette (57) consists of a flow channel (56) having essential no stagnant volume for homogeneous distribution of the premixed monomer and initiator solutions and two droplet plates (53). The droplet plates (53) have an angled configuration with an angle of preferably from 1 to 90°, more preferably from 3 to 45°, most preferably from 5 to 20°. Each droplet plate (53) is preferably made of a heat and/or chemically resistant material, such as stainless steel, polyether ether ketone, polycarbonate, polyarylsulfone, such as polysulfone, or polyphenylsulfone, or fluorous polymers, such as perfluoroalkoxyethylene, polytetrafluoroethylene, polyvinylidenfluorid, ethylene-chlorotrifluoroethylene copolymers, ethylene-tetrafluoroethylene copolymers and fluorinated polyethylene. Coated droplet plates as disclosed in WO 2007/031441 A1 can also be used. The choice of material for the droplet plate is not limited except that droplet formation must work and it is preferable to use materials which do not catalyze the start of polymerization on its surface.

Figure 5:
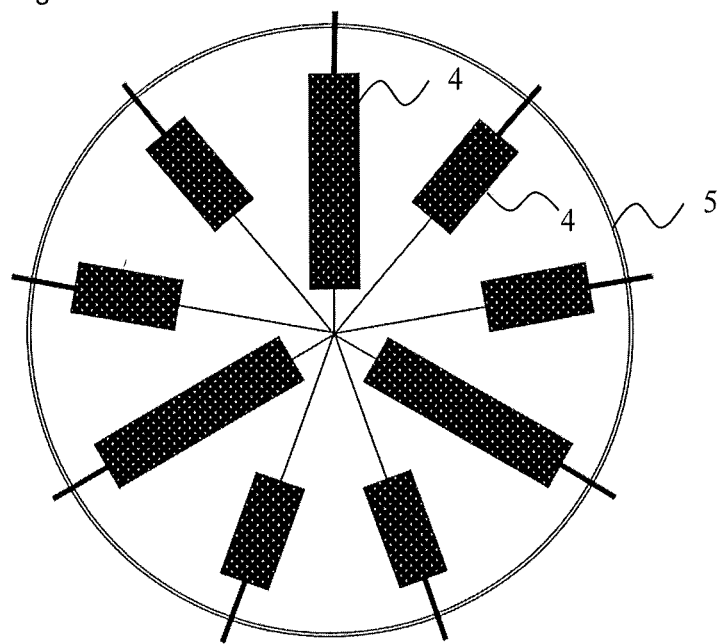
Figure 6:
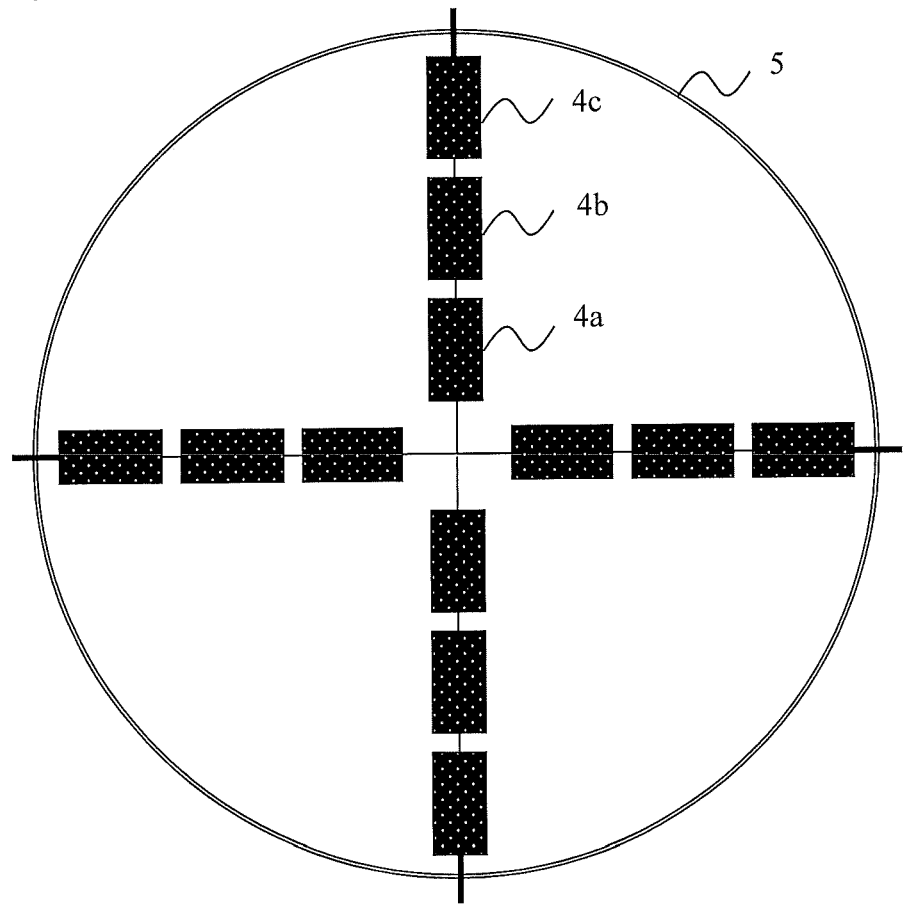

The arrangement of dropletizer cassettes is preferably rotationally symmetric or evenly distributed in the spray dryer (for example see FIGS. 3 to 5).

In a preferred embodiment the angle configuration of the droplet plate (53) is in the middle lower then outside, for example: 4a=3°, 4b=5° and 4c=8° (FIG. 5).

The throughput of monomer including initiator solutions per dropletizer unit is preferably from 10 to 4000 kg/h, more preferably from 100 to 1000 kg/h, most preferably from 200 to 600 kg/h. The throughput per bore is preferably from 0.1 to 10 kg/h, more preferably from 0.5 to 5 kg/h, most preferably from 0.7 to 2 kg/h.

The start-up of the cocurrent spray dryer (5) can be done in the following sequence:
  starting the condenser column (12),
  starting the ventilators (10) and (17),
  starting the heat exchanger (20),
  heating up the drying gas loop up to 95° C.,
  starting the nitrogen feed via the nitrogen inlet (19),
  waiting until the residual oxygen is below 4% by weight,
  heating up the drying gas loop,
  at a temperature of 105° C. starting the water feed (not shown) and
  at target temperature stopping the water feed and starting the monomer feed via dropletizer unit (4)

The shut-down of the cocurrent spray dryer (5) can be done in the following sequence:
  stopping the monomer feed and starting the water feed (not shown),
  shut-down of the heat exchanger (20),
  cooling the drying gas loop via heat exchanger (13),
  at a temperature of 105° C. stopping the water feed,
  at a temperature of 60° C. stopping the nitrogen feed via the nitrogen inlet (19) and
  feeding air into the drying gas loop (not shown)

To prevent damages the cocurrent spray dryer (5) must be heated up and cooled down very carefully. Any quick temperature change must be avoided.

Figure 9:
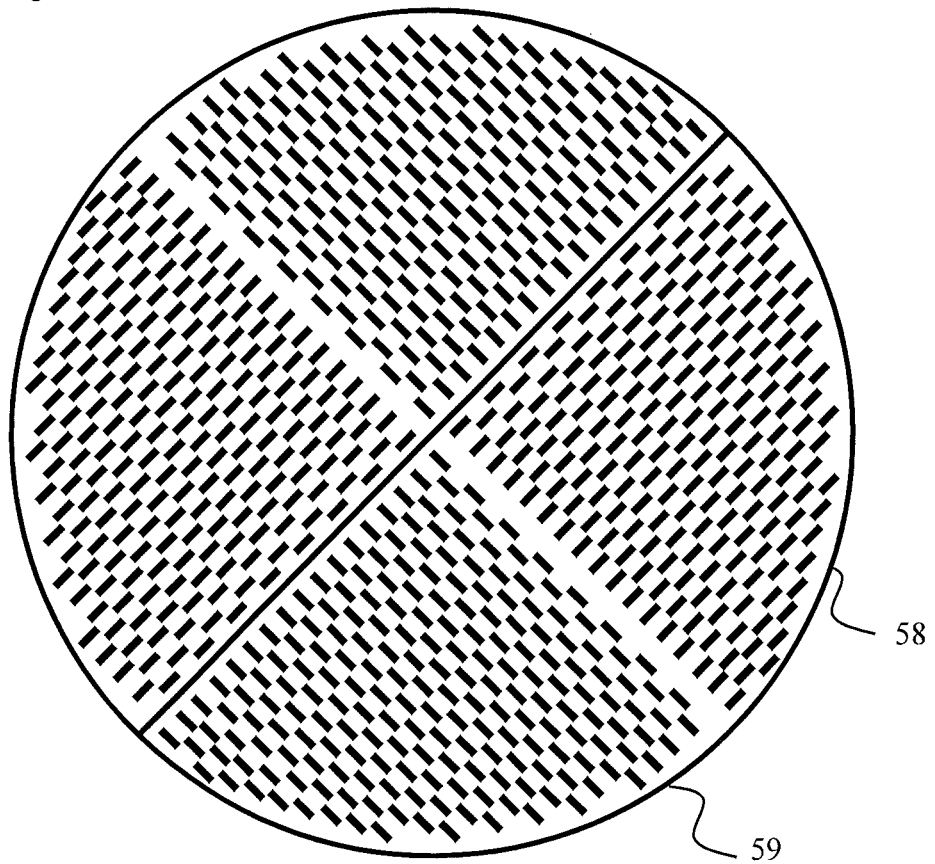
Figure 10:
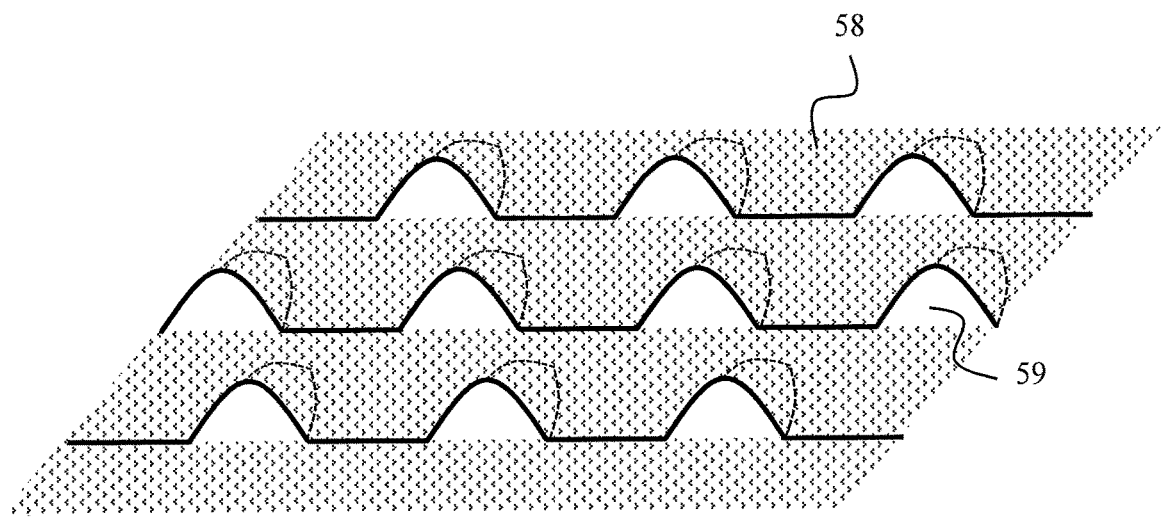

The openings in the bottom of the internal fluidized bed may be arranged in a way that the water-absorbent polymer particles flow in a cycle as shown in FIG. 9. The bottom shown in FIG. 9 comprises of four segments (58). The openings (59) in the segments (58) are in the shape of slits that guides the passing gas stream into the direction of the next segment (58). FIG. 10 shows an enlarged view of the openings (59).

The opening may have the shape of holes or slits. The diameter of the holes is preferred from 0.1 to 10 mm, more preferred from 0.2 to 5 mm, most preferred from 0.5 to 2 mm. The slits have a length of preferred from 1 to 100 mm, more preferred from 2 to 20 mm, most preferred from 5 to 10 mm, and a width of preferred from 0.5 to 20 mm, more preferred from 1 to 10 mm, most preferred from 2 to 5 mm.

Figure 11:
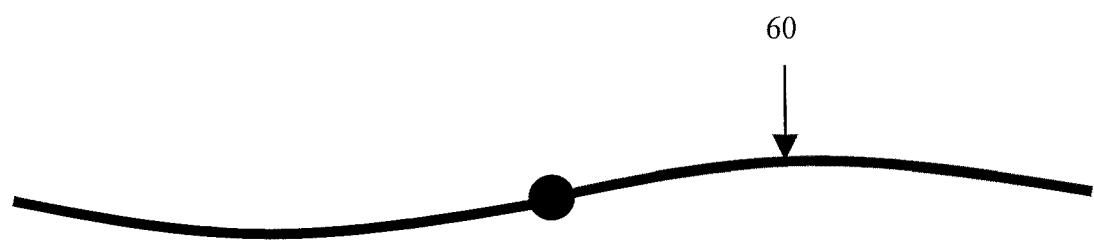
Figure 12:
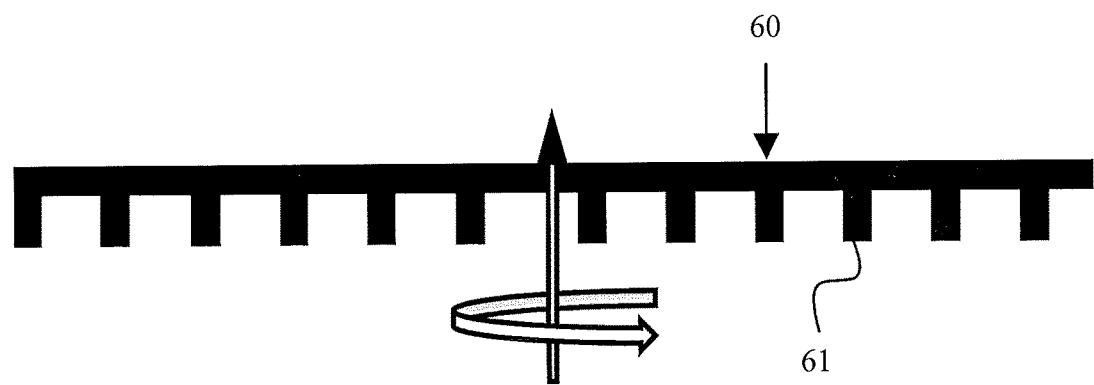
Figure 13:
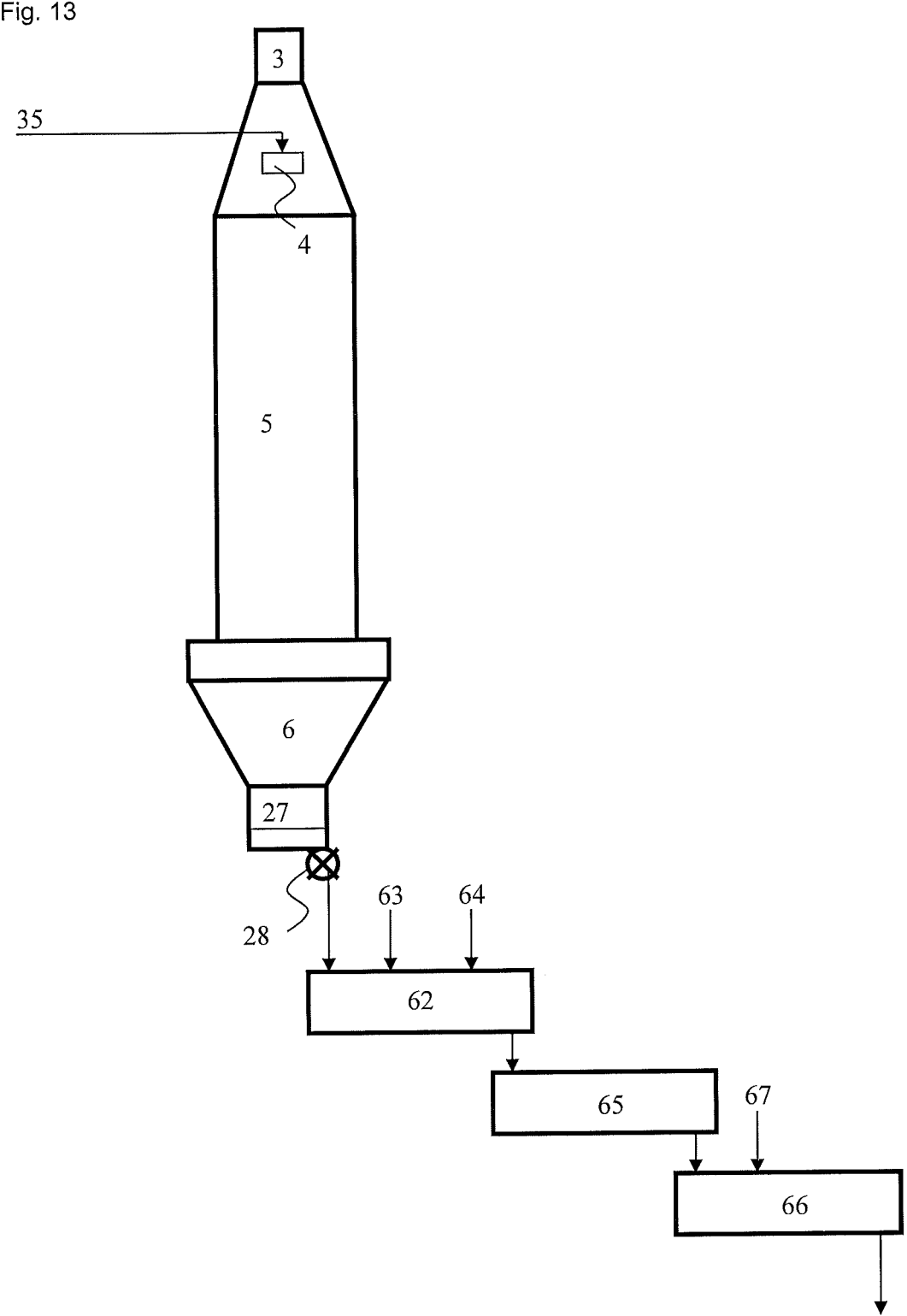
Figure 14:
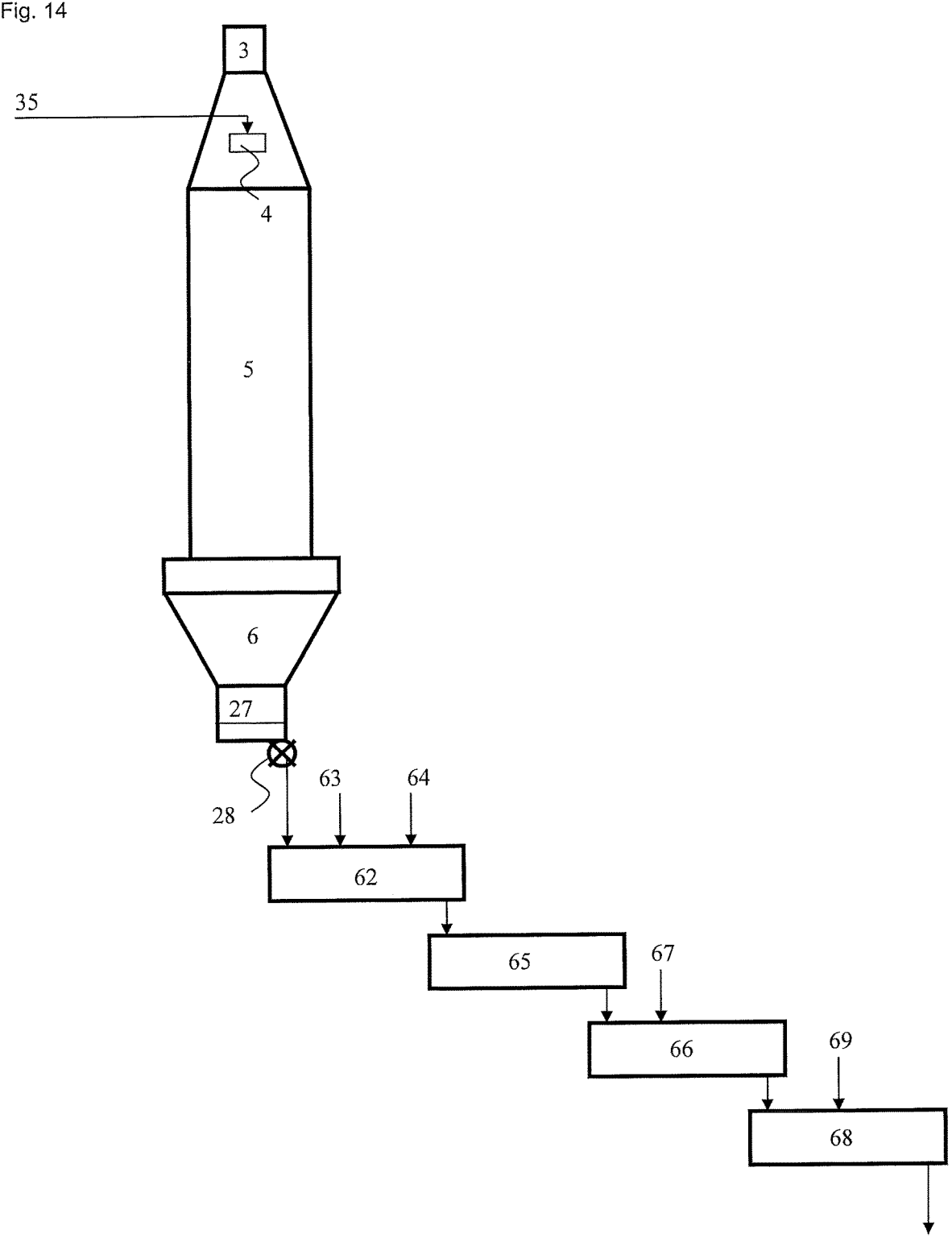

FIG. 11 and FIG. 12 show a rake stirrer (60) that may be used in the internal fluidized bed. The prongs (61) of the rake have a staggered arrangement. The speed of rake stirrer is preferably from 0.5 to 20 rpm, more preferably from 1 to 10 rpm most preferably from 2 to 5 rpm.

For start-up the internal fluidized bed may be filled with a layer of water-absorbent polymer particles, preferably 5 to 50 cm, more preferably from 10 to 40 cm, most preferably from 15 to 30 cm.

The resulting surface-postcrosslinked water-absorbent polymer particles obtained by dropletization having a mean sphericity from 0.80 to 0.95, preferably from 0.82 to 0.93, more preferably from 0.84 to 0.91, most preferably from 0.85 to 0.90. The sphericity (SPHT) is defined as $$SPHT = \frac{4\pi A}{U^2},$$

where A is the cross-sectional area and U is the cross-sectional circumference of the polymer particles. The mean sphericity is the volume-average sphericity.

The mean sphericity can be determined, for example, with the Camsizer® image analysis system (Retsch Technolgy GmbH; Haan; Germany):

For the measurement, the product is introduced through a funnel and conveyed to the falling shaft with a metering channel. While the particles fall past a light wall, they are recorded selectively by a camera. The images recorded are evaluated by the software in accordance with the parameters selected.

To characterize the roundness, the parameters designated as sphericity in the program are employed. The parameters reported are the mean volume-weighted sphericities, the volume of the particles being determined via the equivalent diameter $xc_{min}$. To determine the equivalent diameter $xc_{min}$, the longest chord diameter for a total of 32 different spatial directions is measured in each case. The equivalent diameter $xc_{min}$ is the shortest of these 32 chord diameters. To record the particles, the so-called CCD-zoom camera (CAM-Z) is used. To control the metering channel, a surface coverage fraction in the detection window of the camera (transmission) of 0.5% is predefined.

The resulting surface-crosslinked water-absorbent polymer particles obtained by dropletization furthermore have a centrifuge retention capacity (CRC) from 34 to 75 g/g, preferably from 37 to 65 g/g, more preferably from 39 to 60 g/g, most preferably from 40 to 55 g/g.

The surface crosslinked water-absorbent polymer particles have an absorbency under a load AUL (21 g/cm$^2$) from 30 to 50 g/g, preferably from 35 to 45 g/g.

The water-absorbent polymer particles obtained by dropletization (second superabsorbents) have a level of extractable constituents of less than 10% by weight, preferably less than 8% by weight, more preferably less than 6% by weight, most preferably less than 5% by weight.

Preferably the resulting surface-postcrosslinked water-absorbent polymer particles having a sphericity of at least 0.89, a centrifuge retention capacity of at least 34 g/g, an AUL (21 g/cm$^2$, WSP 242.3 (11)) of at least 30 g/g, a level of extractable constituents of less than 10% by weight.

Water-absorbent polymer particles obtained by dropletization have a bulk density preferably from 0.6 to 1 g/cm$^3$, more preferably from 0.65 to 0.9 g/cm$^3$, most preferably from 0.68 to 0.8 g/cm$^3$.

The average particle diameter of said water-absorbent particles is preferably from 200 to 550 µm, more preferably from 250 to 500 µm, most preferably from 350 to 450 µm.

C. Fluid-Absorbent Articles

The fluid-absorbent article comprises
(A) an upper liquid-pervious layer (89)
(B) a lower liquid-impervious layer (83)
(C) a fluid-absorbent core (80) between (A) and (B) comprising
  at least one layer (91), comprising from 0 to 20% by weight a fibrous material and from 80 to 100% by weight water-absorbent polymer particles;
  preferably from 0 to 10% by weight a fibrous material and from 90 to 100% by weight water-absorbent polymer particles;
  more preferably from 0 to 5% by weight a fibrous material and from 95 to 100% by weight water-absorbent polymer particles;
  most preferably from 0% by weight a fibrous material and from 100% by weight water-absorbent polymer particles;
  based on the sum of water-absorbent polymer material and fibrous material.
(E) other optional components.
Optionally the fluid-absorbent article comprises additionally
(D) an acquisition-distribution layer between (89) and (80).

Fluid-absorbent articles are understood to mean, for example, incontinence pads and incontinence briefs for adults or diapers and training pants for babies. Suitable fluid-absorbent articles including fluid-absorbent compositions comprising fibrous materials and optionally water-absorbent polymer particles to form fibrous webs or matrices for the substrates, layers, sheets and/or the fluid-absorbent core.

Suitable fluid-absorbent articles are composed of several layers whose individual elements must show preferably definite functional parameter such as dryness for the upper liquid-pervious layer, vapor permeability without wetting through for the lower liquid-impervious layer, a flexible, vapor permeable and thin fluid-absorbent core, showing fast absorption rates and being able to retain highest quantities of body fluids, and optionally of an acquisition-distribution layer between the upper layer and the core, acting as transport and distribution layer of the discharged body fluids. These individual elements are combined such that the resultant fluid-absorbent article meets overall criteria such as flexibility, water vapour breathability, dryness, wearing comfort and protection on the user facing side, and concerning liquid retention, rewet and prevention of wet through on the garment side. The specific combination of these layers provides a fluid-absorbent article delivering both high protection levels as well as high comfort to the consumer.

The core-structure (80) for fluid-absorbent products according to the invention is formed from absorbent paper. An absorbent paper core structure ususally is a sandwich structure comprising tissue, layers of water-absorbent polymer particles and nonwovens. The different components preferably are connected by adhesives.

For fluid-absorbent articles it is advantageous especially in respect to fluid distribution to have acquisition-distribution layers. For fluid-absorbent articles that possess a fluid-absorbent core according to the invention such an acquisition-distribution layer is not necessary.

The optional acquisition-distribution layer acts as transport and distribution layer of the discharged body fluids and is typically optimized to affect efficient liquid distribution with the underlying fluid-absorbent core. Hence, for quick temporary liquid retention it provides the necessary void space while its area coverage of the underlying fluid-absorbent core must affect the necessary liquid distribution and is adopted to the ability of the fluid-absorbent core to quickly dewater the acquisition-distribution layer.

Methods to make fluid absorbent articles are for example described in the following publications and literature cited therein and are expressly incorporated into the present invention: EP 2 301 499 A1, EP 2 314 264 A1, EP 2 387 981 A1, EP 2 486 901 A1, EP 2 524 679 A1, EP 2 524 679 A1, EP 2 524 680 A1, EP 2 565 031 A1, U.S. Pat. No. 6,972,011, US 2011/0162989, US 2011/0270204, WO 2010/004894 A1, WO 2010/004895 A1, WO 2010/076857 A1, WO 2010/082373 A1, WO 2010/118409 A1, WO 2010/133529 A2, WO 2010/143635 A1, WO 2011/084981 A1, WO 2011/086841 A1, WO 2011/086842 A1, WO 2011/086843 A1, WO 2011/086844 A1, WO 2011/117997 A1, WO 2011/136087 A1, WO 2012/048879 A1, WO 2012/052173 A1 and WO 2012/052172 A1.

Figure 16:
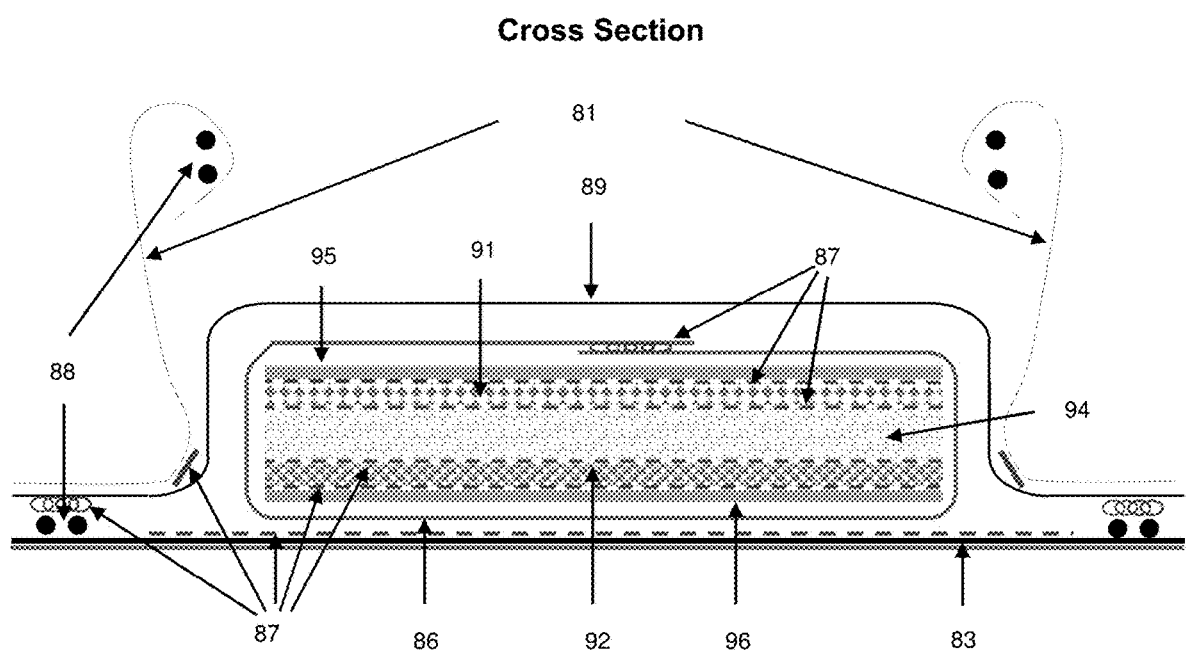
FIG. 16 is a schematic view of a fluid-absorbent article.

FIG. 16 is a schematical view of a fluid-absorbent article.

Figure 17A:
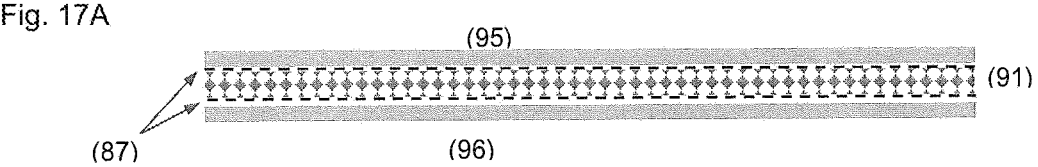
FIG. 17A is a schematic view of an absorbent core comprising one layer

The fluid-absorbent article comprises an absorbent core (80) comprising at least one layer of water-absorbent polymer particles (91/92) as illustrated in FIG. 17A, especially for fluid-storage, also called fluid-storage layer (91/92). Here two layers are shown, both sandwiched by a tissue layer (95/96) and at least one nonwoven (94), e.g. a high loft air thru bond nonwoven, connected by adhesives, ultrasonic bonding and/or heat bonding (87). Furthermore if more than one nonwoven is present, the nonwovens (94) are connected by adhesives, ultrasonic bonding and/or heat bonding (87). The absorbent core optionally may be wrapped by a nonwoven sheet (86), a core wrap, optionally connected by an adhesive, ultrasonic bonding and/or heat bonding (87) to the sandwich structure. Furthermore the absorbent article optionally comprises in addition to the core (80), and the optional core wrap (86), an acquisition distribution layer (ADL) on top of the nonwoven core wrap (86) below the coverstock or upper liquid-pervious sheet (89) (e. g. embossed spunbond nonwoven), and a lower liquid-impervious sheet (B) (83). Leg cuffs (81) and some elastics (88) may be also present.

Liquid-Pervious Sheet or Liquid Pervious Layer (A) (89)

The liquid-pervious sheet (A) (89) is the layer which is in direct contact with the skin. Thus, the liquid-pervious sheet (89) is preferably compliant, soft feeling and non-irritating to the consumer's skin. Generally, the term "liquid-pervious" is understood thus permitting liquids, i.e. body fluids such as urine, menses and/or vaginal fluids to readily penetrate through its thickness. The principle function of the liquid-pervious sheet is the acquisition and transport of body fluids from the wearer towards the fluid-absorbent core. Typically liquid-pervious layers (89) are formed from any materials known in the art such as nonwoven material, films or combinations thereof. Suitable liquid-pervious sheets (A) (89) consist of customary synthetic or semisynthetic fibers or bicomponent fibers or films of polyester, polyolefins, rayon or natural fibers or any combinations thereof. In the case of nonwoven materials, the fibers should generally be bound by binders such as polyacrylates. Additionally the liquid-pervious sheet may contain elastic compositions thus showing elastic characteristics allowing to be stretched in one or two directions.

Suitable synthetic fibers are made from polyvinyl chloride, polyvinyl fluoride, polytetrafluorethylene, polyvinylidene chloride, polyacrylics, polyvinyl acetate, polyethylvinyl acetate, non-soluble or soluble polyvinyl alcohol, polyolefins such as polyethylene, polypropylene, polyamides, polyesters, polyurethanes, polystyrenes and the like.

Examples for films are apertured formed thermoplastic films, apertured plastic films, hydroformed thermoplastic films, reticulated thermoplastic films, porous foams, reticulated foams, and thermoplastic scrims.

Examples of suitable modified or unmodified natural fibers include cotton, bagasse, kemp, flax, silk, wool, wood pulp, chemically modified wood pulp, jute, rayon, ethyl cellulose, and cellulose acetate.

The fibrous material may comprise only natural fibers or synthetic fibers or any combination thereof. Preferred materials are polyester, rayon and blends thereof, polyethylene, and polypropylene. The fibrous material as a component of the fluid-absorbent compositions may be hydrophilic, hydrophobic or can be a combination of both hydrophilic and hydrophobic fibers. The selection of the ratio hydrophilic/hydrophobic and accordingly the amount of hydrophilic and hydrophobic fibers within fluid-absorbent composition will depend upon fluid handling properties and the amount of water-absorbent polymer particles of the resulting fluid-absorbent composition.

Examples for hydrophilic fibers are cellulosic fibers, modified cellulosic fibers, rayon, polyester fibers such as polyethylen terephthalate, hydrophilic nylon and the like. Hydrophilic fibers can also be obtained from hydrophobic fibers which are hydrophilized by e. g. surfactant-treating or silica-treating. Thus, hydrophilic thermoplastic fibers derived from polyolefins such as polypropylene, polyamides, polystyrenes or the like by surfactant-treating or silica-treating.

To increase the strength and the integrity of the upper-layer, the fibers should generally show bonding sites, which act as crosslinks between the fibers within the layer.

Technologies for consolidating fibers in a web are mechanical bonding, thermal bonding and chemical bonding. In the process of mechanical bonding the fibers are entangled mechanically, e.g., by water jets (spunlace) to give integrity to the web. Thermal bonding is carried out by means of raising the temperature in the presence of low-melting polymers. Examples for thermal bonding processes are spunbonding, through-air bonding and resin bonding.

Preferred means of increasing the integrity are thermal bonding, spunbonding, resin bonding, through-air bonding and/or spunlace.

In the case of thermal bonding, thermoplastic material is added to the fibers. Upon thermal treatment at least a portion of this thermoplastic material is melting and migrates to intersections of the fibers caused by capillary effects. These intersections solidify to bond sites after cooling and increase the integrity of the fibrous matrix. Moreover, in the case of chemically stiffened cellulosic fibers, melting and migration of the thermoplastic material has the effect of increasing the pore size of the resultant fibrous layer while maintaining its density and basis weight. Upon wetting, the structure and integrity of the layer remains stable. In summary, the addition of thermoplastic material leads to improved fluid permeability of discharged body fluids and thus to improved acquisition properties.

Suitable thermoplastic materials including polyolefins such as polyethylene and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the mentioned polymers.

Suitable thermoplastic fibers can be made from a single polymer that is a monocomponent fiber. Alternatively, they can be made from more than one polymer, e.g., bi-component or multicomponent fibers. The term "bicomponent fibers" refers to thermoplastic fibers that comprise a core fiber made from a different fiber material than the shell. Typically, both fiber materials have different melting points, wherein generally the sheath melts at lower temperatures. Bi-component fibers can be concentric or eccentric depending whether the sheath has a thickness that is even or uneven through the cross-sectional area of the bicomponent fiber. Advantage is given for eccentric bi-component fibers showing a higher compressive strength at lower fiber thickness. Further bi-component fibers can show the feature "uncrimped" (unbent) or "crimped" (bent), further bi-component fibers can demonstrate differing aspects of surface lubricity.

Examples of bi-component fibers include the following polymer combinations: polyethylene/polypropylene, polyethylvinyl acetate/polypropylene, polyethylene/polyester, polypropylene/polyester, copolyester/polyester and the like.

Suitable thermoplastic materials have a melting point of lower temperatures that will damage the fibers of the layer; but not lower than temperatures, where usually the fluid-absorbent articles are stored. Preferably the melting point is between about 75° C. and 175° C. The typical length of thermoplastic fibers is from about 0.4 to 6 cm, preferably from about 0.5 to 1 cm. The diameter of thermoplastic fibers is defined in terms of either denier (grams per 9000 meters) or dtex (grams per 10 000 meters). Typical thermoplastic fibers have a dtex in the range from about 1.2 to 20, preferably from about 1.4 to 10.

A further mean of increasing the integrity of the fluid-absorbent composition is the spunbonding technology. The nature of the production of fibrous layers by means of spunbonding is based on the direct spinning of polymeric granulates into continuous filaments and subsequently manufacturing the fibrous layer.

Spunbond fabrics are produced by depositing extruded, spun fibers onto a moving belt in a uniform random manner followed by thermal bonding the fibers. The fibers are separated during the web laying process by air jets. Fiber bonds are generated by applying heated rolls or hot needles to partially melt the polymer and fuse the fibers together. Since molecular orientation increases the melting point, fibers that are not highly drawn can be used as thermal binding fibers. Polyethylene or random ethylene/propylene copolymers are used as low melting bonding sites.

Besides spunbonding, the technology of resin bonding also belongs to thermal bonding subjects. Using this technology to generate bonding sites, specific adhesives, based on e.g. epoxy, polyurethane and acrylic are added to the fibrous material and the resulting matrix is thermically treated. Thus the web is bonded with resin and/or thermal plastic resins dispersed within the fibrous material.

As a further thermal bonding technology through-air bonding involves the application of hot air to the surface of the fibrous fabric. The hot air is circulated just above the fibrous fabric, but does not push through the fibrous fabric. Bonding sites are generated by the addition of binders. Suitable binders used in through-air thermal bonding include crystalline binder fibers, bi-component binder fibers, and powders. When using crystalline binder fibers or powders, the binder melts entirely and forms molten droplets throughout the nonwoven's cross-section. Bonding occurs at these points upon cooling. In the case of sheath/core binder fibers, the sheath is the binder and the core is the carrier fiber. Products manufactured using through-air ovens tend to be bulky, open, soft, strong, extensible, breathable and absorbent. Through-air bonding followed by immediate cold calendering results in a thickness between a hot roll calendered product and one that has been though-air bonded without compression. Even after cold calendering, this product is softer, more flexible and more extensible than area-bond hot-calendered material.

Spunlacing ("hydroentanglement") is a further method of increasing the integrity of a web. The formed web of loose fibers (usually air-laid or wet-laid) is first compacted and prewetted to eliminate air pockets. The technology of spunlacing uses multiple rows of fine high-speed jets of water to strike the web on a porous belt or moving perforated or patterned screen so that the fibers knot about one another. The water pressure generally increases from the first to the last injectors. Pressures as high as 150 bar are used to direct the water jets onto the web. This pressure is sufficient for most of the nonwoven fibers, although higher pressures are used in specialized applications.

The spunlace process is a nonwovens manufacturing system that employs jets of water to entangle fibers and thereby provide fabric integrity. Softness, drape, conformability, and relatively high strength are the major characteristics of spunlace nonwoven.

In newest researches benefits are found in some structural features of the resulting liquid-pervious layers. For example, the thickness of the layer is very important and influences together with its x-y dimension the acquisition-distribution behaviour of the layer. If there is further some profiled structure integrated, the acquisition-distribution behaviour can be directed depending on the three-dimensional structure of the layer. Thus 3D-polyethylene in the function of liquid-pervious layer is preferred.

Thus, suitable liquid-pervious sheets (A) are nonwoven layers formed from the fibers above by thermal bonding, spunbonding, resin bonding or through-air bonding. Further suitable liquid-pervious layers are 3D-polyethylene layers and spunlace.

Preferably the 3D-polyethylene layers and spunlace show basis weights from 12 to 22 gsm.

Typically liquid-pervious sheets (A) (89) extend partially or wholly across the fluid-absorbent structure and can extend into and/or form part of all the preferred sideflaps, side wrapping elements, wings and ears.

Liquid-Impervious Sheet or Liquid Impervious Layer (B) (83)

The liquid-impervious sheet (B) (83) prevents the exudates absorbed and retained by the fluid-absorbent core (80) from wetting articles which are in contact with the fluid-absorbent article, as for example bedsheets, pants, pyjamas and undergarments. The liquid-impervious sheet (83) may thus comprise a woven or a nonwoven material, polymeric films such as thermoplastic film of polyethylene or polypropylene, or composite materials such as film-coated nonwoven material.

Suitable liquid-impervious sheets (83) include nonwoven, plastics and/or laminates of plastic and nonwoven. Both, the plastics and/or laminates of plastic and nonwoven may appropriately be breathable, that is, the liquid-impervious layer (83) can permit vapors to escape from the fluid-absorbent material. Thus the liquid-impervious sheet has to have a definite water vapor transmission rate and at the same time the level of impermeability. To combine these features, suitable liquid-impervious layers including at least two layers, e.g. laminates from fibrous nonwoven having a specified basis weight and pore size, and a continuous three-dimensional film of e.g. polyvinylalcohol as the second layer having a specified thickness and optionally having pore structure. Such laminates acting as a barrier and showing no liquid transport or wet through. Thus, suitable liquid-impervious layers comprising at least a first breathable layer of a porous web which is a fibrous nonwoven, e.g. a composite web of a meltblown nonwoven layer or of a spunbonded nonwoven layer made from synthetic fibers and at least a second layer of a resilient three dimensional web consisting of a liquid-impervious polymeric film, e.g. plastics optionally having pores acting as capillaries, which are preferably not perpendicular to the plane of the film but are disposed at an angle of less than 90° relative to the plane of the film.

Suitable liquid-impervious sheets are permeable for vapor. Preferably the liquid-impervious sheet is constructed from vapor permeable material showing a water vapor transmission rate (WVTR) of at least about 100 gsm per 24 hours, preferably at least about 250 gsm per 24 hours and most preferred at least about 500 gsm per 24 hours.

Preferably the liquid-impervious sheet (B) (83) is made of nonwoven comprising hydrophobic materials, e.g. synthetic fibers or a liquid-impervious polymeric film comprising plastics e.g. polyethylene. The thickness of the liquid-impervious sheet is preferably 15 to 30 µm.

Further, the liquid-impervious sheet (B) (83) is preferably made of a laminate of nonwoven and plastics comprising a nonwoven having a density of 12 to 15 gsm and a polyethylene layer having a thickness of about 10 to 20 µm.

The typically liquid-impervious sheet (B) (83) extends partially or wholly across the fluid-absorbent structure and can extend into and/or form part of all the preferred side-flaps, side wrapping elements, wings and ears.

Fluid-Absorbent Core (C) or (80)

The fluid-absorbent core (C) (80) is disposed between the upper liquid-pervious sheet (A) (89) and the lower liquid-impervious sheet (B) (83).

According to the present invention the fluid-absorbent core (80) can be formed from absorbent paper.

In order to increase the integrity of the fluid-absorbent core (80), the core is provided with a cover (86). This cover may be at the top and/or at the bottom of the fluid-absorbent core (80) with bonding at lateral juncture and/or bonding at the distal juncture by hot-melt, ultrasonic bonding, thermal bonding or combination of bonding techniques know to persons skilled in the art. Further, this cover may include the whole fluid-absorbent core with a unitary sheet of material and thus function as a wrap. Wrapping is possible as a full wrap, a partial wrap or as a C-Wrap.

The material of the core cover (86) may comprise any known type of substrate, including nonwovens, webs, garments, textiles, films, tissues and laminates of two or more substrates or webs. The core cover material may comprise natural fibers, such as cellulose, cotton, flax, linen, hemp, wool, silk, fur, hair and naturally occurring mineral fibers. The core cover material may also comprise synthetic fibers such as rayon and lyocell (derived from cellulose), polysaccharides (starch), polyolefin fibers (polypropylene, polyethylene), polyamides, polyester, butadiene-styrene block copolymers, polyurethane and combinations thereof. Preferably, the core cover comprises synthetic fibers or tissue.

The fibers may be mono- or multicomponent. Multicomponent fibers may comprise a homopolymer, a copolymer or blends thereof.

A schematic view of the absorbent core/absorbent paper (80) is shown in FIG. 17. Absorbent core/absorbent paper (80) according to the invention as shown in FIG. 17 A, comprises at least one layer of water-absorbent polymer particles (91), sandwiched with at least two layers of tissue, e. g. condensed tissue, on the top (95) and bottom (96) using adhesive applied to the surface (87), ultrasonic bonding and/or heat bonding.

The basis for the absorbent paper (80) is a thin and flexible single layer of suitable absorbent material. The layer is macroscopically two-dimensional and planar and of very low thickness compared to the other dimensions. Said layer may also incorporate superabsorbent material throughout the layer.

Techniques of application of the water-absorbent polymer materials into the absorbent core are known to persons skilled in the art and may be volumetric, loss-in-weight or gravimetric. Known techniques include the application by vibrating systems, single and multiple auger systems, dosing roll, weigh belt, fluid bed volumetric systems and gravitational sprinkle and/or spray systems. Further techniques of insertion are falling dosage systems consensus and contradictory pneumatic application or vacuum printing method of applying the fluid absorbent polymer materials.

Figure 17B:
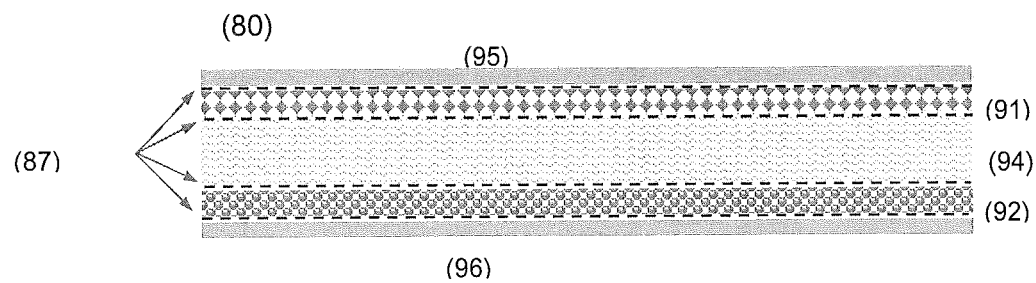
FIG. 17B is a schematic views of an absorbent core comprising two layers.

Alternatively a core-structure can be formed from two or more preformed layers comprising water absorbent polymer particles as e.g. shown in FIG. 17B to get a layered fluid-absorbent core.

In FIG. 17 B a two layered absorbent core (80) is shown. Here two layers of water-absorbent polymer particles one of which laid on top side (91) and another laid on the bottom (92) are connected (87) with adhesive, ultrasonic bonding and/or heat bonding on nonwoven e.g. air-thru-bond nonwoven material (94) and are then sandwiched with two layers of e.g. condensed tissue layers on the top (95) and bottom (96) using adhesive, ultrasonic bonding and/or heat bonding applied to the surface.

The layered structure may be formed by subsequently generating the different layers in z-direction.

The layers may have different concentrations and different water-absorbent polymer material showing concentrations in the range from about 80 to 100%, preferably 90 to 100%. These uniform or different layers can be fixed to each other at their adjacent plane surfaces. Alternatively, the layers may be combined in a way that a plurality of chambers are formed, in which separately water-absorbent polymer material is incorporated.

Furthermore it can be preferred that the water-absorbent polymer particles are placed within the at least one layer (91) in discrete regions even without chambers, e.g. supportet by at least an adhesive.

It may be preferred that the water-absorbent polymer particles discretely contained in closed pockets. The pockets are free of cellulose pulp. The bonds to define pockets are formed e.g. by intersection of ultrasonic contact areas between two thermoplastic containment layers. Suitable preformed layers are processed as e.g. air-laid, wet-laid, laminate or composite structure.

The absorbent paper (80) may comprise at least one layer of nonwoven (94) material such as short-fiber air-laid nonwoven materials; nonwoven of materials such as polyethylene, polypropylene, nylon, polyester, and the like; cellulosic fibrous materials such as paper tissue or towels known in the art, wax-coated papers, corrugated paper materials, and the like; or fluff pulp. Said layer may further incorporate bi-component binding fibers.

According to the invention a tissue layer is disposed immediately above and below the at least one layer containg water-absorbent polymers within the absorbent core.

The term tissue is not restricted to tissue material such as paper it also refers to nonwovens. The material of the layer may comprise any known type of substrate, including webs, garments, textiles and films. The tissuelayer may comprise natural fibers, such as cellulose, cotton, flax, linen, hemp, wool, silk, fur, hair and naturally occurring mineral fibers. The tissue layer may also comprise synthetic fibers such as rayon and lyocell (derived from cellulose), polysaccharides (starch), polyolefin fibers (polypropylene, polyethylene), polyamides, polyester, butadiene-styrene block copolymers, polyurethane and combinations thereof. Preferably, the tissue layer comprises cellulose fibers.

It is preferred that the tissue layer is made from ca. 50% wood pulp and 50% chemical viscose fibers at >45 gsm to provide tensile strength and integrity.

According to the invention it is preferred that the fluid-absorbent core comprises not more than 20% by weight of an adhesive, preferably not more than 10% by weight of an adhesive, more preferably not more than 7% by weight of an adhesive, most preferably not more than 5% by weight of an adhesive. Preferably the adhesive is a hotmelt adhesive.

The quantity of water-absorbent polymer particles within the fluid-absorbent core (absorbent paper) is from 3 to 20 g, preferably from 6 to 14 g, and from 8 to 12 g in the case of maxi-diapers, and in the case of incontinence products up to about 50 g.

The quantity of water-absorbent polymer particles within the fluid-absorbent core (absorbent paper) is from 100 to 500 gsm, preferably 200 to 400 gsm, more preferably 250 to 300 gsm in case of maxi diapers (size L), It is preferred (FIG. 17A) that the at least one layer of water-absorbent polymer particles (91) of the absorbent core comprises from 0 to 20% by weight fibrous material and from 80 to 100%, preferably from 0 to 10% by weight fibrous material and from 90 to 100% by weight water-absorbent polymer particles, based on the sum of water-absorbent polymer particles and fibrous material, contains at least 260 gsm water absorbent polymer particles, preferably at least 350 gsm water absorbent polymer particles.

It may be preferred that the at least one layer comprises 100% by weight of water-absorbent particles.

In an absorbent core comprising at least two layers (FIG. 17B) each of an upper layer (91) and a lower layer (92), comprises from 0 to 10% by weight fibrous material and from 90 to 100% by weight water-absorbent polymer particles, based on the sum of water-absorbent polymer particles and fibrous material, wherein each layer contains at least 50 gsm water absorbent polymer particles preferably at least 100 gsm water absorbent polymer particles.

Thus, according to the number of layers, the resulting thickness of the fluid-absorbent core will be determined. Thus, fluid-absorbent cores may be flat as one layer (plateau) or have three-dimensional profile.

The water absorbent polymer particles in each layer may be different.

According to the invention the at least one layer contains fast superabsorbent or a blend of water absorbent polymer particles.

Wherein the blend comprises at least 20 wt.-% of fast superabsorbent material having a surface area of at least 1000 cm$^2$/g.

The blend further may contain 80 wt.-% or less of the second superabsorbent.

Preferably, especially in case the fluid-absorbent article contains no acquisition distribution layer (ADL) between the upper liquid-pervious layer (89) and the fluid-absorbent core (80) the blend comprises 25 to 100 wt.-% of the fast superabsorbent and 75 to 0 wt.-% of the second superabsorbent. More preferably the blend comprises 30 to 100 wt.-% of the fast superabsorbent and 70 to 0 wt.-% of the second superabsorbent. Even without ADL the inventive fluid absorbent article has a first intake time of 15 seconds or less by the hanging U-shape test (HUS).

To ensure also low rewet even without an ADL present, it is preferred that the blend comprises 30 to 75 wt.-% of the second superabsorbent and 70 to 25 wt.-% of the fast superabsorbent. It is also preferred that the blend comprises 30 to 70 wt.-% of the second superabsorbent and 70 to 30 wt.-% of the fast superabsorbent. Accoridng to another embodiment of the present invention it is preferred that the blend comprises 35 to 65 wt.-% of the second superabsorbent and 65 to 35 wt.-% of the fast superabsorbent.

According to the invention it is preferred that the second superabsorbent having a spericity of at least 0.89.

The second superabsorbent is preferably produced by polymerizing droplets of the monomer in a surrounding heated gas phase.

The fast superabsorbent according to the invention having a $t_{corr}$ value of 12 sec/g or less, preferably 7.5 sec/g or less, most preferably 6 sec/g or less. The $t_{corr}$ is defined by the following equation:

$$t_{corr} = \frac{\frac{t_{12g}}{g}}{(SA/100)m_{sap}}$$

The fluid-absorbent core (80) typically has a uniform size or profile. Suitable fluid-absorbent cores can also have profiled structures, concerning the shape of the core and/or the content of water-absorbent polymer particles and/or the distribution of the water-absorbent polymer particles and/or the dimensions of the different layers if a layered fluid-absorbent core is present.

The shape of the core (80) in view from above (x-y dimension) can be rectangular, anatomical shaped with a narrower crotch area or any other shapes.

The top view area of the fluid-absorbent core (80) is preferably at least 200 cm$^2$, more preferably at least 250 cm$^2$, most preferably at least 300 cm$^2$. The top view area is the part of the core that is face-to-face to the upper liquid-pervious layer.

The fluid-absorbent core (80) may comprise additional additives typically present in fluid-absorbent articles known in the art. Exemplary additives are fibers for reinforcing and stabilizing the fluid-absorbent core. Preferably polyethylene is used for reinforcing the fluid-absorbent core.

Further suitable stabilizer for reinforcing the fluid-absorbent core are materials acting as binder.

In varying the kind of binder material or the amount of binder used in different regions of the fluid-absorbent core it is possible to get a profiled stabilization. For example, different binder materials exhibiting different melting temperatures may be used in regions of the fluid-absorbent core, e.g. the lower melting one in the central region of the core, and the higher melting in the distal regions. Suitable binder materials may be adhesive or non-adhesive fibers, continuously or discontinuously extruded fibers, bi-component staple fibers, nonelastomeric fibers and sprayed liquid binder or any combination of these binder materials.

Further, thermoplastic compositions usually are added to increase the integrity of the core layer. Thermoplastic compositions may comprise a single type of thermoplastic polymers or a blend of thermoplastic polymers. Alternatively, the thermoplastic composition may comprise hot melt adhesives comprising at least one thermoplastic polymer together with thermoplastic diluents such as tackifiers, plasticizers or other additives, e.g. antioxidants. The thermoplastic composition may further comprise pressure sensitive hot melt adhesives comprising e.g. crystalline polypropylene and an amorphous polyalphaolefin or styrene block copolymer and mixture of waxes.

Concerning odor control, perfumes and/or odor control additives are optionally added. Suitable odor control additives are all substances of reducing odor developed in carrying fluid-absorbent articles over time known in the art. Thus, suitable odor control additives are inorganic materials, such as zeolites, activated carbon, bentonite, silica, aerosile, kieselguhr, clay; chelants such as ethylenediamine tetraacetic acid (EDTA), cyclodextrins, aminopolycarbonic acids, ethylenediamine tetramethylene phosphonic acid, aminophosphate, polyfunctional aromates, N,N-disuccinic acid. Suitable odor control additives are further antimicrobial agents.

Suitable odor control additives are further compounds with anhydride groups such as maleic-, itaconic-, polymaleic- or polyitaconic anhydride, copolymers of maleic acid with $C_2$-$C_8$ olefins or styrene, polymaleic anhydride or copolymers of maleic anhydride with isobutene, di-isobutene or styrene, compounds with acid groups such as ascorbic, benzoic, citric, salicylic or sorbic acid and fluid-soluble polymers of monomers with acid groups, homo- or copolymers of $C_3$-$C_5$ mono-unsaturated carboxylic acids.

Newest developments propose the addition of wetness indication additives.

Suitable wetness indication additives comprising a mixture of sorbitan monooleate and polyethoxylated hydrogenated castor oil. Preferably, the amount of the wetness indication additive is in the range of about 0.0001 to 2% by weight related to the weight of the fluid-absorbent core.

The absorbent paper layer has a total basis weight ranging from about 100 gsm to about 2000 gsm, preferably from about 200 gsm to about 750 gsm, and more preferrably from about 400 gsm to about 600 gsm.

The density of the fluid-absorbent core is in the range of 0.1 to 0.6 g/cm$^3$, preferably 0.2 to 0.4 g/cm$^3$. The thickness of the fluid-absorbent core is in the case of diapers in the range of 1 to 8 mm, preferably 1 to 4 mm, more preferably 1.5 to 3 mm, in the case of adult-incontinence products in the range of 3 to 15 mm.

Optional Acquisition-Distribution Layer (D)

An optional acquisition-distribution layer (D) is located between the upper layer (89) and the fluid-absorbent core (80) and is preferably constructed to efficiently acquire discharged body fluids and to transfer and distribute them to other regions of the fluid-absorbent composition or to other layers, where the body fluids are immobilized and stored. Thus, the upper layer transfers the discharged liquid to the acquisition-distribution layer (D) for distributing it to the fluid-absorbent core.

The acquisition-distribution layer comprises fibrous material and optionally water-absorbent polymer particles.

The fibrous material may be hydrophilic, hydrophobic or can be a combination of both hydrophilic and hydrophobic fibers. It may be derived from natural fibers, synthetic fibers or a combination of both.

Suitable acquisition-distribution layers are formed from cellulosic fibers and/or modified cellulosic fibers and/or synthetics or combinations thereof. Thus, suitable acquisition-distribution layers may contain cellulosic fibers, in particular wood pulp fluff. Examples of further suitable hydrophilic, hydrophobic fibers, as well as modified or unmodified natural fibers are given in the chapter "Liquid-pervious sheet or liquid pervious layer (A) (89)" above.

Especially for providing both fluid acquisition and distribution properties, the use of modified cellulosic fibers is preferred. Examples for modified cellulosic fibers are chemically treated cellulosic fibers, especially chemically stiffened cellulosic fibers. The term "chemically stiffened cellulosic fibers" means cellulosic fibers that have been stiffened by chemical means to increase the stiffness of the fibers. Such means include the addition of chemical stiffening agent in the form of surface coatings, surface crosslinking and impregnates. Suitable polymeric stiffening agents can include: cationic modified starches having nitrogen-containing groups, latexes, wet strength resins such as polyamide-epichlorohydrin resin, polyacrylamide, urea formaldehyde and melamine formaldehyde resins and polyethylenimine resins.

Stiffening may also include altering the chemical structure, e.g. by crosslinking polymer chains. Thus crosslinking agents can be applied to the fibers that are caused to chemically form intrafiber crosslink bonds. Further cellulosic fibers may be stiffened by crosslink bonds in individualized form. Suitable chemical stiffening agents are typically monomeric crosslinking agents including $C_2$-$C_9$ dialdehyde, $C_2$-$C_9$ monoaldehyde having an acid functionality, and especially $C_2$-$C_9$ polycarboxylic acids.

Preferably the modified cellulosic fibers are chemically treated cellulosic fibers. Especially preferred are curly fibers which can be obtained by treating cellulosic fibers with citric acid. Preferebly the basis weight of cellulosic fibers and modified cellulosic fibers is from 50 to 200 gsm.

Suitable acquisition-distribution layers further include synthetic fibers. Known examples of synthetic fibers are found in the Chapter "Liquid-pervious sheet or liquid pervious layer (A) (89)" above. Another possibility available is 3D-polyethylene film with dual function as a liquid-pervious layer (A) (89) and acquisition-distribution layer.

Further, as in the case of cellulosic fibers, hydrophilic synthetic fibers are preferred. Hydrophilic synthetic fibers may be obtained by chemical modification of hydrophobic fibers. Preferably, hydrophilization is carried out by surfactant treatment of hydrophobic fibers. Thus the surface of the hydrophobic fiber can be rendered hydrophilic by treatment with a nonionic or ionic surfactant, e.g., by spraying the fiber with a surfactant or by dipping the fiber into a surfactant. Further preferred are permanent hydrophilic synthetic fibers. The fibrous material of the acquisition-distribution layer may be fixed to increase the strength and the integrity of the layer. Technologies for consolidating fibers in a web are mechanical bonding, thermal bonding and chemical bonding. Detailed description of the different methods of increasing the integrity of the web is given in the Chapter "Liquid-pervious sheet or liquid pervious layer (A) (89)" above.

Preferred acquisition-distribution layers (D) comprise fibrous material and water-absorbent polymer particles distributed within. The water-absorbent polymer particles may be added during the process of forming the layer from loose fibers, or, alternatively, it is possible to add monomer solution after the formation of the layer and polymerize the coating solution by means of UV-induced polymerisation technologies. Thus, "in situ"-polymerisation is a further method for the application of water-absorbent polymers.

Thus, suitable acquisition-distribution layers comprising from 80 to 100% by weight a fibrous material and from 0 to 20% by weight water-absorbent polymer particles; preferably from 85 to 99.9% by weight a fibrous material and from 0.1 to 15% by weight water-absorbent polymer particles; more preferably from 90 to 99.5% by weight a fibrous material and from 0.5 to 10% by weight water-absorbent polymer particles; and most preferably from 95 to 99% by weight a fibrous material and from 1 to 5% by weight water-absorbent polymer particles.

Preferred acquisition-distribution layers show basis weights in the range from 20 to 200 gsm, most preferred in the range from 40 to 60 gsm, depending on the concentration of water-absorbent polymer particles.

Alternatively an acquisition-distribution layer (D) comprising a synthetic resin film between (89) and (80) acting as a distribution layer and quickly transporting the supplied urine along the surface to the upper lateral portion of the fluid-absorbent core (80). Preferably, the acquisition-distribution layer (D) is smaller than the under-laying fluid-absorbent core (80). There is no limit in particular to the material of the acquisition-distribution layer (D). Such a film made of a resin such as polyethylene, polypropylene, polyethylene therephthalate, polyurethane, or crosslinked polyvinyl alcohol and an air-permeable, but liquid-impervious, so-called: "breathable" film made of above described resin, may be used.

Preferably, the acquisition-distribution layers (D) comprises a porous polyethylene film for both quick acquisition and distribution of fluid.

Alternatively a bundle of synthetic fibers acting as acquisition-distribution layer loosely distributed on top of the fluid-absorbent core may be used. Suitable synthetic fibers are of copolyester, polyamide, copolyamide, polylactic acid, polypropylene or polyethylene, viscose or blends thereof. Further bicomponent fibers can be used. The synthetic fiber component may be composed of either a single fiber type with a circular cross-section or a blend of two fibre types with different cross-sectional shapes. Synthetic fibers arranged in that way ensuring a very fast liquid transport and canalisation. Preferrably bundles of polyethylene fibers are used.

Other Optional Components (E)

1. Leg Cuff

Typical leg cuffs comprising nonwoven materials which can be formed by direct extrusion processes during which the fibers and the nonwoven materials are formed at the same time, or by laying processes of preformed fibers which can be laid into nonwoven materials at a later point of time. Examples for direct extrusion processes include spunbonding, meltblowing, solvent spinning, electrospinning and combinations thereof. Examples of laying processes include wet-laying and dry-laying (e.g. air-laying, carding) methods. Combinations of the processes above include spunbond-meltblown-spunbond (sms), spunbond-meltblow-meltblown-spunbond (smms), spunbond-carded (sc), spunbond-airlaid (sa), meltblown-airlaid (ma) and combinations thereof. The combinations including direct extrusion can be combined at the same point in time or at a subsequent point in time. In the examples above, one or more individual layers can be produced by each process. Thus, "sms" means a three layer nonwoven material, "smsms" or "ssmms" means a five layer nonwoven material. Usually, small type letters (sms) designate individual layers, whereas capital letters (SMS) designate the compilation of similar adjacent layers.

Further, suitable leg cuffs are provided with elastic strands.

Preferred are leg cuffs from synthetic fibers showing the layer combinations sms, smms or smsms. Preferred are nonwovens with the density of 13 to 17 gsm. Preferably leg cuffs are provided with two elastic strands.

2. Elastics

The elastics are used for securely holding and flexibly closing the fluid-absorbent article around the wearers' body, e.g. the waist and the legs to improve containment and fit. Leg elastics are placed between the outer and inner layers or the fluid-absorbent article, or between the outer garment facing cover and the user facing bodyside liner. Suitable elastics comprising sheets, ribbons or strands of thermoplastic polyurethane, elastomeric materials, poly(ether-amide) block copolymers, thermoplastic rubbers, styrene-butadiene copolymers, silicon rubbers, natural rubbers, synthetic rubbers, styrene isoprene copolymers, styrene ethylene butylene copolymers, nylon copolymers, spandex fibers comprising segmented polyurethane and/or ethylene-vinyl acetate copolymer. The elastics may be secured to a substrate after being stretched, or secured to a stretched substrate. Otherwise, the elastics may be secured to a substrate and then elastisized or shrunk, e.g. by the application of heat.

3. Closing System

The closing system can include tape tabs, landing zone, elastomerics, pull ups and the belt system or combinations thereof At least a part of the first waist region is attached to a part of the second waist region by the closing system to hold the fluid-absorbent article in place and to form leg openings and the waist of the fluid-absorbent article. Preferably the fluid-absorbent article is provided with a re-closable closing system.

The closing system is either re-sealable or permanent, including any material suitable for such a use, e.g. plastics, elastics, films, foams, nonwoven substrates, woven substrates, paper, tissue, laminates, fiber reinforced plastics and the like, or combinations therof. Preferably the closing system includes flexible materials and works smooth and softly without irritating the wearer's skin.

One part of the closing elements is an adhesive tape, or comprises a pair of laterally extending tabs disposed on the lateral edges of the first waist region. Tape tabs are typically attached to the front body panel and extend laterally from each corner of the first waistband. These tape tabs include an adhesive inwardly facing surface which is typically protected prior to use by a thin, removable cover sheet.

Suitable tape tabs may be formed of thermoplastic polymers such as polyethylene, polyurethane, polystyrene, polycarbonate, polyester, ethylene vinyl acetate, ethylene vinyl alcohol, ethylene vinyl acetate acrylate or ethylene acrylic acid copolymers.

Suitable closing systems comprise further a hook portion of a hook and loop fastener and the target devices comprise the loop portion of a hook and loop fastener.

Suitable mechanical closing systems including a landing zone. Mechanical closing systems may fasten directly into the outer cover. The landing zone may act as an area of the fluid-absorbent article into which it is desirable to engage the tape tabs. The landing zone may include a base material and a plurality of tape tabs. The tape tabs may be embedded in the base material of the landing zone. The base material may include a loop material. The loop material may include a backing material and a layer of a nonwoven spunbond web attached to the backing material.

Thus suitable landing zones can be made by spunbonding. Spunbonded nonwoven are made from melt-spun fibers formed by extruding molten thermoplastic material. Preferred is bi-oriented polypropylene (BOPP), or brushed/closed loop in the case of mechanical closing systems.

Further, suitable mechanical closing systems including elasticomeric units serving as a flexible abdominal and/or dorsal discrete waist band, flexible abdomen and/or dorsal zones located at distal edge for fluid-absorbents articles, such as pants or pull-ups. The elasticomeric units enable the fluid-absorbent article to be pulled down by the wearer as e.g. a training pant.

Suitable pants-shaped fluid-absorbent article has front abdominal section, rear dorsal section, crotch section, side sections for connecting the front and rear sections in lateral direction, hip section, elastic waist region and liquid-tight outer layer. The hip section is arranged around the waist of the user. The disposable pants-shaped fluid-absorbent article (pull-up) has favorable flexibility, stretchability, leak-proof property and fit property, hence imparts excellent comfort to the wearer and offers improved mobility and discretion.

Suitable pull-ups comprising thermoplastic films, sheets and laminates having a low modulus, good tear strength and high elastic recovery.

Suitable closing systems may further comprise elastomerics for the production of elastic areas within the fastening devices of the fluid-absorbent article. Elastomerics provide a conformable fit of the fluid-absorbent article to the wearer at the waist and leg openings, while maintaining adequate performance against leakage.

Suitable elastomerics are elastomeric polymers or elastic adhesive materials showing vapor permeability and liquid barrier properties. Preferred elastomerics are retractable after elongation to a length equivalent to its original length.

Suitable closing systems further comprise a belt system, comprising waist-belt and leg-belts for flexibly securing the fluid-absorbent article on the body of the wearer and to provide an improved fit on the wearer. Suitable waist-belts comprising two elastic belts, a left elastic belt, and a right elastic belt. The left elastic belt is associated with each of the left angular edges. The right elastic belt associated with each of the right angular edges. The left and right side belts are elastically extended when the absorbent garment is laid flat. Each belt is connected to and extends between the front and rear of the fluid-absorbent article to form a waist hole and leg holes.

Preferably the belt system is made of elastomerics, thus providing a conformable fit of the fluid-absorbent article and maintaining adequate performance against leakage.

Preferred closing systems are so-called "elastic ears" attached with one side of the ear to the longitudinal side edges located at the rear dorsal longitudinal edge of the chassis of the fluid-absorbent article. Commercially available fluid-absorbent articles include stretchable ears or side panels which are made from a stretchable laminate e.g. nonwoven webs made of mono- or bi-component fibers. Especially preferred closing systems are stretchable laminates comprising a core of several layers each of different fibrous materials, e.g. meltblown fibers, spunbond fibers, containing multicomponent fibers having a core comprising a first polymer having a first melt temperature and a sheath comprising a second polymer having a second melt temperature; and a web of an elastomeric material as top and bottom surfaces to form said laminate.

D. Fluid-Absorbent Article Construction

The present invention further relates to the joining of the components and layers, films, sheets, tissues or substrates mentioned above to provide the fluid-absorbent article. At least two, preferably all layers, films, sheets, tissues or substrates are joined.

Suitable fluid-absorbent articles include a single- or multiple fluid-absorbent core-system. Preferably fluid-absorbent articles include a single fluid-absorbent core-system.

Suitable fluid-storage layers of the fluid-absorbent core (80) comprising 0 to 20% by weight fibrous material and from 80 to 100% by weight a water-absorbent polymer material. In case of fibrous material present, the fibrous materials homogeneously or in-homogeneously mixed with water-absorbent polymer particles. Suitable fluid-storage layers of the fluid-absorbent core including a layered fluid-absorbent core-system comprising 100% by weight of water-absorbent polymer material orhomogeneous or in-homogeneous mixtures of fibrous materials and water-absorbent polymer particles.

In order to immobilize the water-absorbent polymer particles, the adjacent layers are fixed by the means of thermoplastic materials, thereby building connections throughout the whole surface or alternatively in discrete areas of junction. For the latter case, cavities or pockets are built carrying the water-absorbent particles. The areas of junction may have a regular or irregular pattern, e.g. aligned with the longitudinal axis of the fluid-absorbent core or in a pattern of polygons, e.g. pentagons or hexagons. The areas of junction itself may be of rectangular, circular or squared shape with diameters between about 0.5 mm and 2 mm. Fluid-absorbent articles comprising areas of junction show a better wet strength.

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by Bostik, Henkel or Fuller.

In order to ensure wicking of applied body fluids, preferred fluid-absorbent article show channels for better transport. Channels are formed by compressional forces of e.g. the top sheet against the fluid-absorbent core. Compressive forces may be applied e.g. by heat-treatment between two heated calendar rollers. As an effect of compression both on top sheet and fluid-absorbent core deform such that a channel is created. Body fluids are flowing along this channel to places where they are absorbed and leakage is prevented. Otherwise, compression leads to higher density; this is the second effect of the channel to canalize insulted fluids. Additionally, compressive forces on diaper construction improve the structural integrity of the fluid-absorbent article.

Suitable fluid-absorbent articles according to the invention preferably contain no acquisition distribution layer (D).

According to the invention a fluid-absorbent article, comprising
  (A) an upper liquid-pervious layer (89),
  (B) a lower liquid-impervious layer (83), and a fluid-absorbent core (80), comprising at least one layer, comprising from 0 to 20% by weight fibrous material and from 80 to 100% by weight a water-absorbent polymer material, based on the sum of water-absorbent polymer material and fibrous material;
  having a first intake time of 15 seconds or less by the hanging U-shape test (HUS).

The fluid-absorbent article according to the invention preferably containing no curly fibers, or fluff.

According to the invention it is preferred that the water-absorbent polymer material of the at least one layer of the absorbent core (80) comprises only one water absorbent polymer, preferably fast superabsorbent.

Figure 18:
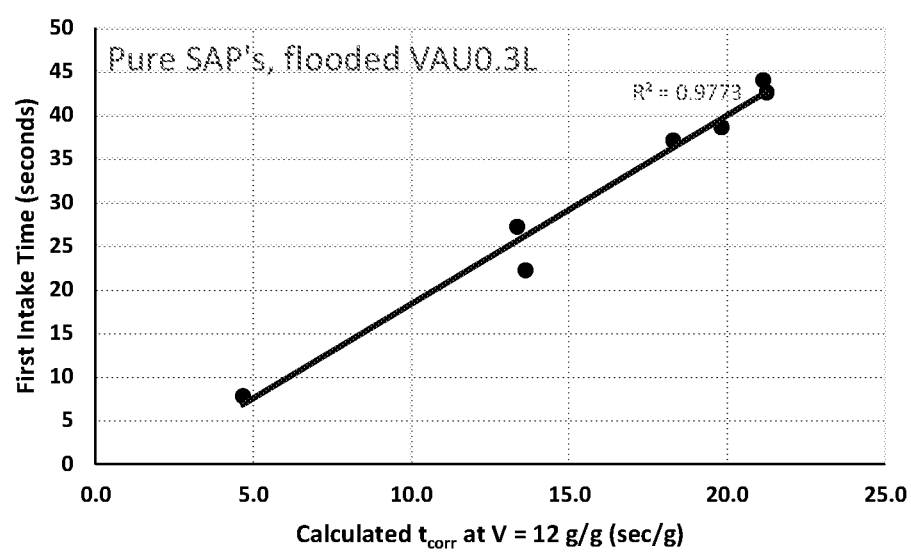
FIG. 18 illustrates the relationship between the first intake time and the $t_{corr}$ value (flooded VAUL, 0.3 psi).

A fluid absorbent article according to the invention comprising a single component water-absorbent polymer material (without aquisition distribution layer (D), curly fiber, or cellulosic fluff), preferably fast superabsorbent, has a first intake time determined with the hanging U-shape test (HUS) correlating to the $t_{corr}$ value of the water-absorbent material. A linear relationship between the first intake time and the $t_{corr}$ value can be found. For a desired first intake time of less than 15 seconds the $t_{corr}$ (flooded VAUL, 0.3 psi) value should be 12 sec/g or less, for less than 12.5 seconds first intake time the $t_{corr}$ value (flooded VAUL, 0.3 psi) should be less than 7.5 sec/g, and less than 10 seconds for the first intake time the $t_{corr}$ value (flooded VAUL, 0.3 psi) should be less than 6 sec/g. This is illustrated by FIG. 18

According to the invention a fluid absorbent article comprising a blend of at least two water absorbent polymer materials comprising at least 20 wt.-% of a fast superabsorbent and 80 wt.-% or less of second superabsorbent, without acquisition distribution layer (D), curly fiber, or cellulosic fluff behave as if only the fast superabsorbent is present in respect to the first intake time determined with the hanging U-shape test (HUS).

A fluid absorbent article according to the invention preferably has a first intake time determined with the hanging U-shape test has a first intake time of 12 seconds or less, more preferably of 9 seconds or less, most preferably of 7 seconds or less.

According to the invention a fluid-absorbent article without an acquisition distribution layer (D) has a rewet of not more than 43 g, preferably below 35 g.

According to the invention wherein an acquisition distribution layer (D) is present between (89) and (80) the rewet is not more than 25 g, preferably below 13 g.

The inventive absorbent articles provide a combination of a very fast intake time of below 12 s (determined with the hanging U-shape test) with rewet values below 43 g (without acquisition distribution layer) and not more than 25 g with an acquisition distribution layer of at least 60 gsm. The inventive absorbent articles combine a fast intake to prevent leakage and a low rewet, especially to ensure the dry feeling/dryness of the wearer.

Furthermore, as the inventive absorbent article even ensures dryness without acquisition distribution layer, it is very thin (in z-direction) and less noticeable. A very thin inventive absorbent article also comprises only an absorbent core (80) containing one layer (91) of water-absorbent polymer material.

In order to increase the control of body fluid absorption it may be advantageous to add one or more further fluid-absorbent cores. The addition of a second fluid-absorbent core to the first fluid-absorbent core offers more possibilities in body fluid transfer and distribution. Moreover higher quantities of discharged body fluids can be retained. Having the opportunity of combining several layers showing different water-absorbent polymer concentration and content, it is possible to reduce the thickness of the fluid-absorbent article to a minimum even if there are several fluid-absorbent cores included.

Methods:

The measurements should, unless stated otherwise, be carried out at an ambient temperature of 23±2° C. and a relative atmospheric humidity of 50±10%. The water-absorbent polymers are mixed thoroughly before the measurement.

The "WSP" standard test methods are described in: "Standard Test Methods for the Nonwovens Industry", jointly issued by the "Worldwide Strategic Partners" EDANA (European Disposables and Nonwovens Association, Avenue Eugene Plasky, 157, 1030 Brussels, Belgium, www.edana.org) and INDA (Association of the Nonwoven Fabrics Industry, 1100 Crescent Green, Suite 115, Cary, N.C. 27518, U.S.A., www.inda.org). This publication is available both from EDANA and INDA.

Absorbency Under No Load (AUNL)

The absorbency under no load of the water-absorbent polymer particles is determined analogously to the EDANA recommended test method No. WSP 242.3 (11) "Gravimetric Determination of Absorption Under Pressure", except using a weight of 0.0 g/cm$^2$ instead of a weight of 21.0 g/cm$^2$.

Absorbency Under Load (AUL)

The absorbency under load of the water-absorbent polymer particles is determined by the EDANA recommended test method No. WSP 242.3 (11) "Gravimetric Determination of Absorption Under Pressure"

Absorbency Under High Load (AUHL)

The absorbency under high load of the water-absorbent polymer particles is determined analogously to the EDANA recommended test method No. WSP 242.3 (11) "Gravimetric Determination of Absorption Under Pressure", except using a weight of 49.2 g/cm$^2$ instead of a weight of 21.0 g/cm$^2$.

Accelerated Aging Test

Measurement 1 (Initial color): A plastic dish with an inner diameter of 9 cm is overfilled with superabsorbent polymer particles. The surface is flattened at the height of the petri dish lip by means of a knife and the CIE color values and the HC 60 value are determined.

Measurement 2 (after aging): A plastic dish with an inner diameter of 9 cm is overfilled with superabsorbent polymer particles. The surface is flattened at the height of the petri dish lip by means of a knife. The plastic dish (without a cover) is then placed in a humidity chamber at 60° C. and a relative humidity of 86%. The plastic dish is removed from the humidity chamber after 7, 14, and 21 days, cooled down to room temperature and the CIE color values are determined.

Basis Weight

The basis weight is determined at discrete regions of the fluid-absorbent core: the front overall average; the insult zone and the back overall average.

The article nonwoven face is pinned upwards onto the inspection table. Then an insult point is marked on the fluid-absorbent article. The insult point is marked on the article accordingly with regard to the type and gender of the diaper to be tested (i.e. in the centre of the fluid-absorbent core for girl, 2.5 cm towards the front for unisex and 5 cm towards the front for boy).

Then lines for the following zones are marked on the fluid-absorbent article in dependence of the diaper to be tested, e. g. for boy diapers:

for the front overall average zone 5.5 cm forward of the center of the core to the front distal edge of the core;

for the insult zone 5.5 cm forward and 0.5 cm backwards of the center of the core;

for the back overall average zone 0.5 cm backward of the center of the core to the rear distal edge of the core The length (ZL) and width (ZW) of each zone is recorded. Then the previously marked zones are cut out and the record weight (ZWT) of each zone is taken.

Before calculating the basis weight, the area of each zone must first be calculated as follows:

$$\text{Zonal Area (ZA)}=(ZW \times ZL)[\text{cm}^2]$$

The Zonal Basis Weight (ZBW) is then calculated as follows:

$$\text{Zonal Basis Weight (ZBW)}=ZWT/(ZW*ZL)*10000[\text{g/m}^2]$$

For example, if ZW is 6 cm, ZL is 10 cm and ZWT is 4.5 g the Zonal Basis Weight (ZBW) is:

$$ZBW=4.5 \text{ g}/(6 \text{ cm} \times 10 \text{ cm})*10000=750 \text{ gsm}$$

Conversion of Gram per Square Centimeter g/cm$^2$ to Gram per Square Meter g/m$^2$:

$$10\,000 \times \text{g/cm}^2=\text{g/m}^2$$

Conversion of Gram per Square Meter g/m$^2$ to Gram per Square Centimeter g/cm$^2$:

$$0.0001 \times \text{g/m}^2=\text{g/cm}^2$$

BET Method (Surface Area)

The area/weight ratio was obtained in the following manner. The powdered resin was deaerated at 100° C. for 960 minutes under vacuum, and the specific surface area was measured by the BET (Brunauer-Emmett-Teller) absorption method based on krypton gas while cooling with liquid nitrogen.

Bulk Density

The bulk density of the water-absorbent polymer particles is determined by the EDANA recommended test method No. WSP 250.3 (11) "Gravimetric Determination of Density".

Centrifuge Retention Capacity (CRC)

The centrifuge retention capacity of the water-absorbent polymer particles is determined by the EDANA recommended test method No. WSP 241.3 (11) "Free Swell Capacity in Saline, After Centrifugation", wherein for higher values of the centrifuge retention capacity larger tea bags have to be used.

Color Value (CIE Color Numbers [L, a, b])

Measurement of the color value is done by means of a colorimeter model "LabScan XE S/N LX17309" (HunterLab; Reston; U.S.A.) according to the CIELAB procedure (Hunterlab, Volume 8, 1996, Issue 7, pages 1 to 4). Colors are described by the coordinates L, a, and b of a three-dimensional system. L characterizes the brightness, whereby L=0 is black and L=100 is white. The values for a and b describe the position of the color on the color axis red/green resp. yellow/blue, whereby positive a values stand for red colors, negative a values for green colors, positive b values for yellow colors, and negative b values for blue colors.

The measurement of the color value is in agreement with the tristimulus method according to DIN 5033-6.

Extractables

The level of extractable constituents in the water-absorbent polymer particles is determined by the EDANA recommended test method No. WSP 270.3 (11) "Extractables".

Free Swell Capacity (FSC)

The free swell capacity of the water-absorbent polymer particles is determined by the EDANA recommended test method No. WSP 240.3 (11) "Free Swell Capacity in Saline, Gravimetric Determination", wherein for higher values of the free swell capacity larger tea bags have to be used.

Free Swell Rate (FSR)

1.00 g (=W1) of the dry water-absorbent polymer particles is weighed into a 25 ml glass beaker and is uniformly distributed on the base of the glass beaker. 20 ml of a 0.9% by weight sodium chloride solution are then dispensed into a second glass beaker, the content of this beaker is rapidly added to the first beaker and a stopwatch is started. As soon as the last drop of salt solution is absorbed, confirmed by the disappearance of the reflection on the liquid surface, the stopwatch is stopped. The exact amount of liquid poured from the second beaker and absorbed by the polymer in the first beaker is accurately determined by weighing back the second beaker (=W2). The time needed for the absorption, which was measured with the stopwatch, is denoted t. The disappearance of the last drop of liquid on the surface is defined as time t.

The free swell rate (FSR) is calculated as follows:

$$FSR\ [g/gs] = W2/(W1 \times t)$$

When the moisture content of the hydrogel-forming polymer is more than 3% by weight, however, the weight W1 must be corrected for this moisture content.

Hanging U-Shape Test (HUS)

Figure 19:
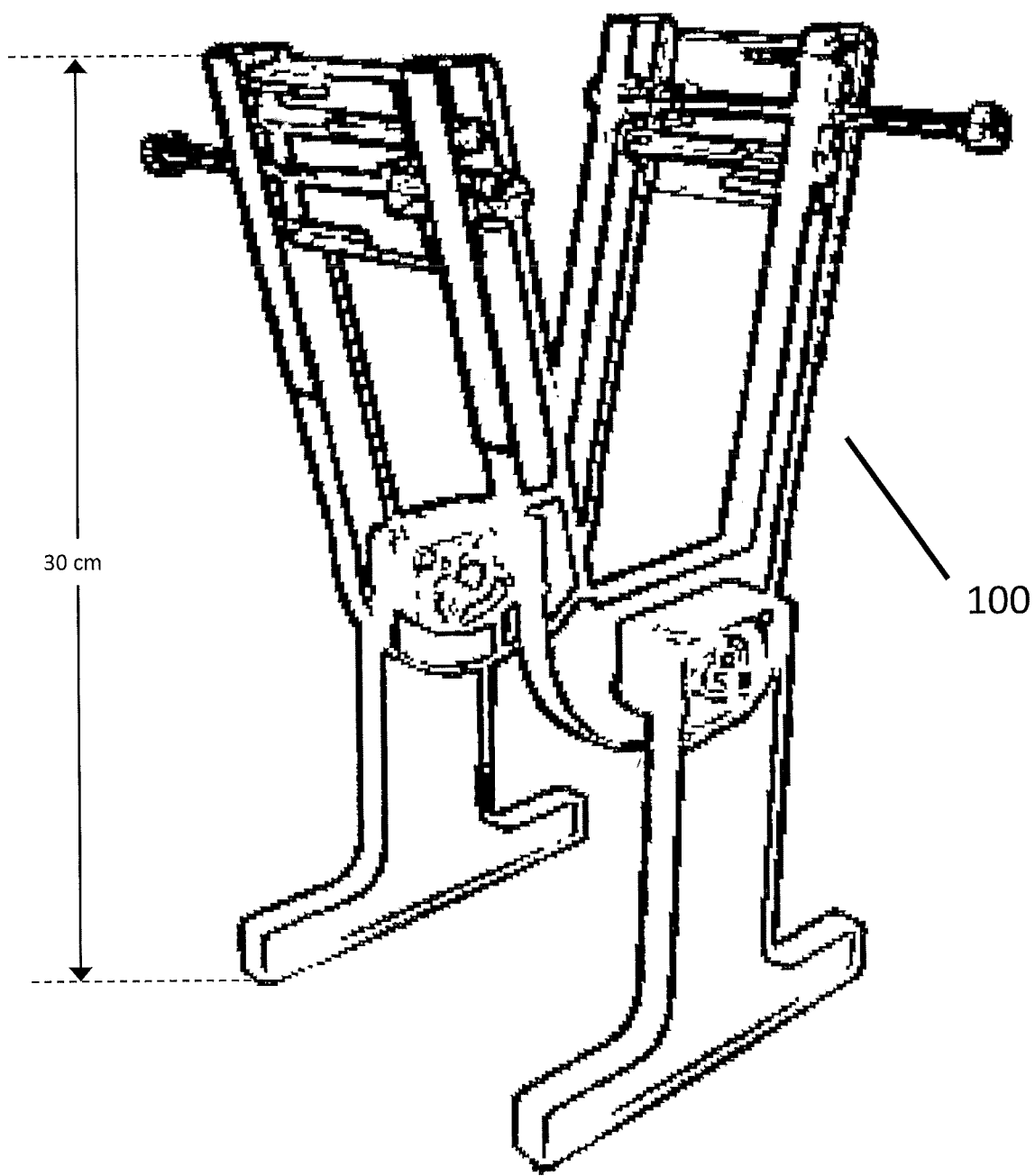
FIG. 19 A is a schematic view of a hole unit without diaper.
Figure 19:
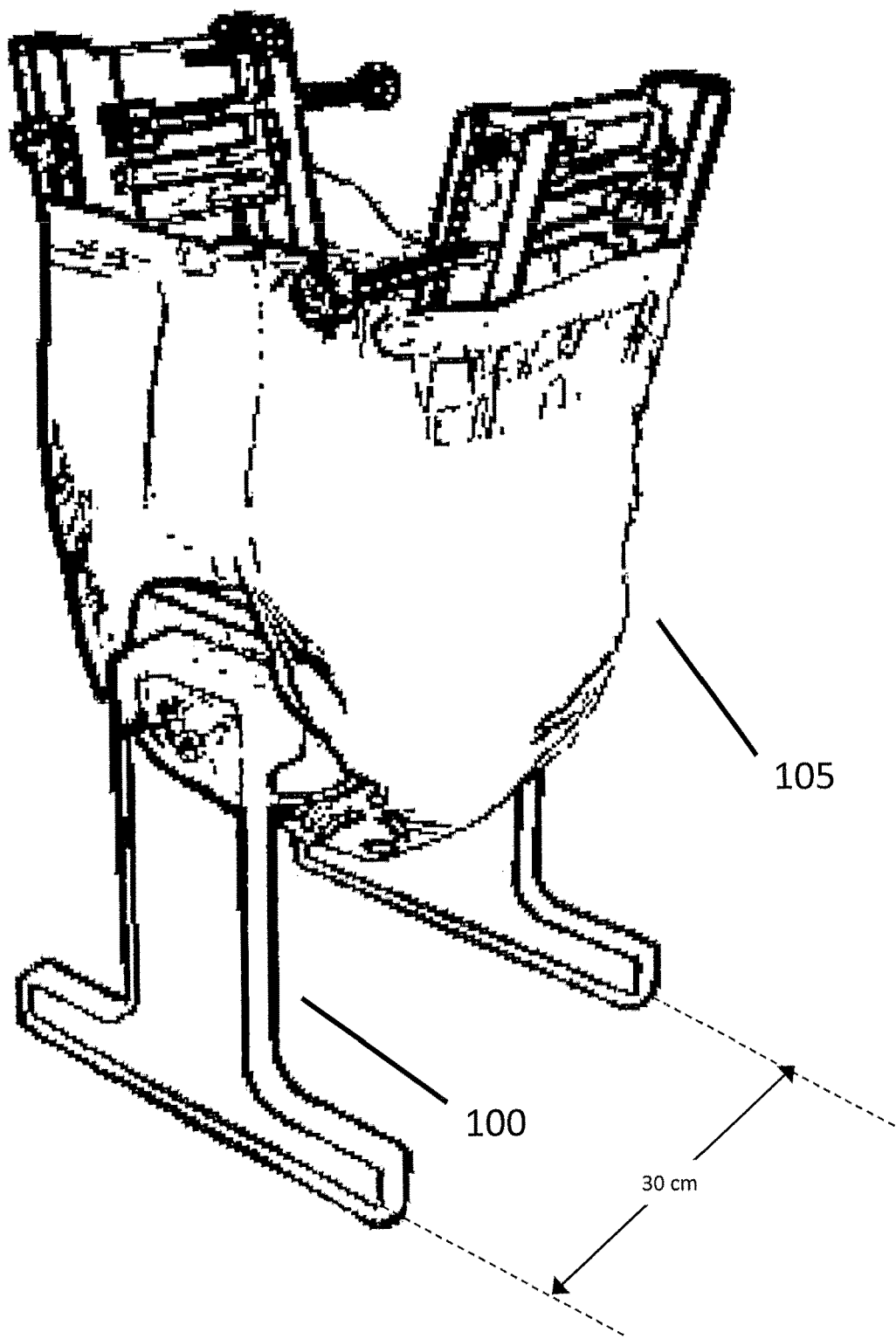
Figure 19:
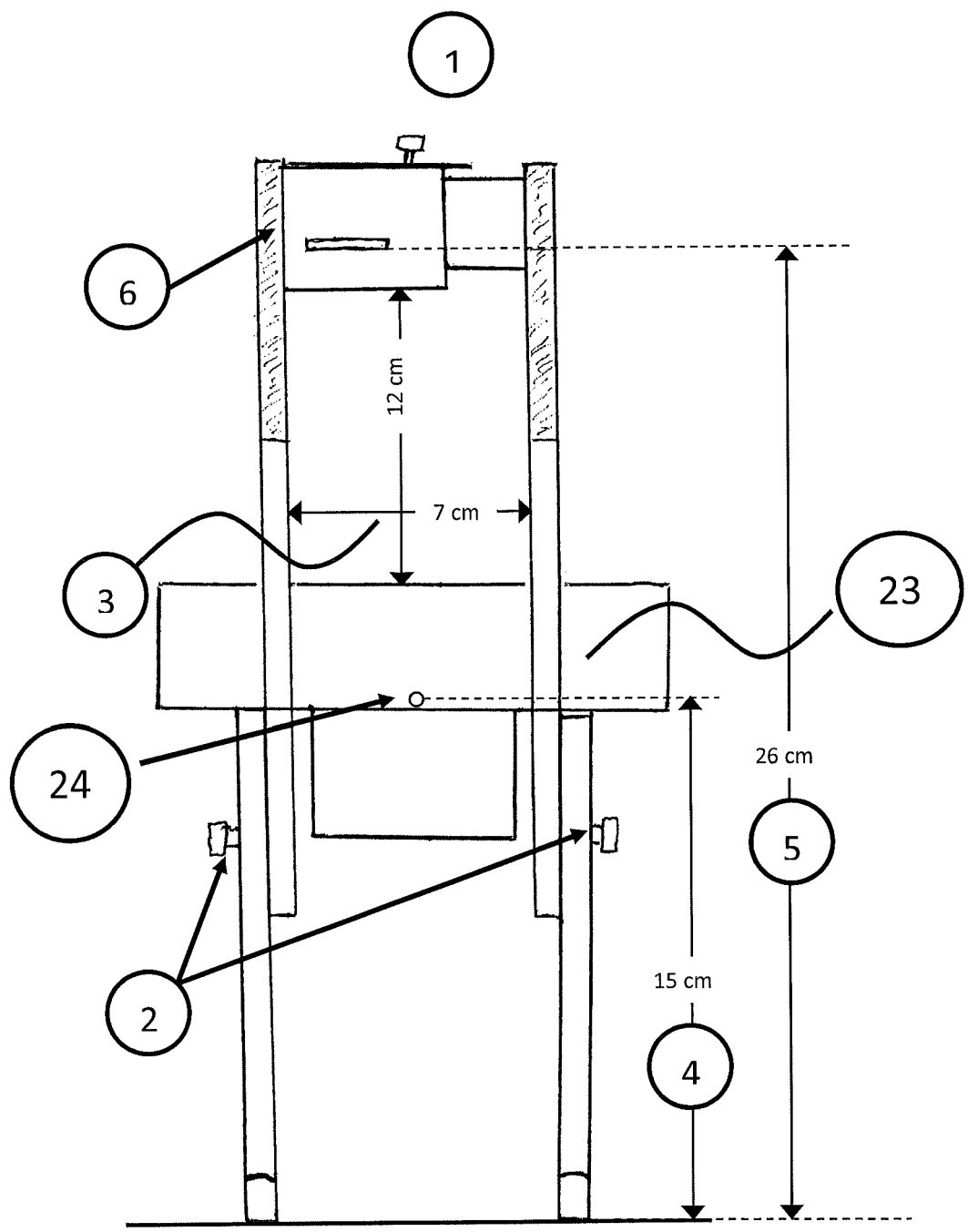
Figure 19D:
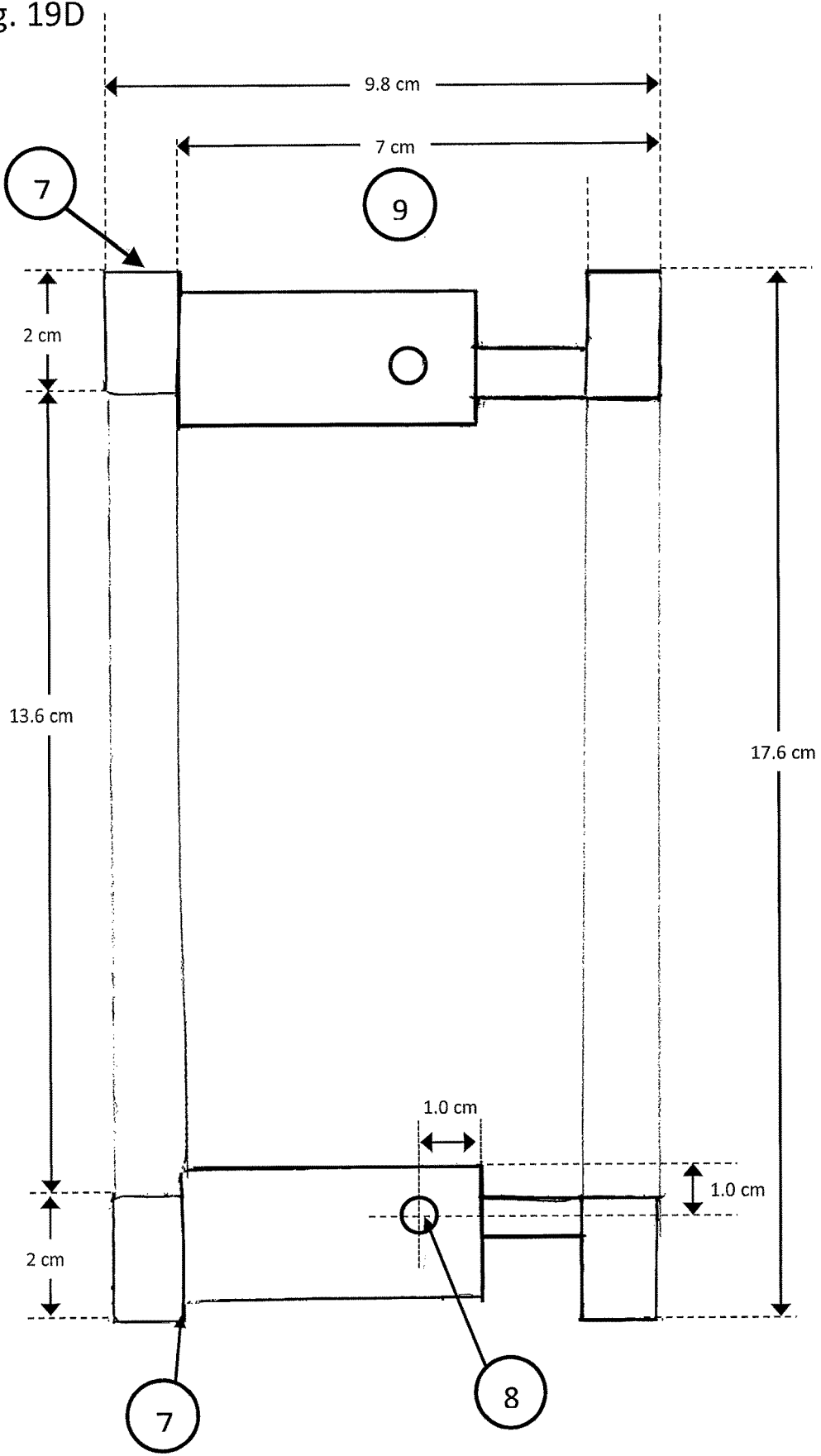
Figure 19:
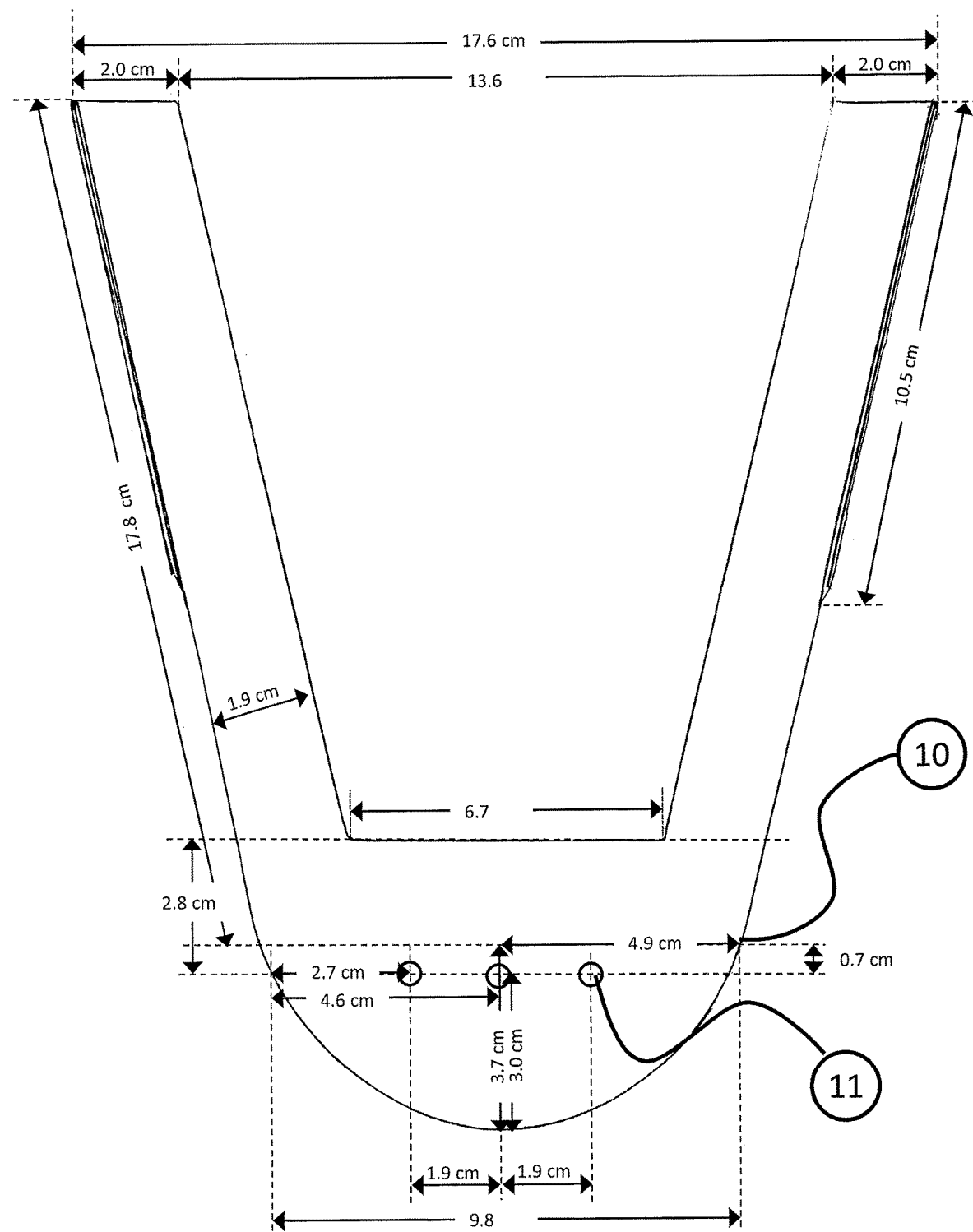
Figure 19:
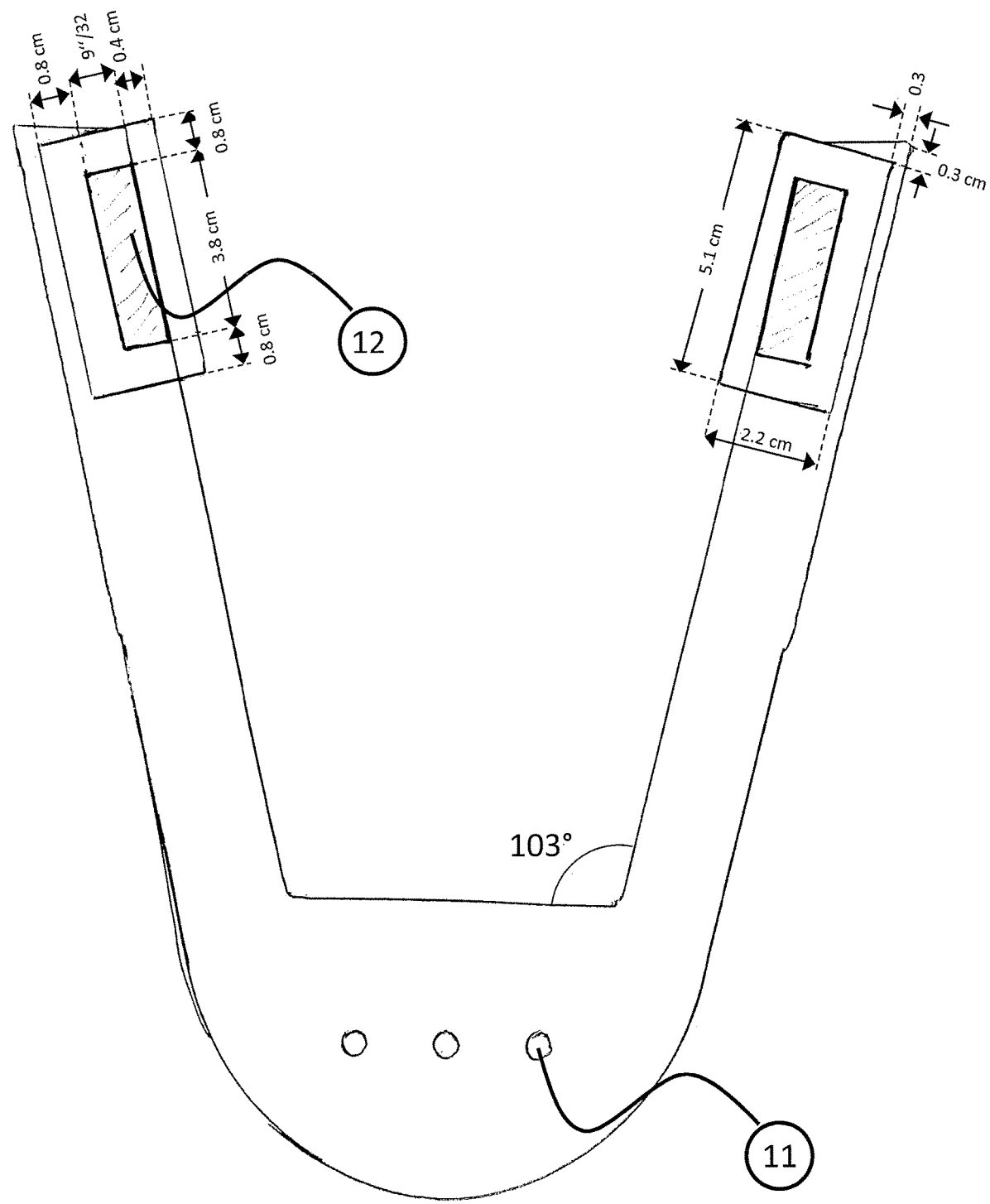
Figure 19:
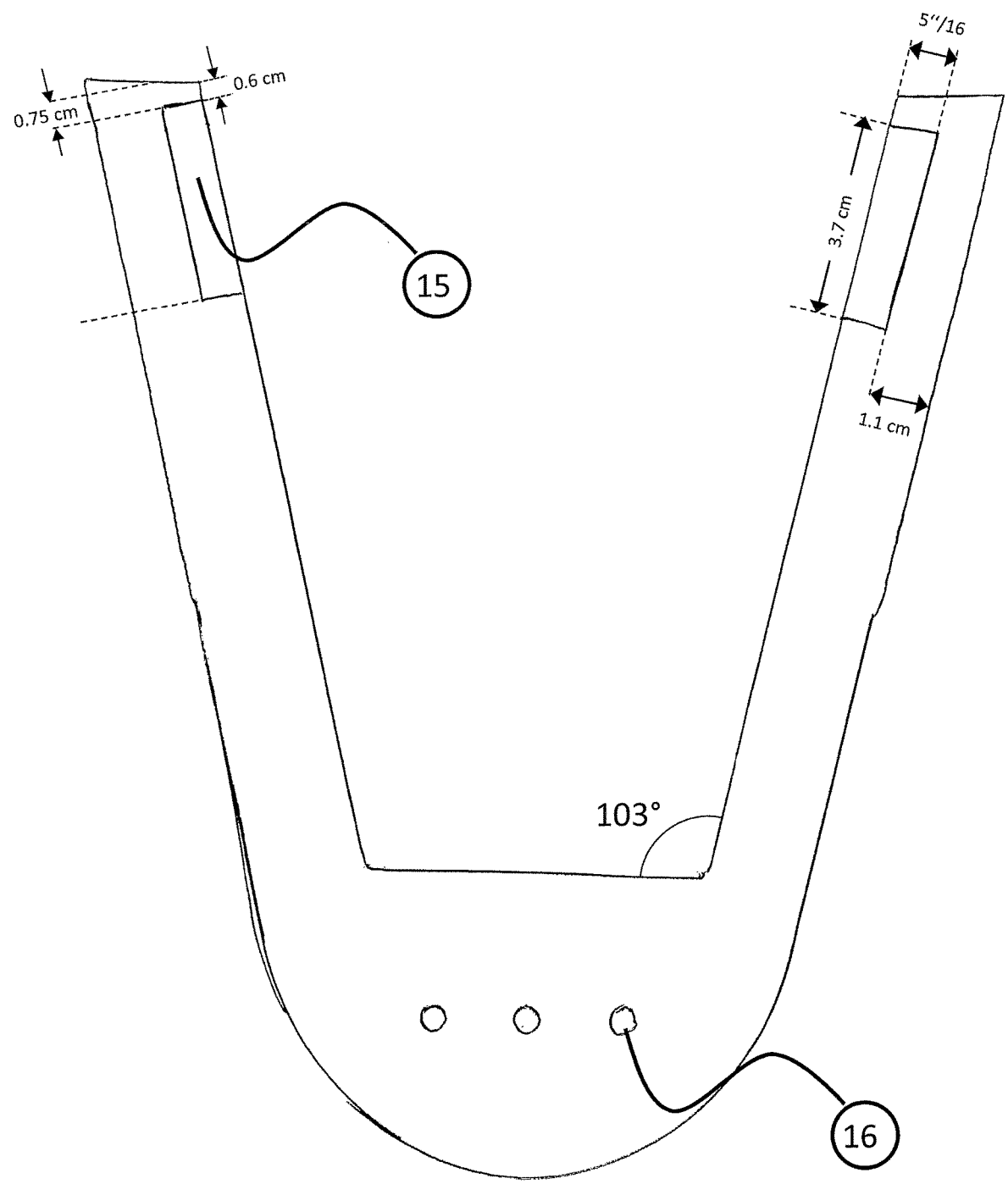
Figure 19:
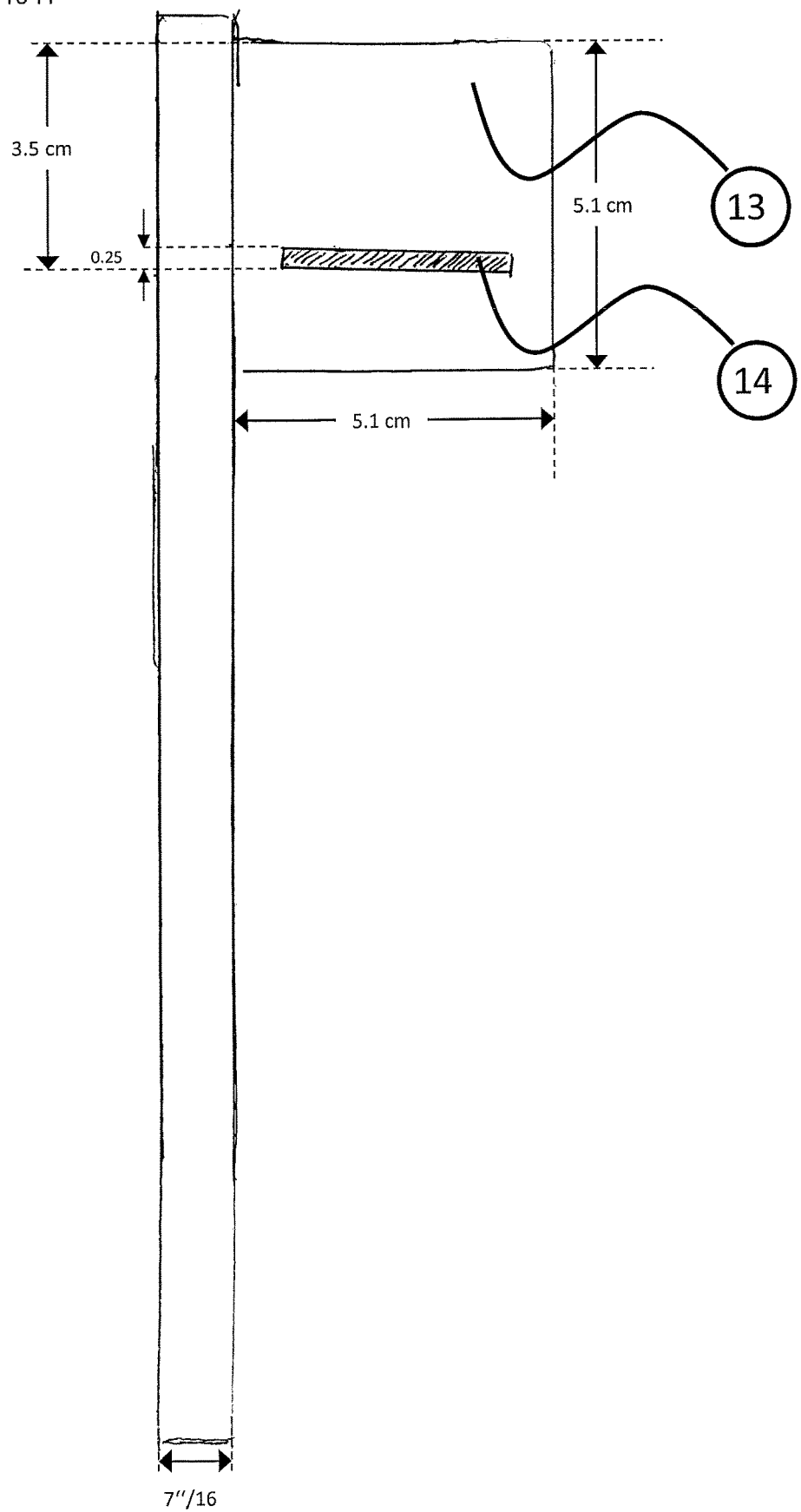
Figure 19:
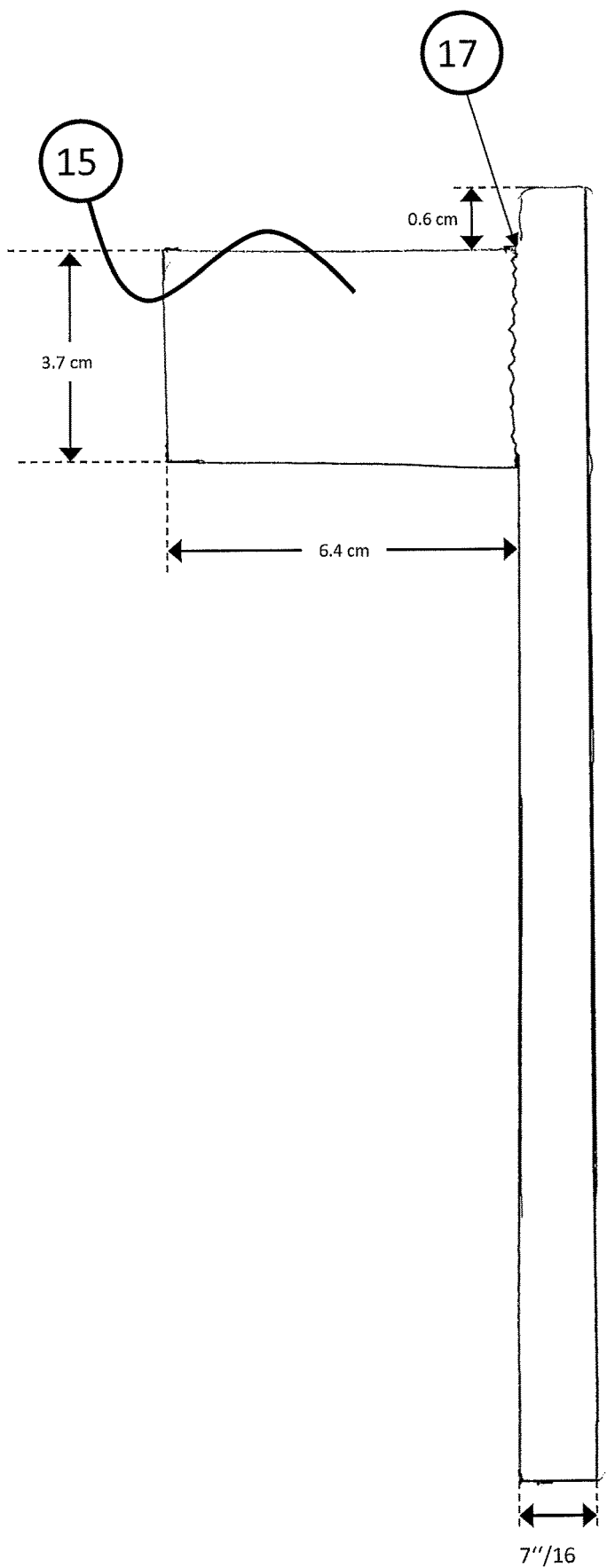
Figure 19:
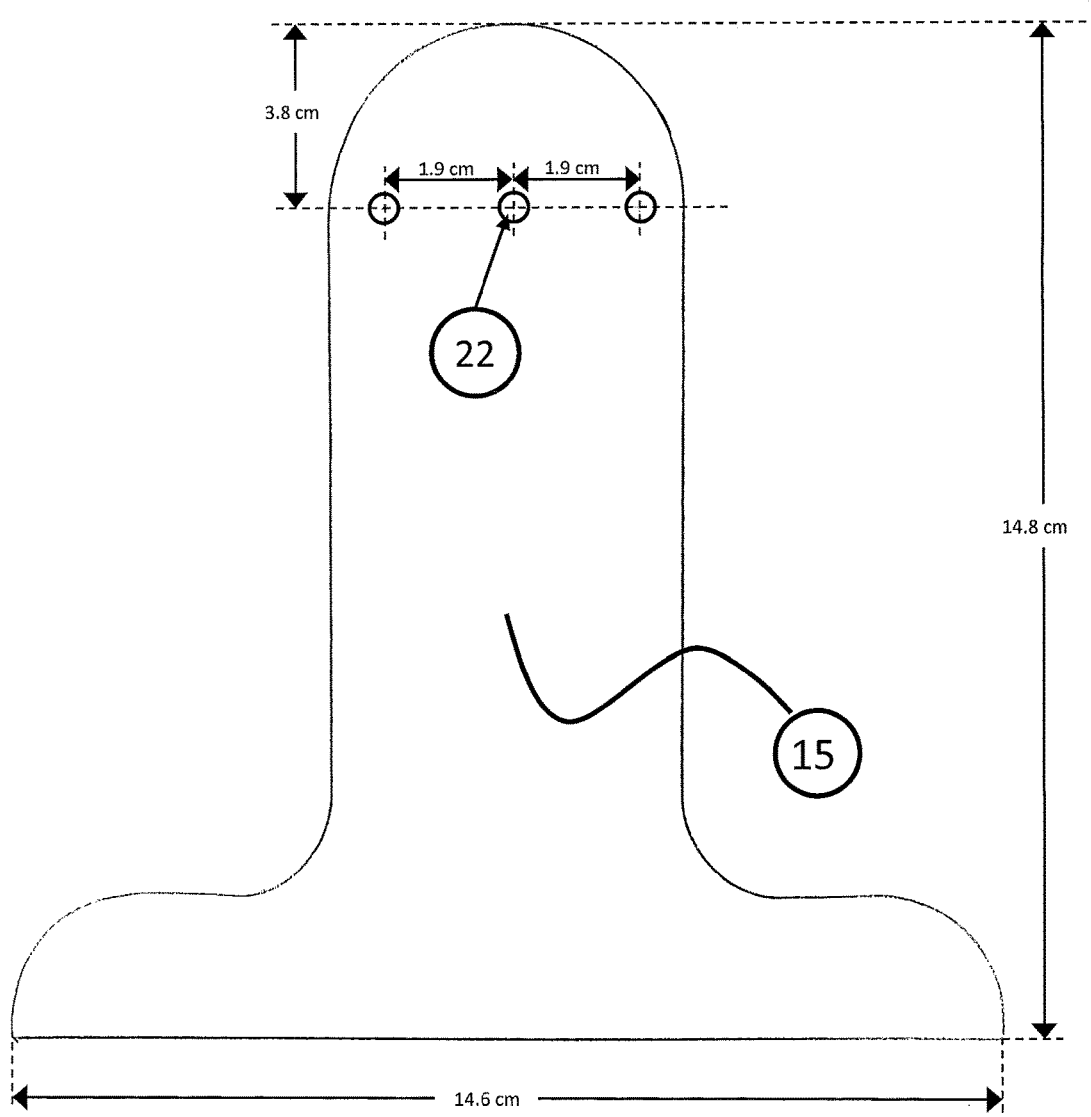
Figure 19:
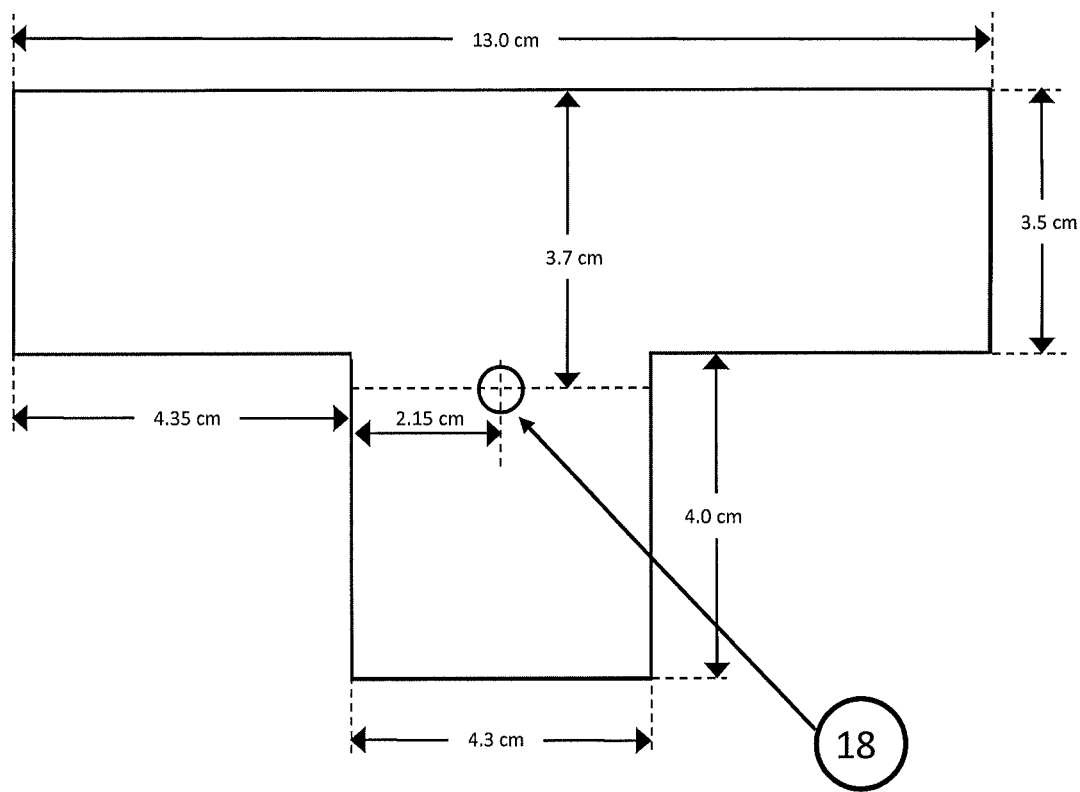
Figure 19:
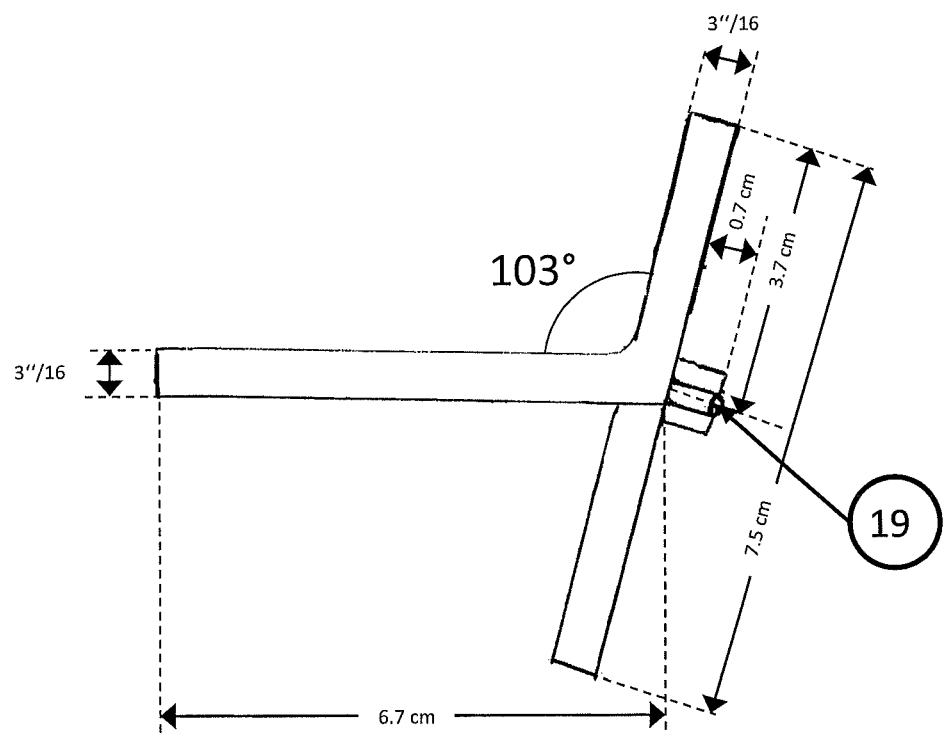
Figure 19:
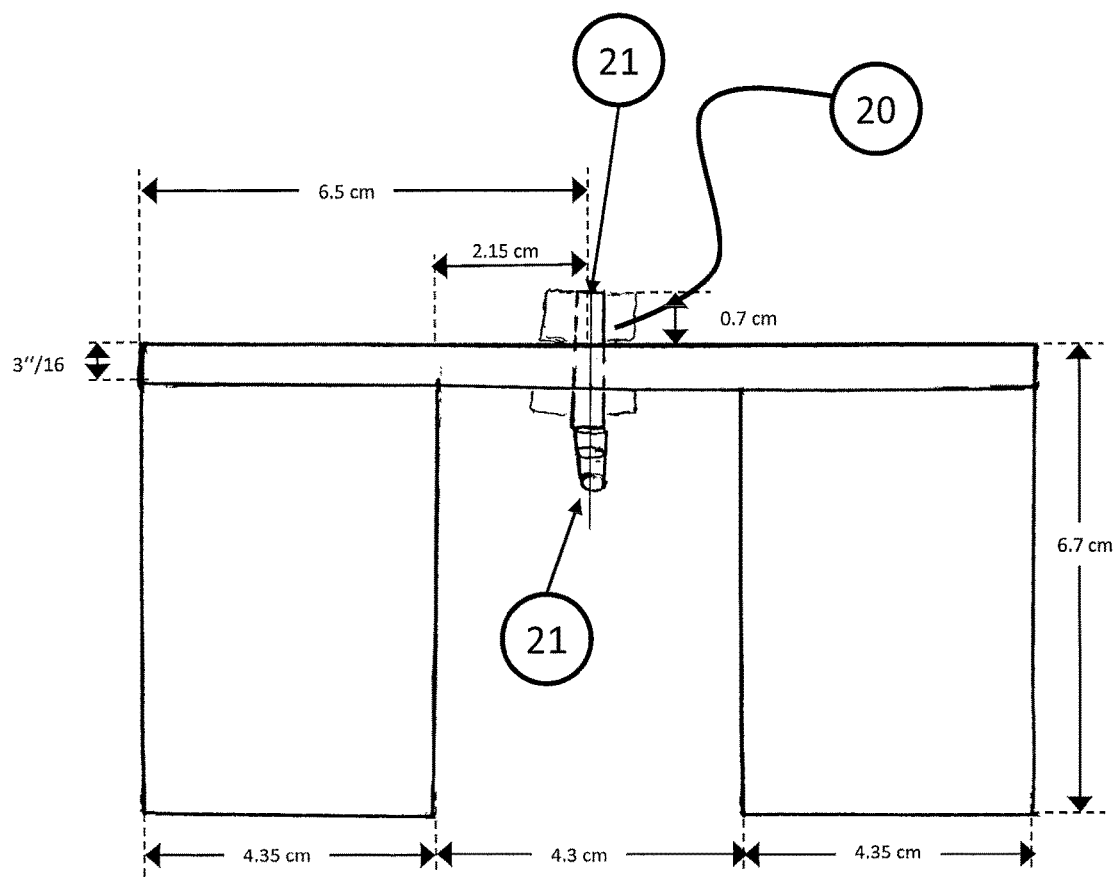

The HUS equipment is shown in FIG. 19 A to M

The figures show the following:

FIG. 19 A: Hole unit without diaper
FIG. 19 B: Hole unit with diaper
FIG. 19 C: Front view whole Unit
FIG. 19 D: Top view
FIG. 19 E: Side view-both uprights, outside
FIG. 19 F: Inside view, right upright
FIG. 19 G: Inside view, left upright
FIG. 19 H: Front view, right upright
FIG. 19 I: Front view, reft upright
FIG. 19 J: Side view, both legs
FIG. 19 K: Self Centering Dosing Plate, front view
FIG. 19 L: Self Centering Dosing Plate, side view
FIG. 19 M: Self Centering Dosing Plate, top view The reference numerals have the following meanings in FIG. 19 A to M:

1. ¼"-20-0.5" Nylon Set Screw
2. ¼"-20-1" Nylon Screw
3. fit for size 4 diaper
4. height to dosing hole center
5. height to top of diaper waist band
6. hock fastening tape
7. Hook tape
8. Holes for (1) Nylon Screw
9. Size 4 width
10. Begin Curve holes Center Line
11. Holes are ¼" diameter, Thread=20 TPI (20 Thread per inch)
12. Slot to accept 5/16" plate from left upright
13. Rectangular box capable of accepting the 5/16" plate (15) from the left upright (front, back). Its mounted each on the front and back of the right upright
14. A black mark, 0.25 cm thick, is placed on box (13), 3.5 cm from the top of the box. This mark is used to indicate Size 4 diaper placement
15. 5/16" Acrylic plates
16. 2 times Nr.2
17. Solvent welded
18. Ø 0.375 cm dosing hole
19. Ø 0.375 cm dosing hole in nut, that extends out 0.7 cm from plate face
20. Nut
21. Hose adapter to pump
22. Ø 6 mm holes
23. Self Centering Dosing Plate
24. dosing hole center The U-shape test is descriped for size 4 diapers:

The diapers are placed in a HUS unit (FIG. 19 A) with the edges of the diaper 3.5 cm from the top of the testing unit (FIG. 19B, C) (at the black mark (14)). The dosing is set at 15.5 cm from the top of the testing unit, or 12 cm from the top of the diaper following the angle of the uprights, through a 3.75 mm saline dosing port (18). The saline dosing port (18) is connected to a pump which delivers the 35° C. saline at 15 g/second. For this size diaper a dosing mass of 4×75 g is used. Each intake time (first, second, third, fourth, each dose of 75 g) is measured from the start of the dosing until all the saline is absorbed by the diaper. Wait time between each dose was 10 minutes from the start of the dose.

The test can be adjusted to different diaper sizes. Therefore the black mark (14) is moved up for larger diapers and down for smaller diapers to ensure a comparable distance between the diaper and the dosing port. The width of the testing unit is made to be adjustable, so the gap between the uprights can be moved in for smaller diapers or made bigger for larger size diapers. Usually the width is adjusted to 6 cm for size 2 diapers, for all other size diapers, the width keep as 7 cm.

For different size diapers, the dosing amounts are different:

Size 2, 50 g×4
Size 3, 60 g×4
Size 4, 75 g×4
Size 5, 85 g×4
Size 6, 90 g×4

Mean Sphericity or Roundness

The mean sphericity is determined with the Camziser® image analysis system (Retsch Technology GmbH; Haan; Germany) using the particle diameter fraction from 100 to 1,000 µm.

Moisture Content

The moisture content of the water-absorbent polymer particles is determined by the EDANA recommended test method No. WSP 230.3 (11) "Mass Loss Upon Heating".

Particle Size Distribution

The particle size distribution of the water-absorbent polymer particles is determined by the EDANA recommended test method No. WSP 220.3 (11) "Particle Size Distribution".

The average particle diameter ($d_{50}$) here is the value of the mesh size which gives rise to a cumulative 50% by weight.

The degree of polydispersity α of the particle size particle is calculated by $$\alpha = (d_{84.13} - d_{15.87})/(2 \times d_{50})$$

wherein $d_{15.87}$ and $d_{84.13}$ is the value of the mesh size which gives rise to a cumulative 15.87% respective 84.13% by weight.

Residual Monomers

The level of residual monomers in the water-absorbent polymer particles is determined by the EDANA recommended test method No. WSP 210.3-(11) "Residual Monomers".

Rewet Value

This test consists of multiple insults of 0.9 wt. % NaCl solution in deionized water. The rewet is measured by the amount of fluid the article released under pressure. The rewet is measured after each insult.

The fluid-absorbent article is clamped nonwoven side upward onto the inspection table. The insult point is marked accordingly with regard to the type and gender of the diaper to be tested (i.e. in the centre of the core for girl, 2.5 cm towards the front for unisex and 5 cm towards the front for boy). A separatory funnel is positioned above the fluid-absorbent article so that the spout is directly above the marked insult point.

For the primary insult 100 g of aqueous saline solution (0.9% by weight) is poured into the fluid-absorbent article via the funnel in one shot. The liquid is allowed to be absorbed for 10 minutes, and after that time the stack of 10 filter papers (Whatman®) having 9 cm diameter and known dry weight (D1) is placed over the insult point on the fluid-absorbent article. On top of the filter paper, the 2.5 kg weight with 8 cm diameter is added. After 2 minutes have elapsed the weight is removed and filter paper reweighed giving the wet weight value (D2).

The rewet value is calculated as follows:

$$RV\ [g] = D2 - D1$$

For the rewet of the secondary insult the procedure for the primary insult is repeated. 50 g of aqueous saline solution (0.9% by weight) and 20 filter papers are used.

For the rewet of the tertiary and following insults the procedure for the primary insult is repeated. For each of the following insults $3^{rd}$, $4^{th}$ and $5^{th}$ 50 g of aqueous saline solution (0.9% by weight) and 30, 40 and 50 filter papers respectively are used.

Rewet Under Load (RUL)

The test determines the amount of fluid a fluid-absorbent article will release after being maintained at a pressure of 0.7 psi (49.2 g/cm²) for 10 min following multiple separate insults. The rewet under load is measured by the amount of fluid the fluid-absorbent article releases under pressure. The rewet under load is measured after each insult.

The fluid-absorbent article is clamped nonwoven side upward onto the inspection table. The insult point is marked accordingly with regard to the type and gender of the diaper to be tested (i.e. in the centre of the core for girl, 2.5 cm towards the front for unisex and 5 cm towards the front for boy). A 3.64 kg circular weight (10 cm diameter) having a central opening (2.3 cm diameter) with perspex tube is placed with on the previously marked insult point.

For the primary insult 100 g of aqueous saline solution (0.9% by weight) is poured into the perspex tube in one shot. Amount of time needed for the fluid to be fully absorbed into the fluid-absorbent article is recorded. After 10 minutes have elapsed, the load is removed and the stack of 10 filter papers (Whatman®) having 9 cm diameter and known dry weight (W1) is placed over the insult point on the fluid-absorbent article. On top of the filter paper, the 2.5 kg weight with 8 cm diameter is added. After 2 minutes have elapsed the weight is removed and filter paper reweighed giving the wet weight value (W2).

The rewet under load is calculated as follows:

$$RUL\ [g] = W2 - W1$$

For the rewet under load of the secondary insult the procedure for the primary insult is repeated. 50 g of aqueous saline solution (0.9% by weight) and 20 filter papers are used.

For the rewet under load of the tertiary and following insults the procedure for the primary insult is repeated. For each of the following insults $3^{rd}$, $4^{th}$ and $5^{th}$ 50 g of aqueous saline solution (0.9% by weight) and 30, 40 and 50 filter papers respectively are used.

Saline Flow Conductivity (SFC)

The saline flow conductivity is, as described in EP 0 640 330 A1, determined as the gel layer permeability of a swollen gel layer of water-absorbent polymer particles, although the apparatus described on page 19 and in FIG. 8 in the aforementioned patent application was modified to the effect that the glass frit (40) is no longer used, the plunger (39) consists of the same polymer material as the cylinder (37) and now comprises 21 bores having a diameter of 9.65 mm each distributed uniformly over the entire contact surface. The procedure and the evaluation of the measurement remains unchanged from EP 0 640 330 A1. The flow rate is recorded automatically.

The saline flow conductivity (SFC) is calculated as follows:

$$SFC\ [cm^3 s/g] = (Fg(t=0) \times L0)/(d \times A \times WP),$$

where $Fg(t=0)$ is the flow rate of NaCl solution in g/s, which is obtained by means of a linear regression analysis of the $Fg(t)$ data of the flow determinations by extrapolation to t=0, L0 is the thickness of the gel layer in cm, d is the density of the NaCl solution in g/cm³, A is the surface area of the gel layer in cm² and WP is the hydrostatic pressure over the gel layer in dyn/cm².

Flooded Volumetric Absorbency Under (No) Load (Flooded VAUNL and Flooded 0.3 Psi VAUL)

In an open container that is 10×10 cm is placed an 8.5×8.5 cm mesh with holes 0.5×0.5 cm in size. The mesh is used to keep the bottom of the test cell off of the container bottom so that fluid can easily flow into the test cell from the bottom. The test cell consists of a plastic tube 8 cm tall with an inside diameter of 6.01 cm and a 400 mesh stainless steel mesh affixed to the bottom. The superabsorbent to be tested, 2 grams, is evenly distributed on the bottom of the test cell and then placed in the test container (on top of the aforementioned mesh). A circle of 10 gsm nonwoven with the same diameter as the inside of the test cell is placed on top of the SAP. Then a perforated load distribution plate attached to a linear transducer probe is placed on top of the nonwoven, this is the no-load condition (flooded VAUNL). For the flooded 0.3 psi VAUL the perforated load distribution plate is replaced with an acrylic pedestal consisting 100 mesh stainless steel screen affixed to a perforated disk with outside diameter is 6.00 cm to fit inside the test cell and a shaft to hold a weight away from the disk. The total weight of the screen, disk, shaft, and added weight is 600 g which delivers a confining pressure of 0.3 psi. The linear transducer is interfaced with a computer such that the height can be measured as a function of time. Height readings are taken every second for 30 minutes and converted to a volume by use of the equation for the volume of a cylinder. The start of the test is initiated when 360 g of saline is added to the container.

Calculation of $V_{inf}$ and Tau ($\tau$)

The data obtained from the flooded VAUNL and flooded 0.3 psi VAUL are fit to the superabsorbent speed equation using a sum of least squares analysis to obtain the best fit for $V_{inf}$ and $\tau$. Where V is the volume from the VAUNL or 0.3 psi VAUL measurement at time t.

$$V = V_{inf}(1 - e^{-t/\tau})$$

Corrected Theoretical Time ($t_{corr}$)

The $V_{inf}$ and tau ($\tau$) are measured with the flooded VAUL method (at no confining pressure or a 0.3 psi confining pressure.

Both parameters ($V_{inf}$ and tau) must be considered, therefore a theoretical absorption time ($t_{12g/g}$) based on the measured values for $V_{inf}$, tau, and the volume (V) absorbed at that time equal to 12 g/g is calculated. The quantity of V=12 g/g was arrived at by dividing the mass of the first dose (75 g) by the amount of superabsorbent expected to act on the first dose (6.25 g). The value of 6.25 g is an approximation based on the total mass of SAP (13 g) in a typical core multiplied the typical percent wetted area of the core (48%).

$$T_{12g/g} = -\tau \times \ln\left[1 - \left(\frac{12}{V_{inf}}\right)\right]$$

Where $t_{12g/g}$=is the time to absorb the first dose of 12 g/g. $V_{inf}$=the volume absorbed at t=infinity, derived from 0.3 psi VAUL Tau ($\tau$)=characteristic swelling rate constant, derived from 0.3 psi VAUL Further correction of the theoretical absorption time in these diapers is achieved by dividing the value of $t_{12g/g}$ by the product of the percent area of SAP available and the total mass of SAP in the diaper core to give the corrected theoretical time ($t_{corr}$):

$$t_{corr} = t_{12g/g}/((SA/100)m_{sap})$$

Where $t_{12g/g}$=the time from V=12 g/g, $V_{inf}$ and $\tau$

SA=the surface area visible as a percentage of the diaper core $m_{sap}$=the total mass of superabsorbent in the laminate core Surface Area of SAP in the Laminate (SA)

The surface area (SA) of SAP available in the laminate is determined by first photographing the laminate core against a black background. The photograph is weighed and then cut to separate the areas with SAP visible. The cut visible areas of SAP is then weighed, divided by the total photograph weight and multiplied by 100 to get the percent SA.

The EDANA test methods are obtainable, for example, from the EDANA, Avenue Eugene Plasky 157, B-1030 Brussels, Belgium.

EXAMPLES

Preparation of the Base Polymer

Methods:

The measurements should, unless stated otherwise, be carried out at an ambient temperature of 23±2° C. and a relative atmospheric humidity of 50±10%. The water-absorbent polymers are mixed thoroughly before the measurement.

Example 1 (Basepolymer)

The process was performed in a concurrent spray drying plant with an integrated fluidized bed (27) as shown in FIG. 1. The reaction zone (5) had a height of 22 m and a diameter of 3.4 m. The internal fluidized bed (IFB) had a diameter of 3 m and a weir height of 0.25 m.

The drying gas was fed via a gas distributor (3) at the top of the spray dryer. The drying gas was partly recycled (drying gas loop) via a cyclone as dust separation unit (9) and a condenser column (12). The drying gas was nitrogen that comprises from 1% to 4% by volume of residual oxygen. Prior to the start of polymerization the drying gas loop was filled with nitrogen until the residual oxygen was below 4% by volume. The gas velocity of the drying gas in the reaction zone (5) was 0.79 m/s. The pressure inside the spray dryer was 4 mbar below ambient pressure.

The temperature of the gas leaving the reaction zone (5) was measured at three points around the circumference at the end of the cylindrical part of the spray dryer as shown in FIG. 3. Three single measurements (43) were used to calculate the average temperature (spray dryer outlet temperature). The drying gas loop was heated up and the dosage of monomer solution is started up. From this time the spray dryer outlet temperature was controlled to 112° C. by adjusting the gas inlet temperature via the heat exchanger (20). The gas inlet temperature was 167° C. and the steam content of the drying gas is shown in Tab. 1.

The product accumulated in the internal fluidized bed (27) until the weir height was reached. Conditioned internal fluidized bed gas having a temperature of 100° was fed to the internal fluidized bed (27) via line (25). The gas velocity of the internal fluidized bed gas in the internal fluidized bed (27) was 0.65 m/s. The residence time of the product was 150 min. The temperature of the water-absorbent polymer particles in the internal fluidized bed (27) was 77° C.

The spray dryer offgas was filtered in cyclone as dust separation unit (9) and sent to a condenser column (12) for quenching/cooling. Excess water was pumped out of the condenser column (12) by controlling the (constant) filling level inside the condenser column (12). The water inside the condenser column (12) was cooled by a heat exchanger (13) and pumped counter-current to the gas. The temperature and the steam content of the gas leaving the condenser column (12) are shown in Tab. 1. The water inside the condenser column (12) was set to an alkaline pH by dosing sodium hydroxide solution to wash out acrylic acid vapors.

The gas leaving the condenser column (12) was split to the drying gas inlet pipe (1) and the conditioned internal fluidized bed gas (25). The gas temperatures were controlled via heat exchangers (20) and (22). The hot drying gas was fed to the concurrent spray dryer via gas distributor (3). The gas distributor (3) consists of a set of plates providing a pressure drop of 2 to 4 mbar depending on the drying gas amount.

The product was discharged from the internal fluidized bed (27) via rotary valve (28) into sieve (29). The sieve (29) was used for sieving off overs/lumps having a particle diameter of more than 800 μm. The weight amounts of overs/lumps are summarized in Tab. 1.

The monomer solution was prepared by mixing first acrylic acid with 3-tuply ethoxylated glycerol triacrylate (internal crosslinker) and secondly with 37.3% by weight sodium acrylate solution. The temperature of the resulting monomer solution was controlled to 10° C. by using a heat exchanger and pumping in a loop. A filter unit having a mesh size of 250 μm was used in the loop after the pump. The initiators were metered into the monomer solution upstream of the dropletizer by means of static mixers (31) and (32) via lines (33) and (34) as shown in FIG. 1. Sodium peroxodisulfate solution having a temperature of 20° C. was added via line (33) and [2,2'-azobis[2-(2-imidazolin-2-yl)propane]dihydrochloride solution together with Brüggolite® FF7 and Cublen K 9012 (Zschimmer & Schwarz Chemie GmbH, Lahnstein, Germany) having a temperature of 10° C. was added via line (34). Each initiator was pumped in a loop and dosed via control valves to each dropletizer unit. A second filter unit having a mesh size of 140 μm was used after the static mixer (32). For dosing the monomer solution into the top of the spray dryer three dropletizer units were used as shown in FIG. 4.

A dropletizer unit consisted of an outer pipe (47) having an opening for the dropletizer cassette (49) as shown in FIG. 5. The dropletizer cassette (49) was connected with an inner pipe (48). The inner pipe (48) having a PTFE block (50) at the end as sealing can be pushed in and out of the outer pipe (47) during operation of the process for maintenance purposes.

The temperature of the dropletizer cassette (49) was controlled to 8° C. by water in flow channels (55) as shown in FIG. 8. The dropletizer cassette (49) had 256 bores having a diameter of 170 μm and a bore spacing of 15 mm. The dropletizer cassette (49) consisted of a flow channel (56) having essential no stagnant volume for homogeneous distribution of the premixed monomer and initiator solutions and one droplet plate (53). The droplet plate (53) had an angled configuration with an angle of 3°. The droplet plate (53) was made of stainless steel and had a length of 630 mm, a width of 128 mm and a thickness of 1 mm.

The feed to the spray dryer consisted of 9.56% by weight of acrylic acid, 33.73% by weight of sodium acrylate, 0.013% by weight of 3-tuply ethoxylated glycerol Triacrylate (purity approx. 85% by weight), 0.054% by weight of [2,2'-azobis[2-(2-imidazolin-2-yl)propane]dihydrochloride, 0.0018% by weight of Brüggolite® FF7 (Brüggemann Chemicals; Heilbronn; Germany), 0.071% by weight of sodiumperoxodisulfate and 0.054% by weight of 1-Hydroxyethane 1,1-diphosphonic acid, disodium salt (Cublen K 9012) water. The degree of neutralization was 73%. The feed per bore was 1.4 kg/h.

The resulting water-absorbent polymer particles were analyzed. The conditions and results are summarized in Tab. 1 to 3.

Example 2 (Basepolymer)

The process was performed in a concurrent spray drying plant with an integrated fluidized bed (27) as shown in FIG. 1. The reaction zone (5) had a height of 22 m and a diameter of 3.4 m. The internal fluidized bed (IFB) had a diameter of 3 m and a weir height of 0.25 m.

The drying gas was fed via a gas distributor (3) at the top of the spray dryer. The drying gas was partly recycled (drying gas loop) via a cyclone as dust separation unit (9) and a condenser column (12). The drying gas was nitrogen that comprises from 1% to 4% by volume of residual oxygen. Prior to the start of polymerization the drying gas loop was filled with nitrogen until the residual oxygen was below 4% by volume. The gas velocity of the drying gas in the reaction zone (5) was 0.79 m/s. The pressure inside the spray dryer was 4 mbar below ambient pressure.

The temperature of the gas leaving the reaction zone (5) was measured at three points around the circumference at the end of the cylindrical part of the spray dryer as shown in FIG. 3. Three single measurements (43) were used to calculate the average temperature (spray dryer outlet temperature). The drying gas loop was heated up and the dosage of monomer solution is started up. From this time the spray dryer outlet temperature was controlled to 115° C. by adjusting the gas inlet temperature via the heat exchanger (20). The gas inlet temperature was 167° C. and the steam content of the drying gas is shown in Tab. 1.

The product accumulated in the internal fluidized bed (27) until the weir height was reached. Conditioned internal fluidized bed gas having a temperature of 117° was fed to the internal fluidized bed (27) via line (25). The gas velocity of the internal fluidized bed gas in the internal fluidized bed (27) was 0.65 m/s. The residence time of the product was 150 min. The temperature of the water-absorbent polymer particles in the internal fluidized bed (27) was 78° C.

The spray dryer offgas was filtered in cyclone as dust separation unit (9) and sent to a condenser column (12) for quenching/cooling. Excess water was pumped out of the condenser column (12) by controlling the (constant) filling level inside the condenser column (12). The water inside the condenser column (12) was cooled by a heat exchanger (13) and pumped counter-current to the gas. The temperature and the steam content of the gas leaving the condenser column (12) are shown in Tab. 1. The water inside the condenser column (12) was set to an alkaline pH by dosing sodium hydroxide solution to wash out acrylic acid vapors.

The gas leaving the condenser column (12) was split to the drying gas inlet pipe (1) and the conditioned internal fluidized bed gas (25). The gas temperatures were controlled via heat exchangers (20) and (22). The hot drying gas was fed to the concurrent spray dryer via gas distributor (3). The gas distributor (3) consists of a set of plates providing a pressure drop of 2 to 4 mbar depending on the drying gas amount.

The product was discharged from the internal fluidized bed (27) via rotary valve (28) into sieve (29). The sieve (29) was used for sieving off overs/lumps having a particle diameter of more than 800 μm. The weight amounts of overs/lumps are summarized in Tab. 1.

The monomer solution was prepared by mixing first acrylic acid with 3-tuply ethoxylated glycerol triacrylate (internal crosslinker) and secondly with 37.3% by weight sodium acrylate solution. The temperature of the resulting monomer solution was controlled to 10° C. by using a heat exchanger and pumping in a loop. A filter unit having a mesh size of 250 μm was used in the loop after the pump. The initiators were metered into the monomer solution upstream of the dropletizer by means of static mixers (31) and (32) via lines (33) and (34) as shown in FIG. 1. Sodium peroxodisulfate solution having a temperature of 20° C. was added via line (33) and [2,2'-azobis[2-(2-imidazolin-2-yl)propane]dihydrochloride solution together with Brüggolite® FF7 and Blancolen® HP having a temperature of 10° C. was added via line (34). Each initiator was pumped in a loop and dosed via control valves to each dropletizer unit. A second filter unit having a mesh size of 140 μm was used after the static mixer (32). For dosing the monomer solution into the top of the spray dryer three dropletizer units were used as shown in FIG. 4.

A dropletizer unit consisted of an outer pipe (47) having an opening for the dropletizer cassette (49) as shown in FIG. 5. The dropletizer cassette (49) was connected with an inner pipe (48). The inner pipe (48) having a PTFE block (50) at the end as sealing can be pushed in and out of the outer pipe (47) during operation of the process for maintenance purposes.

The temperature of the dropletizer cassette (49) was controlled to 8° C. by water in flow channels (55) as shown in FIG. 8. The dropletizer cassette (49) had 256 bores having a diameter of 170 μm and a bore spacing of 15 mm. The dropletizer cassette (49) consisted of a flow channel (56) having essential no stagnant volume for homogeneous distribution of the premixed monomer and initiator solutions and one droplet plate (53). The droplet plate (53) had an angled configuration with an angle of 3°. The droplet plate (53) was made of stainless steel and had a length of 630 mm, a width of 128 mm and a thickness of 1 mm.

The feed to the spray dryer consisted of 9.56% by weight of acrylic acid, 33.73% by weight of sodium acrylate, 0.013% by weight of 3-tuply ethoxylated glycerol Triacrylate (purity approx. 85% by weight), 0.071% by weight of [2,2'-azobis[2-(2-imidazolin-2-yl)propane]dihydrochloride, 0.0028% by weight of Brüggolite® FF7 (Brüggemann Chemicals; Heilbronn; Germany), 0.054% by weight of Blancolene® HP (Brüggemann Chemicals; Heilbronn; Germany) 0.099% by weight of sodiumperoxodisulfate and water. The degree of neutralization was 73%. The feed per bore was 1.4 kg/h.

The resulting water-absorbent polymer particles were analyzed. The conditions and results are summarized in Tab. 1 to 3.

TABLE 1

Process conditions of the polymerization for examples 1 to 7

| Example | Steam Content CC kg/kg | Steam Content GD kg/kg | T gas inlet ° C. | T gas outlet ° C. | T gas IFB ° C. | T IFB ° C. | T CC ° C. | T GDU ° C. |
|---|---|---|---|---|---|---|---|---|
| 1 | 0.1100 | 0.0651 | 167 | | | | 54 | 45 |
| 2 | | | | 115 | 107 | 77 | | |

Steam Content CC: steam content of the gas leaving the condenser column (12)
Steam Content GD: steam content of the gas prior to the gas distributor (3)
T gas inlet: temperature of the gas prior to the gas distributor (3)
T gas outlet: temperature of the gas leaving the reaction zone (5)
T gas IFB temperature of the gas entering the internal fluidized bed (27) via line (25)
T IFB: temperature of the water-absorbent polymer particles in the fluidized bed (27)
T CC: temperature of the gas leaving the condenser column (12)
T GDU: temperature of the gas leaving the gas drying unit (37)

TABLE 2

Properties of the water-absorbent polymer particles (base polymer)

| Example | Bulk Density g/cm³ | CRC g/g | AUL g/g | Residual Monomers Ppm | Extractables wt. % | Moisture wt. % | L | a | b |
|---|---|---|---|---|---|---|---|---|---|
| 1 | 68.7 | 45.8 | 5.6 | 8990 | 11.3 | 8.3 | 93.9 | 2.1 | 2.9 |
| 2 | 69.3 | 61.8 | 7.8 | 5250 | 11.8 | 8.2 | 94.2 | 2.2 | 3.0 |

TABLE 3

Particles Size Distribution (PSD) of the water-absorbent polymer particles (base polymer), measured by sieve fraction analysis

| Example | 0-100 μm wt % | 100-200 μm wt % | 200-250 μm wt % | 250-300 μm wt % | 300-400 μm wt % | 400-500 μm wt % | 500-600 μm wt % | 600-850 μm wt % | 850-1000 μm wt % | >1000 μm wt % |
|---|---|---|---|---|---|---|---|---|---|---|
| 1 | | | | | | | | | | |
| 2 | 0.4 | 1.9 | 5.2 | 8.2 | 32.2 | 32.7 | 10.1 | 8.3 | 0.9 | 0.1 |

Examples 3 and 4

General Description

Figure 15:
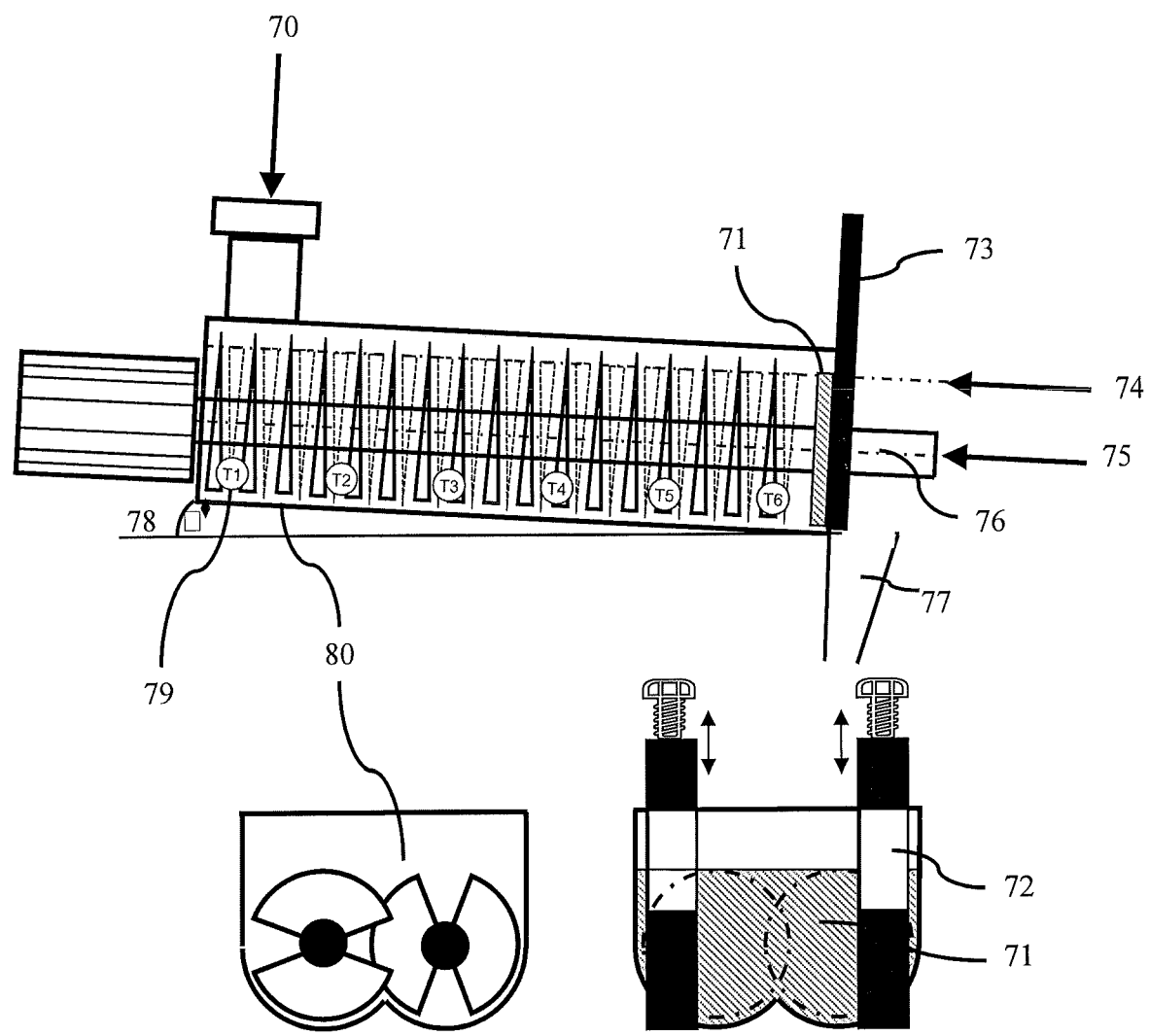

In a Schugi Flexomix® (model Flexomix 160, manufactured by Hosokawa Micron B.V., Doetinchem, the Netherlands) with a speed of 2000 rpm, the base polymer was coated with a surface-postcrosslinker solution by using 2 or 3 round spray nozzle systems (model Gravity-Fed Spray Set-ups, External Mix Typ SU4, Fluid Cap 60100 and Air Cap SS-120, manufactured by Spraying Systems Co, Wheaton, Ill., USA) and then filled via base polymer feed (70) and dried in a thermal dryer (65) (model NPD 5W-18, manufactured by GMF Gouda, Waddinxveen, the Netherlands) with a speed of the shaft (76) of 6 rpm. The thermal dryer (65) has two paddles with a shaft offset of 90° (80) and a fixed discharge zone (71) with two flexible weir plates (73). Each weir has a weir opening with a minimal weir height at 50% (75) and a maximal weir opening at 100% (74) as shown in FIG. 15.

The inclination angle α (78) between the floor plate and the thermal dryer was approx. 3°. The weir height of the thermal dryer was between 50 to 100%, corresponding to a residence time of approx. 40 to 150 min, by a product density of approx. 700 to 750 kg/m³. The product temperature in the thermal dryer was in a range of 120 to 165° C. After drying, the surface-postcrosslinked polymer was transported over discharge cone (77) in a cooler (model NPD 5W-18, manufactured by GMF Gouda, Waddinxveen, the Netherlands), to cool down the surface postcrosslinked polymer to approx. 60° C. with a speed of 11 rpm and a weir height of 145 mm. After cooling, the material was sieved with a minimum cut size of 150 μm and a maximum cut size of 710 μm.

Example 3

Ethylene carbonate, water and an aqueous aluminum sulfate solution (26% by weight) were premixed and used as surface-postcrosslinker solution as summarized in Tab. 5. As aluminum sulfate, Gecedral® AS (manufactured by BK Giulini GmbH, Ludwigshafen, Germany) was used.

4.7 wt % of a 0.055% aqueous solution of Span® 20, having a temperature of approx. 25° C., was additionally added into the cooler using two nozzles in the first third of the cooler. The nozzles were placed below the product bed.

The resulting water-absorbent polymer particles were analyzed. The trial conditions and results are summarized in Tab. 4 to 6.

Example 4

Ethylene carbonate, water, Span® 20 (Croda, Nettetal, Germany)), aqueous aluminum lactate (22% by weight) were premixed and used as surface-postcrosslinker solution as summarized in Tab. 5. As aluminum lactate, Lothragon® Al 220 (manufactured by Dr. Paul Lohmann GmbH, Emmerthal, Germany) was used.

4.0 wt % of a 0.125% aqueous solution of Span®20 solution (Croda, Nettetal, Germany) and 4.4 wt % of a 5.7% aqueous solution of aluminum lactate solution were additionally added into the cooler using two nozzles in the first third of the cooler. Both solution having a temperature of approx. 25° C. The nozzles were placed below the product bed.

The resulting water-absorbent polymer particles were analyzed. The trial conditions and results are summarized in Tab. 4 to 8.

TABLE 4

Process conditions of the thermal dryer for the surface postcrosslinking (SXL)

| Example Unit | Product Temp. Set Value ° C. | Steam Pressure Wave Bar | Steam Pressure Jacket Bar | Heater T1 ° C. | Heater T2 ° C. | Heater T3 ° C. | Heater T4 ° C. | Heater T5 ° C. | Heater T6 ° C. | Through-put kg/h | Heater Weir % | No. of Nozzles | Pos. of Nozzles |
|---|---|---|---|---|---|---|---|---|---|---|---|---|---|
| 3 | 150 | 5.5 | 5.5 | 92 | 94 | 119 | 131 | 142 | 150 | 470 | 80 | 3 | 90/180/270° |
| 4 | 145 | 4.7 | 4.8 | 94 | 98 | 117 | 128 | 139 | 145 | 470 | 80 | 3 | 90/180/270° |

TABLE 5

Surface-postcrosslinker formulation of the thermal treatment in the heater and remoistening in the cooler

| | | | SXL | | | Cooler | | |
|---|---|---|---|---|---|---|---|---|
| Example | Base polymer | EC bop % | Water bop % | Al-lactate (dry) bop % | Al-Sulfate (dry) bop ppm | 0.125 wt % aq. solution of Span ® 20 bop % | 0.055 wt % aq. solution of Span ® 20 bop % | 5.7 wt % aq. solution of aluminum lactate bop % |
| 3 | Example 1 | 2.0 | 5.0 | | 0.2 | | 4.7 | |
| 4 | Example 2 | 2.0 | 5.0 | 0.1 | | 4.0 | | 4.4 |

EC: Ethylene carbonate;
bop: based on polymer

TABLE 6

Physical properties of the polymer particles after surface-postcrosslinking

| Example | CRC g/g | AUL g/g | AUHL g/g | Moisture % | Residual Monomers ppm | Extractables % | Bulk Density g/100 ml |
|---|---|---|---|---|---|---|---|
| 3 | 42.9 | 34.8 | 23.1 | 4.1 | 409 | 3 | 77 |
| 4 | 49.2 | 35.6 | 15.2 | 4.9 | 529 | 7 | 86 |

TABLE 7

Particle size distribution of the polymer particles after surface-postcrosslinking-Sieve fractions

| Example | <106 μm % | >106 μm % | >200 μm % | >250 μm % | >300 μm % | >400 μm % | >500 μm % | >600 μm % | >710 μm % |
|---|---|---|---|---|---|---|---|---|---|
| 3 | 0.2 | 1.2 | 3.3 | 9.3 | 41.7 | 34.9 | 7.5 | 1.6 | 0.2 |
| 4 | 0.1 | 1.6 | 7.2 | 15.5 | 53.9 | 20.5 | 0.8 | 0.3 | 0.1 |

TABLE 8

Color stability of the polymer particles after surface-postcrosslinking (Accelerated Aging Test)

| | 0 d | | | 7 d | | | 14 d | | | 21 d | | |
|---|---|---|---|---|---|---|---|---|---|---|---|---|
| Example | L | A | B | L | a | b | L | a | b | L | a | b |
| 3 | 93.2 | −0.4 | 8.5 | 81.0 | 1.3 | 10.0 | 79.0 | 1.7 | 11.1 | 77.0 | 2. | 11.9 |
| 4 | 93.6 | −1.7 | 10.9 | 83.8 | −1.0 | 10.6 | 83.9 | −0.7 | 11.1 | 82.9 | −0.5 | 12.1 |

Example 4A Agglomeration of Fine Particles of Superabsorbent

A 5 liter Loedige plow shear mixer was charged with 600 g of superabsorbent fine particles (fraction of surface post-crosslinked absorbent particles with a particle size of less than 150 μm removed from the superabsorbent production of ASAP 700®, a commercial product of BASF SE) with a CRC of 29 g/g and heated to 50° C. The mixer is run at a speed of 400 rpm and a solution consisting of 1 g ethyleneglycol diglycidyl ether (EGDGE) in 235 g water, 62 g of 2-propanol, and 2.5 g of Sokalan® CP45 (BASF SE; Ludwigshafen; Germany) is sprayed onto the rapidly mixing powder via an atomizer sprayer at a feed rate of 45 ml/minute. The resulting mixture is dried in an explosion proof oven at 130° C. for 1 hour and then sized to 106-850 μm. The PSD of the resulting particles is 380 μm. The features of the resulting water-absorbent polymer materials (superabsorbent) are summarized in Tab. 9 and 10.

Example 5 Handmade Fluid-Absorbent Articles (Diapers)

First, laminates (absorbent core) were prepared by distributing the desired amount of water-absorbent polymer, usually 310-340 grams per square meter (gsm), onto the 12.5 gsm polypropylene 'topsheet' nonwoven that has 0.45 grams of Beardow & Adams BamCare 501 hot-melt pressure sensitive adhesive already applied. Then another 0.45 grams of adhesive is applied and a 9.5 gsm polypropylene nonwoven is compressed onto the structure to complete the laminate. The adhesive is sprayed on with a 0.05 mm spray nozzle such that there are only thin lines of the adhesive. Normally, the structure consists of five lines of superabsorbent (totally about 13 g superabsorbent) that are each 38 cm long, with a total laminate core length of 42 cm. The width of the laminate cores is typically 10 cm. However, other patterns have been evaluated such as a continuous layer of superabsorbent and spots of superabsorbents.

Once made, the laminate (absorbent paper or absorbent core respectively) is then placed into a diaper chassis consisting of a backsheet and a topsheet. If acquisition distribution layer (ADL) is to be used it is placed between the topsheet (89) and the laminate (80) oriented toward the front of the diaper such that the center of the ADL is 13 cm from the top edge of the laminate core. The diaper is then sealed with either tape or hot-melt adhesive.

Example 6 Hanging U-Shaped (HUS) Testing

The handmade diapers are placed in a HUS unit (FIG. 19 A) with the edges of the diaper 3.5 cm from the top of the testing unit (FIG. 19B, C) (at the Black mark (14)). The dosing is set at 15.5 cm from the top of the testing unit, or 12 cm from the top of the diaper following the angle of the uprights, through a 3.75 mm saline dosing port (18). The saline dosing port (18) is connected to a pump which delivers the 35° C. saline at 15 g/second. For this size diaper a dosing mass of 4×75 g is used. Each intake time (first, second, third, fourth, each dose of 75 g) is measured from the start of the dosing until all the saline is absorbed by the diaper. Wait time between each dose was 10 minutes from the start of the dose. The results are shown in Tab. 10, 11, 11A and 12 for diapers with different absorbent cores.

The features of the water-absorbent polymer materials (superabsorbent) tested in absorbent paper/absorbent core are summarized in Tab. 9

TABLE 9

Superabsorbent Properties

| Superabsorbent | CRC (g/g) | AUL (g/g) | Bulk density (g/ml) | Surface Area Kr BET (cm$^2$/g) | $t_{corr}$ (sig) | SFC |
|---|---|---|---|---|---|---|
| Example 3* | 42.9 | 23.1 | 0.77 | 711 | 19.8 | 0 |
| 20% insta snow/80% Example 3 | 39.1 | 24.1 | 0.67 | 799 | 16.6 | 4 |
| 35% insta snow/65% Example 3 | 35.9 | 23.4 | 0.58 | 866 | 15.8 | 5 |
| 50% insta snow/50% Example 3 | 32.8 | 22.7 | 0.51 | 932 | 11.6 | 8 |
| 65% insta snow/35% Example 3 | 29.6 | 21.9 | 0.45 | 998 | 11.4 | 15 |
| 80% insta snow/20% Example 3 | 26.4 | 21.2 | 0.41 | 1065 | 6.8 | 18 |
| Insta snow | 22.2 | 20.3 | 0.37 | 1153 | 4.7 | 20 |
| Example 4A | 18.9 | 18.4 | 0.45 | 1161 | | 11 |
| 30% Example 4A/70% Example 3 | 33.4 | 21.3 | 0.67 | 846 | 18.6 | 1 |
| 40% Example 4A/60% Example 3 | 32.2 | 21.5 | 0.62 | 891 | 17.7 | 2 |
| HySorb 9400* | 29.6 | 21.3 | 0.75 | 285 | 21.3 | 10 |

*Reference Example
Hysorb ® 9400 is a commercial product of BASF SE, Ludwigshafen, Germany
Insta snow purchased from Steve and spangler Science, Englewood, Colorado, US.

The following table summarizes properties in respect to liquid acquisition and retention of the tested water-absorbent polymer materials

TABLE 10

| Superabsorbent | Intake Time (s) 1 | from 2 g flooded VAUL, 0.3 psi $V_{inf}$(g/g) | tau (s) | $t_{12g/g}$ (s) | $t_{corr}$ (s/g) | from 2 g flooded VAUNL (no load) $V_{inf}$(g/g) | tau (s) | $t_{12g/g}$ (s) | $t_{corr}$ (s/g) | SAP area (%) | Mass |
|---|---|---|---|---|---|---|---|---|---|---|---|
| Example 3-100%* | 30.0 | 30.8 | 329 | 162.2 | 19.8 | 48.4 | 282 | 80.4 | 9.8 | 62.2 | 13.2 |
| 20% insta snow/80% Example 3 | 13.4 | 29.7 | 255 | 132.0 | 16.6 | 47.2 | 207 | 60.7 | 7.6 | 62.3 | 12.8 |
| 35% insta snow/65% Example 3 | 7.9 | 26.3 | 206 | 125.5 | 15.8 | 44.5 | 150 | 47.1 | 5.9 | 62.3 | 12.8 |
| 50% insta snow/50% Example 3 | 8.0 | 27.7 | 162 | 92.2 | 11.6 | 43.3 | 99 | 32.2 | 4.0 | 62.4 | 12.7 |
| 65% insta snow/35% Example 3 | 5.7 | 23.4 | 127 | 91.5 | 11.4 | 41.7 | 53 | 18.1 | 2.3 | 62.5 | 12.8 |
| 80% insta snow/20% Example 3 | 6.1 | 22.8 | 71 | 53.5 | 6.8 | 38.8 | 21 | 7.9 | 1.0 | 62.6 | 12.6 |
| insta snow-100% | 7.1 | 20.3 | 42 | 37.4 | 4.7 | 40.6 | 12 | 4.2 | 0.5 | 62.6 | 12.8 |
| 30% Example 4A/70% Example 3 | 8.7 | | | | | | | | | 62.5 | 13.1 |
| 40% Example 4A/60% Example 3 | 9.6 | | | | | | | | | 62.8 | 13.3 |

*Reference Example
Insta snow purchased from Steve and Spangler Science, Englewood, Colorado, US.
The intake times are measured with handmade diapers (without aqusition distribution layer, curly fibres or cellulosic fluff).
As shown in Tab. 10 blends of a slow water-absorbent polymer (high tau) with a fast (low tau) water-absorbent polymer behave as if only the fast water-absorbent polymer is present in the first intake. This gives a curved relationship when $t_{corr}$ is plotted against the actual first intake time.

TABLE 11

Handmade diapers with 70 gsm PET ADL

| Superabsorbent | Intake Time (s) 1 | 2 | 3 | 4 | after 4th dose Rewet (g) |
|---|---|---|---|---|---|
| Example 3* | 30.0 | 35.0 | 40.0 | 30.0 | 0.8 |
| 20% insta snow/80% Example 3 | 13.4 | 14.7 | 20.0 | 21.0 | 1.4 |
| 35% insta snow/65% Example 3 | 7.9 | 7.3 | 9.3 | 13.0 | 4.5 |
| 50% insta snow/50% Example 3 | 8.0 | 6.6 | 9.8 | 15.0 | 10.4 |
| 65% insta snow/35% Example 3 | 5.7 | 6.6 | 7.0 | 10.0 | 12.4 |
| 80% insta snow/20% example 3 | 6.1 | 6.8 | 8.7 | 12.0 | 23.7 |
| Insta snow | 7.1 | 7.1 | 10.2 | 27.0 | 41 |
| HySorb ® 9400* | 33.0 | 21.0 | 21.0 | 32.0 | 14.0 |
| Swaddlers Core* | 29 | 9.2 | 16.1 | 119.0 | 35.6 |

*Reference example
The intake times and Rewet are measured with a 70 gsm PET ADL on top of the laminate, extracted from First Quality up&up diaper purchased in NC, US
Swaddlers core means: Core of a commercial diaper Swaddler by The Procter &Gamble Company, Cincinatti, OH, US

TABLE 11A

Handmade diapers with 60 gsm PET ADL

| Superabsorbent | Intake Time (s) | | | | after 4th dose Rewet (g) |
|---|---|---|---|---|---|
| | 1 | 2 | 3 | 4 | |
| 30% Example 4A/70% Example 3 | 8.7 | 13.2 | 17 | 30 | 1.0 |
| 40% Example 4A/60% Example 3 | 9.6 | 14.1 | 21 | 33 | 5.1 |

The intake times and Rewet are measured with a 60 gsm PET ADL on top of the laminate

TABLE 12

Handmade diapers without ADL

| Superabsorbent | Intake Time (s) | | | | after 4th dose Rewet (g) |
|---|---|---|---|---|---|
| | 1 | 2 | 3 | 4 | |
| Example 3* | 38.6 | 42.9 | 42.0 | 34.0 | 0.9 |
| 20% insta snow/80% Example 3 | 20.3 | 19.9 | 20.0 | 23.0 | 3.6 |
| 35% insta snow/65% Example 3 | 10.9 | 9.9 | 12.0 | 14.0 | 11.5 |
| 50% insta snow/50% Example 3 | 7.6 | 7.8 | 9.3 | 11.0 | 22.2 |
| 65% insta snow/35% Example 3 | 6.6 | 7.3 | 8.1 | 13.0 | 34.1 |
| 80% insta snow/20% Example 3 | 6.7 | 7.6 | 11.0 | 16.0 | 42.4 |
| Insta SNOW | 7.8 | 7.1 | 8.6 | 13.0 | 53 |
| Swaddlers' core without ADL* | 52 | 34 | 66 | 147 | 43 |

*Reference Examples
The intake times and Rewet are measured without an ADL on top of the laminate (absorbent core)
Swaddlers' core means: Core of a commercial diaper Swaddler by The Procter &Gamble Company, Cincinatti, OH, US

The invention claimed is:

1. A fluid-absorbent article, comprising
   (A) an upper liquid-pervious layer (89),
   (B) a lower liquid-impervious layer (83),
   (C) a fluid-absorbent core (80) between the layer (89) and the layer (83), comprising at least one layer (91), comprising from
   0 to 20% by weight fibrous material and from 80 to 100% by weight a water-absorbent polymer material, based on the sum of water-absorbent polymer material and fibrous material;
   wherein the fluid absorbent article has a first intake time of 15 seconds or less by the hanging U-shape test (HUS);
   wherein the water-absorbent polymer material is a blend of at least two water-absorbent polymer materials comprising 20 to 100 wt.-% of a fast superabsorbent and 0 to 80 wt.-% of a second water-absorbent polymer material; and
   wherein the fast superabsorbent has a surface area of at least 1000 cm²/q measured by BET.

2. The fluid-absorbent article according to claim 1, wherein the fluid absorbent article has a first intake time of 12 seconds or less by the hanging U-shape test (HUS).

3. The fluid-absorbent article according to claim 1, wherein the fluid absorbent article has a first intake time of 7 seconds or less by the hanging U-shape test (HUS).

4. The fluid-absorbent article according to claim 1, wherein an acquisition distribution layer (D) is present between upper liquid-pervious layer (89) and the fluid-absorbent core (80).

5. The fluid-absorbent article according to claim 1, wherein the core comprises a blend of at least 30 to 100 wt.-% of the fast superabsorbent and 0 to 70 wt.-% of the second water-absorbent polymer material.

6. The fluid-absorbent article according to claim 1, wherein the blend and/or at least the fast superabsorbent has a $t_{corr}$ value of 16 s/g or less, wherein the $t_{corr}$ is defined by the following equation:

$$t_{corr} = \frac{\frac{t_{12g}}{g}}{(SA/100)m_{sap}}.$$

7. The fluid-absorbent article according to claim 6, wherein the blend and/or at least the fast superabsorbent having a $t_{corr}$ value of 9 sec/g or less.

8. The fluid-absorbent article according to claim 6, wherein the blend and/or at least the fast superabsorbent having a $T_{corr}$ value of 5 sec/g or less.

9. The fluid-absorbent article according to claim 1, wherein at least the fast superabsorbent has a SFC of at least $18 \times 10^{-7}$ cm³s/g.

10. The fluid-absorbent article according to claim 1, wherein at least the second water-absorbent polymer material has a sphericity of 0.89.

11. The fluid-absorbent article according to claim 1, further comprising 0-20% by weight binding agents.

12. A fluid absorbent core (80), comprising at least one layer (91), comprising from 0 to 20% by weight fibrous material and from 80 to 100% by weight a water-absorbent polymer material, based on the sum of water-absorbent polymer material and fibrous material, wherein the at least one layer (91) comprises a blend of at least 20 to 100 wt.-% of a fast superabsorbent and 0 to 80 wt-% of a second water-absorbent polymer material; and
   wherein the fast superabsorbent has a surface area of at least 1000 cm²/g measured by BET; and
   wherein the fluid absorbent core has a first intake time of 15 seconds or less by the hanging U-shape test (HUS).

13. The fluid absorbent core (80) according to claim 12, wherein the at least one layer (91) comprises a blend of at least 30 to 100 wt.-% of the fast superabsorbent and 0 to 70 wt.-% of the second water-absorbent polymer material.

14. The fluid absorbent core according to claim 12, wherein the at least one layer (91) is sandwiched by tissue layers (95/96).

* * * * *